US012673316B2

(12) United States Patent
Okumura et al.

(10) Patent No.: US 12,673,316 B2
(45) **Date of Patent: \*Jul. 7, 2026**

(54) CATALYST, METHOD FOR FILLING CATALYST, AND METHOD FOR PRODUCING COMPOUND USING CATALYST

(71) Applicant: NIPPON KAYAKU KABUSHIKI KAISHA, Tokyo (JP)

(72) Inventors: Shigeki Okumura, Yamaguchi (JP); Shogo Yasuda, Yamaguchi (JP); Tomohiro Obata, Yamaguchi (JP); Seiichiro Fukunaga, Yamaguchi (JP); Tomoyuki Kawamura, Yamaguchi (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 947 days.

This patent is subject to a terminal disclaimer.

(21) Appl. No.: 17/783,209

(22) PCT Filed: Jan. 8, 2021

(86) PCT No.: PCT/JP2021/000587
§ 371 (c)(1),
(2) Date: Jun. 7, 2022

(87) PCT Pub. No.: WO2021/141133
PCT Pub. Date: Jul. 15, 2021

(65) Prior Publication Data
US 2023/0015502 A1 Jan. 19, 2023

(30) Foreign Application Priority Data

Jan. 10, 2020 (JP) ................................. 2020-002507
Jan. 10, 2020 (JP) ................................. 2020-002509
Mar. 12, 2020 (JP) ................................. 2020-042592

(51) Int. Cl.
*B01J 23/887* (2006.01)
*B01J 21/04* (2006.01)
(Continued)

(52) U.S. Cl.
CPC ........... *B01J 23/8876* (2013.01); *B01J 21/04* (2013.01); *B01J 21/08* (2013.01); *B01J 35/19* (2024.01);
(Continued)

(58) Field of Classification Search
CPC ........ B01J 23/8876; B01J 21/04; B01J 21/08; B01J 35/19; B01J 35/36; B01J 35/70;
(Continued)

(56) References Cited

U.S. PATENT DOCUMENTS 3,959,384 A * 5/1976 Takenaka ............... B01J 27/192
568/479
3,966,823 A * 6/1976 Takenaka ............... B01J 27/192
585/629
(Continued)

FOREIGN PATENT DOCUMENTS

CN 101269333 9/2008
CN 107848920 3/2018
(Continued)

OTHER PUBLICATIONS

International Search Report dated Mar. 23, 2021 in International (PCT) Application No. PCT/JP2021/000587.
(Continued)

*Primary Examiner* — Fereydoun G Sajjadi
*Assistant Examiner* — Y. Lynnette Kelly-O'Neill
(74) *Attorney, Agent, or Firm* — Wenderoth, Lind & Ponack, L.L.P.

(57) ABSTRACT

A catalyst containing, as an essential component, molybdenum; bismuth; and cobalt, in which a sum (S) of ratios of
(Continued)

peak intensities expressed by the following formula in an X-ray diffraction pattern obtained by using CuKα rays as an X-ray source is 42 or more and 113 or less. S={(peak intensity at 2θ=14.1°±0.1°)+(peak intensity at 2θ=25.4°±0.1°)+(peak intensity at 2θ=28.5°±0.1°)}/(peak intensity at 2θ=26.5°±0.1°)×100.

7 Claims, 3 Drawing Sheets

(51) Int. Cl.

| | |
|---|---|
| *B01J 21/08* | (2006.01) |
| *B01J 35/00* | (2006.01) |
| *B01J 35/36* | (2024.01) |
| *B01J 35/70* | (2024.01) |
| *C07C 2/10* | (2006.01) |
| *C07C 45/32* | (2006.01) |
| *C07C 51/25* | (2006.01) |
| *C07C 57/04* | (2006.01) |

(52) U.S. Cl.
CPC .............. *B01J 35/36* (2024.01); *B01J 35/70* (2024.01); *C07C 2/10* (2013.01); *C07C 45/32* (2013.01); *C07C 51/25* (2013.01); *C07C 57/04* (2013.01); *B01J 2235/15* (2024.01)

(58) Field of Classification Search
CPC .... B01J 2235/15; B01J 8/0015; B01J 8/0453; B01J 2523/00; B01J 23/002; B01J 37/0018; B01J 37/0045; B01J 37/04; B01J 8/06; B01J 2208/06; B01J 2523/13; B01J 2523/15; B01J 2523/54; B01J 2523/68; B01J 2523/822; B01J 2523/842; B01J 2523/845; B01J 2523/847; C07C 2/10; C07C 45/32; C07C 51/25; C07C 57/04; C07C 2523/887; C07C 45/35; C07C 51/252; C07C 5/48; C07C 11/167; C07C 47/22; C07B 33/00
USPC .............................................. 562/512, 512.2
See application file for complete search history.

(56) References Cited

U.S. PATENT DOCUMENTS

| | | | |
|---|---|---|---|
| 6,632,965 | B1 | 10/2003 | Tanimoto et al. |
| 2011/0112325 | A1 | 5/2011 | Tanimoto et al. |
| 2015/0238939 | A1 | 8/2015 | Yoshida et al. |
| 2016/0145180 | A1 | 5/2016 | Kawamura et al. |
| 2016/0145181 | A1 | 5/2016 | Nakazawa et al. |
| 2018/0029018 | A1 | 2/2018 | Kawamura et al. |
| 2018/0186712 | A1* | 7/2018 | Sugiyama ............ B01J 37/0018 |
| 2018/0222851 | A1 | 8/2018 | Lugmair et al. |
| 2019/0070591 | A1 | 3/2019 | Motomura et al. |

FOREIGN PATENT DOCUMENTS

| | | |
|---|---|---|
| CN | 108136377 | 6/2018 |
| EP | 2671862 | 12/2013 |
| EP | 2995375 | 3/2016 |
| JP | 2001-48817 | 2/2001 |
| JP | 2014-094353 | 5/2014 |
| JP | 2017-024009 | 2/2017 |
| JP | 2018-140326 | 9/2018 |
| WO | 2010/038677 | 4/2010 |
| WO | 2013/059304 | 4/2013 |
| WO | 2014/051090 | 4/2014 |
| WO | 2015/008814 | 1/2015 |
| WO | 2015/008815 | 1/2015 |
| WO | 2016/136882 | 9/2016 |
| WO | 2017/010159 | 1/2017 |
| WO | 2017/069119 | 4/2017 |

OTHER PUBLICATIONS

Notification of Reasons for Refusal issued Jun. 3, 2021 in Japanese Patent Application No. 2021-521552, with English translation.
Extended European Search Report issued Aug. 5, 2022 in European Patent Application No. 21738713.3.
Jung, Ji Chul et al., "Effect of calcination temperature on the catalytic performance of $Co_9Fe_3Bi_1Mo_{12}O_{51}$ in the oxidative dehydrogenation of n-butene to 1,3-butadiene", Catalysis Communications, 2008, vol. 9, No. 10, pp. 2059-2062.
Office Action issued Jul. 5, 2023 in corresponding European Patent Application No. 21738713.3.
Office Action issued Dec. 11, 2024 in the corresponding Singapore Patent Application No. 11202205662X.
Office Action issued May 10, 2022 in Chinese Patent Application No. 202180003590.1, with English translation.

* cited by examiner

DIFFRACTION ANGLE 2θ

DIFFRACTION ANGLE 2θ

CATALYST, METHOD FOR FILLING CATALYST, AND METHOD FOR PRODUCING COMPOUND USING CATALYST

TECHNICAL FIELD

The present invention relates to a method for filling a catalyst and a method for producing a compound using a catalyst.

BACKGROUND ART

A method for using propylene, isobutylene, t-butyl alcohol or the like as a raw material to produce a corresponding unsaturated aldehyde or unsaturated carboxylic acid, or a catalytic gas phase oxidation method for producing 1,3-butadiene from butenes are widely carried out industrially.

In particular, regarding the method for using propylene, isobutylene, t-butyl alcohol or the like as a raw material to produce a corresponding unsaturated aldehyde or unsaturated carboxylic acid, many reports have been made for means for improving the yield and improving the catalytic activity (for example, Patent Literature 1 and the like).

Among them, Patent Literature 2 describes that a catalyst exhibiting a high yield and a high selectivity can be obtained by controlling a ratio $Ri=Pi/Ph$ of an intensity $Pi$ of a diffraction peak (i) of $\beta\text{-}Bi_2Mo_2O_9$ appearing at $2\theta=27.76°\pm0.1°$ to an intensity $Ph$ of a diffraction peak (h) of $CoMoO_4$ appearing at $2\theta=26.5°\pm0.1°$ in an X-ray diffraction pattern of a catalytically active component using Cu-K$\alpha$ rays, to be in a range of 0.4 or more and 2.0 or less.

Patent Literature 3 describes that catalyst performance such as catalytic activity and selectivity can be improved by controlling crystallinity $T$ in a range of $2\theta=5°$ or more and $90°$ or less to be in a range of 4% or more and 18% or less, as measured by X-ray diffraction analysis of a catalytically active component using Cu-K$\alpha$ rays.

Further, Patent Literature 4 describes that, in an oxide catalyst in which a ratio $Ri=Pa/Pc$ of an intensity $Pa$ of a diffraction peak (a) of a $Bi_{10}Mo_3O_{24}$ phase appearing at $2\theta=27.4°\pm0.2°$ to an intensity $Pc$ of a diffraction peak (c) of a $CoMoO_4$ phase appearing at a position of $2\theta=26.4°\pm0.2°$ is $0.2\leq Ri\leq1.0$, a time-course increase in the activity in a reaction is small, and an unsaturated aldehyde can be generated at a high yield.

On the other hand, further improvement in yield and improvement in catalytic activity are required for subjecting propylene, isobutylene, t-butyl alcohol or butene to a partial oxidation reaction to produce the corresponding unsaturated aldehyde and/or unsaturated carboxylic acid and required for producing a conjugated diene by oxidative dehydrogenation of butenes. For example, the yield of a target product influences an amount of propylene, isobutylene, t-butyl alcohol, or the like required for the production and greatly influences the production cost. The catalytic activity influences a salt bath temperature (reaction temperature) when the target product is produced, and when a catalyst having low activity is used, the salt bath temperature must be increased in order to maintain the yield of the target product. Then, the catalyst is subjected to thermal stress, and the selectivity and the yield are reduced, and thus this may lead to a reduction in the life of the catalyst.

In addition, Patent Literatures 1 to 3 have no description of focusing on and considering the peak intensities at $2\theta=14.1°\pm0.1°$, $25.4°\pm0.1°$, and $28.5°\pm0.1°$ of the X-ray diffraction patterns.

In particular, regarding the life of the catalyst, a relationship between the physical properties of the catalyst or the time-course change of the physical properties and the life of the catalyst has been unclear. When an unsaturated aldehyde, an unsaturated carboxylic acid, or a conjugated diene is produced using a catalyst with a high yield and/or a high selectivity kept, it has not been clear what index should be used for management.

In particular, regarding the method for using propylene, isobutylene, t-butyl alcohol or the like as a raw material to produce a corresponding unsaturated aldehyde or unsaturated carboxylic acid, it is common to fill two or more layers of catalysts with different activities in a heterogeneous catalytic reaction system, for the purpose of reducing the hot spot temperature and improving the stability of the reaction, for means for improving the yield and improving the catalytic activity, for the reason that these reactions are exothermic reactions, and many reports thereon have been made (for example, Patent Literature 5 and the like).

Among them, Patent Literatures 5, 6, and 7 teach that a composition ratio of Bi as a catalytically active component is reduced from a gas inlet side toward a gas outlet side in an axial direction of a reaction tube and this leads to a reduction in energy cost due to a reduction in the salt bath temperature, an improvement in economic productivity due to an increase in the yield of the target product, a reduction in the changing rate of the temperature in the hot spot with respect to the salt bath temperature, an improvement in the reaction stability due to the reduction in the changing rate, and the like, even though there is a difference in the catalyst to be used, reaction conditions, and the like.

Further, Patent Literature 8 teaches that a target product is obtained at a high yield over a long period of time by filling catalysts so that a parameter related to a pore volume of a catalyst filled in two or more layers changes in each layer. However, it is unclear what the relationship is between the parameter related to the pore volume and the improvement in yield, and how the parameter related to the pore volume can be controlled.

Patent Literature 9 teaches that sublimation of molybdenum contained as a catalytically active component and an increase in a pressure loss in a reaction tube caused by the sublimation are prevented by decreasing a composition ratio of Bi and Fe as a catalytically active component from a gas inlet side toward a gas outlet side in an axial direction of the reaction tube, but only discusses long-term stability of the yield and the pressure loss, and teaches no knowledge about the catalyst composition that provides a higher yield and a filling method thereof.

Even when improvements are made by the means described above, further improvements in yield and catalytic activity are required in subjecting propylene, isobutylene, t-butyl alcohol or butene to a partial oxidation reaction to produce the corresponding unsaturated aldehyde and/or unsaturated carboxylic acid and required in producing a conjugated diene by oxidative dehydrogenation of butenes. For example, the yield of a target product influences an amount of propylene, isobutylene, t-butyl alcohol, or butenes required for the production and greatly influences the production cost. The catalytic activity influences a salt bath temperature when the target product is produced, and when a catalyst having low activity is used, the salt bath temperature must be increased in order to maintain the yield of the target product. As a result, the catalyst is subjected to thermal stress, resulting in a decrease in selectivity and yield, and this leads to a deterioration in catalyst life.

Further, in any of the above Patent Literatures, it can be said that there is no description and knowledge about the case where the filling is performed so that the composition ratio of Bi as the catalytically active component is increased from the gas inlet side toward the gas outlet side in the axial direction of the reaction tube, and that there is no knowledge about the physical properties of the catalyst such as XRD with respect to the active component of each catalyst layer in such a filling method.

CITATION LIST

Patent Literature

Patent Literature 1: WO 2016/136882
Patent Literature 2: JP-A-2017-024009
Patent Literature 3: WO 2010/038677
Patent Literature 4: JP-A-2018-140326
Patent Literature 5: WO 2015/008815
Patent Literature 6: WO 2015/008814
Patent Literature 7: WO 2017/010159
Patent Literature 8: WO 2013/059304
Patent Literature 9: JP-A-2001-48817

SUMMARY OF INVENTION

Technical Problem

A first aspect of the present invention proposes a catalyst which is used in a method for using propylene, isobutylene, t-butyl alcohol, or the like as a raw material to produce a corresponding unsaturated aldehyde or unsaturated carboxylic acid, or used in a catalytic gas phase oxidation method for producing 1,3-butadiene from butenes, and which has high catalytic activity and high yield of a target product. The use of the catalyst of the first aspect allows for performing long-term operation of the catalytic gas phase oxidation method safely, stably, and at low cost.

A second aspect of the present invention proposes a method for using propylene, isobutylene, t-butyl alcohol, or the like as a raw material to produce a corresponding unsaturated aldehyde or unsaturated carboxylic acid, or proposes a catalytic gas phase oxidation method for producing 1,3-butadiene from butenes. The production method of the second aspect allows for performing long-term operation of the catalytic gas phase oxidation method safely, stably, and at low cost.

A third aspect of the present invention proposes a method for filling a catalyst which is used in a method for using propylene, isobutylene, t-butyl alcohol, or the like as a raw material to produce a corresponding unsaturated aldehyde or unsaturated carboxylic acid, or a catalytic gas phase oxidation method for producing 1,3-butadiene from butenes, and which has high catalytic activity and high yield of a target product. The use of the method for filling a catalyst of the third aspect allows for performing long-term operation of the catalytic gas phase oxidation method safely, stably, and at low cost.

Solution to Problem

The present inventors have found that a catalyst in which a sum (S) of ratios of peak intensities at $2\theta=14.1°\pm0.1°$, $25.4°\pm0.1°$, and $28.5°\pm0.1°$ to a peak intensity at $2\theta=26.5°\pm0.1°$ in an X-ray diffraction pattern obtained by using $CuK\alpha$ rays as an X-ray source is in a specific range achieves a high yield, and have completed the first aspect of the present invention.

In addition, a time-course deterioration in the selectivity during a catalytic gas phase oxidation may become a problem in related art, and the reason therefor has been unknown. However, the second aspect of the present invention has been achieved by extracting and evaluating the catalyst after the reaction. That is, the present inventors have found for the first time that the fact that a rate of change in a peak intensity at $2\theta=25.3°\pm0.2°$ after the reaction is small leads to prevention of a deterioration in selectivity.

In addition, the present inventors have found that, in a method for filling two or more layers of catalysts having different activities, a high yield is achieved by filling the catalysts so that a composition ratio of Bi as a catalytically active component is increased from a gas inlet side toward a gas outlet side in an axial direction of a reaction tube, or by filling the catalysts so that a certain parameter is satisfied in the X-ray diffraction pattern of each catalyst layer, and have completed the third aspect of the present invention.

That is, the present invention relates to the following 1) to 17).

1)
A catalyst comprising, as an essential component, molybdenum;
bismuth; and
cobalt, wherein
a sum (S) of ratios of peak intensities expressed by the following formula in an X-ray diffraction pattern obtained by using $CuK\alpha$ rays as an X-ray source is 42 or more and 113 or less.

$$S=\{(\text{peak intensity at } 2\theta=14.1°\pm0.1°)+(\text{peak intensity at } 2\theta=25.4°\pm0.1°)+(\text{peak intensity at } 2\theta=28.5°\pm0.1°)\}/(\text{peak intensity at } 2\theta=26.5°\pm0.1°)\times100$$

2)
The catalyst according to 1), wherein a ratio (S4) of a peak intensity expressed by the following formula is 2 or more and 16 or less.

$$S4=(\text{peak intensity at } 2\theta=27.4°\pm0.1°)/(\text{peak intensity at } 2\theta=26.5°\pm0.1°)\times100$$

3)
The catalyst according to 1) or 2), wherein a composition of a catalytically active component is represented by the following formula (I-1):

$$Mo_{a1}Bi_{b1}Ni_{c1}Co_{d1}Fe_{e1}X_{f1}Y_{g1}Z_{h1}O_{i1} \tag{I-1}$$

(in the formula, Mo, Bi, Ni, Co and Fe represent molybdenum, bismuth, nickel, cobalt and iron, respectively; X is at least one element selected from tungsten, antimony, tin, zinc, chromium, manganese, magnesium, silica, aluminum, cerium and titanium; Y is at least one element selected from sodium, potassium, cesium, rubidium, and thallium; Z belongs to the 1st to 16th groups in the periodic table and means at least one element selected from elements other than the above Mo, Bi, Ni, Co, Fe, X, and Y; a1, b1, c1, d1, e1, f1, g1, h1, and i1 represent the number of atoms of molybdenum, bismuth, nickel, cobalt, iron, X, Y, Z, and oxygen, respectively; when a1=12, $0<b1\leq7$, $0\leq c1\leq10$, $0<d1\leq10$, $0<c1+d1\leq20$, $0\leq e1\leq5$, $0\leq f1\leq2$, $0\leq g1\leq3$, $0\leq h1\leq5$, and i1 is a value determined by an oxidation state of each element).

4)
The catalyst according to any one of 1) to 3), which is a catalyst in which a catalytically active component is carried on an inert carrier.

5)

The catalyst according to 4), wherein the inert carrier is silica, alumina, or a combination thereof.

6)

The catalyst according to any one of 1) to 5), which is a catalyst for producing at least one of an unsaturated aldehyde compound, an unsaturated carboxylic acid compound, and a conjugated diene.

7)

A method for producing at least one of an unsaturated aldehyde compound, an unsaturated carboxylic acid compound, and a conjugated diene using the catalyst according to any one of 1) to 6).

8)

The method according to 7), wherein the unsaturated aldehyde compound is acrolein, the unsaturated carboxylic acid compound is acrylic acid, and the conjugated diene is 1,3-butadiene.

9)

An unsaturated aldehyde compound, an unsaturated carboxylic acid compound, or a conjugated diene produced using the catalyst according to any one of 1) to 6).

10)

A method for filling a catalyst, the method comprising:
filling a composite metal oxide catalyst containing molybdenum, bismuth, and cobalt as an essential component such that two or more layers are stacked in a tube axis direction for multi-layer filling,
wherein a composition of the composite metal oxide catalyst contained in one catalyst layer is different from a composition of the composite metal oxide catalyst contained in at least one of the other catalyst layers,
a ratio of a component amount of bismuth to a component amount of molybdenum in a catalyst layer closest to a gas inlet side of a tube axis is smaller than a ratio of a component amount of bismuth to a component amount of molybdenum in a catalyst layer closest to a gas outlet side of the tube axis, and
in any of two catalyst layers adjacent to each other, the catalysts are filled such that a ratio of the component amount of bismuth to the component amount of molybdenum in a catalyst layer on the gas inlet side of the tube axis is equal to or smaller than a ratio of the component amount of bismuth to the component amount of molybdenum in a catalyst layer on the gas outlet side of the tube axis.

11)

A method for filling a catalyst, the method comprising:
filling a composite metal oxide catalyst containing molybdenum, bismuth, and cobalt as an essential component such that two or more layers are stacked in a tube axis direction for multi-layer filling,
wherein the catalysts are filled such that, with respect to a sum (S) of ratios of peak intensities of a catalyst contained in one catalyst layer, which is expressed by the following formula in an X-ray diffraction pattern obtained by using CuKα rays as an X-ray source, the sum (S) of ratios of peak intensities of a catalyst contained in a catalyst layer closest to a gas outlet side of a tube axis is smaller than the sum (S) of ratios of peak intensities of a catalyst contained in a catalyst layer closest to a gas inlet side of the tube axis.

$$S=\{(\text{peak intensity at } 2\theta=14.1°\pm0.1°)+(\text{peak intensity at } 2\theta=25.4°\pm0.1°)+(\text{peak intensity at } 2\theta=28.5°\pm0.1°)\}/(\text{peak intensity at } 2\theta=26.5°\pm0.1°)\times100$$

12)

The method for filling a catalyst according to 10) or 11), wherein the catalysts are filled such that, with respect to a ratio (S1) of a peak intensity of the catalyst contained in one catalyst layer, which is expressed by the following formula in the X-ray diffraction pattern obtained by using CuKα rays as an X-ray source, the ratio (S1) of a peak intensity of a catalyst contained in the catalyst layer closest to the gas outlet side of the tube axis is smaller than the ratio (S1) of a peak intensity of a catalyst contained in the catalyst layer closest to the gas inlet side of the tube axis.

$$S1=(\text{peak intensity at } 2\theta=14.1°\pm0.1°)/(\text{peak intensity at } 2\theta=26.5°\pm0.1°)\times100$$

13)

The method for filling a catalyst according to any one of 10) to 12), wherein the catalysts are filled such that, with respect to a ratio (S2) of a peak intensity of the catalyst contained in one catalyst layer, which is expressed by the following formula in the X-ray diffraction pattern obtained by using CuKα rays as an X-ray source, the ratio (S2) of a peak intensity of a catalyst contained in the catalyst layer closest to the gas outlet side of the tube axis is smaller than the ratio (S2) of a peak intensity of a catalyst contained in the catalyst layer closest to the gas inlet side of the tube axis.

$$S2=(\text{peak intensity at } 2\theta=25.4°\pm0.1°)/(\text{peak intensity at } 2\theta=26.5°\pm0.1°)\times100$$

14)

The method for filling a catalyst according to any one of 10) to 13), wherein the catalysts are filled such that, with respect to a ratio (S3) of a peak intensity of the catalyst contained in one catalyst layer, which is expressed by the following formula in the X-ray diffraction pattern obtained by using CuKα rays as an X-ray source, the ratio (S3) of a peak intensity of a catalyst contained in the catalyst layer closest to the gas outlet side of the tube axis is smaller than the ratio (S3) of a peak intensity of a catalyst contained in the catalyst layer closest to the gas inlet side of the tube axis.

$$S3=(\text{peak intensity at } 2\theta=28.5°\pm0.1°)/(\text{peak intensity at } 2\theta=26.5°\pm0.1°)\times100$$

15)

The method for filling a catalyst according to any one of 10) to 14), wherein the catalyst to be filled is a catalyst for a catalytic gas phase oxidation and for producing a corresponding unsaturated aldehyde or unsaturated carboxylic acid using propylene, isobutylene, or t-butyl alcohol as a raw material, or a catalyst for a catalytic gas phase oxidation and for producing 1,3-butadiene from butenes.

16)

A method for producing at least one of an unsaturated aldehyde compound, an unsaturated carboxylic acid compound, and a conjugated diene, using a reaction tube filled with a catalyst by the method for filling a catalyst according to any one of 10) to 15).

17)

The method according to 16), wherein the unsaturated aldehyde compound is acrolein, the unsaturated carboxylic acid compound is acrylic acid, and the conjugated diene is 1,3-butadiene.

Advantageous Effects of Invention

The catalyst of the first aspect of the present invention is very effective in improving the catalytic activity and the yield in the catalytic gas phase oxidation or the catalytic gas-phase oxidation dehydrogenation, and is particularly useful for using propylene, isobutylene, t-butyl alcohol, or the like as a raw material to produce a corresponding unsaturated aldehyde or unsaturated carboxylic acid.

The production method of the second aspect of the present invention is very effective in maintaining a high selectivity in the catalytic gas phase oxidation or the catalytic gas-phase oxidation dehydrogenation and in improving the yield. In particular, it is useful for using propylene, isobutylene, t-butyl alcohol, or the like as a raw material to produce a corresponding unsaturated aldehyde or unsaturated carboxylic acid.

The method for filling a catalyst of the third aspect of the present invention is very effective in improving the catalytic activity and the yield in the catalytic gas phase oxidation or the catalytic gas-phase oxidation dehydrogenation, and is particularly useful in that the yield of the target product can be improved in using propylene, isobutylene, t-butyl alcohol, or the like as a raw material to produce a corresponding unsaturated aldehyde or unsaturated carboxylic acid.

DESCRIPTION OF EMBODIMENTS

Figure 1:
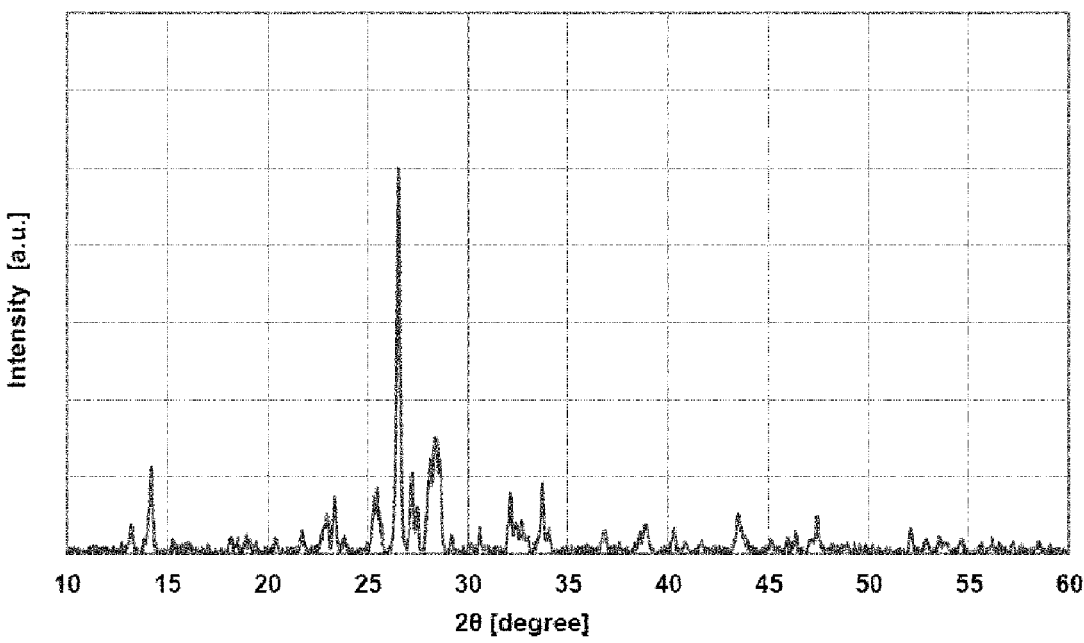
FIG. 1 is a graph representing an X-ray diffraction pattern of a catalyst (catalyst I-3) in Example I-3.

The present invention is described in detail below. In the present specification, a catalytic gas phase oxidation and a catalytic gas phase oxidation dehydrogenation may be collectively referred to simply as an oxidation reaction.

[[First Aspect]]

[Sum (S) of Ratios of Peak Intensities in X-Ray Diffraction Pattern]

A catalyst of a first aspect of the present invention is characterized in a sum (S) of ratios of peak intensities at $2\theta=14.1°\pm0.1°$, $25.4°\pm0.1°$, and $28.5°\pm0.1°$ to a peak intensity at $2\theta=26.5°\pm0.1°$ in an X-ray diffraction pattern obtained by using CuKα rays as an X-ray source. The peak intensity at $2\theta=26.5°\pm0.1°$ means a local maximum value of a peak observed in a range of $2\theta=26.5°\pm0.1°$, and the nature of the peak intensity indicates a peak height of a crystal phase of β-CoMoO₄. Similarly, the peak intensities at $2\theta=14.1°\pm0.1°$, $25.4°\pm0.1°$, and $28.5°\pm0.1°$ indicate a peak height of a crystal phase of α-CoMoO₄. That is, the nature of the first aspect is that the catalyst exhibits a high yield when the peak intensity of the crystal phase of α-CoMoO₄ observed at $2\theta=14.1°\pm0.1°$, $25.4°\pm0.1°$, and $28.5°\pm0.1°$ with respect to the peak intensity of the crystal phase of β-CoMoO₄ observed at $2\theta=26.5°\pm0.1°$ is within a certain range. As will be described later, the peak intensity of the crystal phase of α-CoMoO₄, more specifically, the peak intensity of each crystal plane changes depending on the composition and the production method of the catalyst, and thus the sum of the peak intensities of specific crystal planes among α-CoMoO₄ is particularly important. The nature of the first aspect is finding a relationship between a parameter S and the performance. More specifically, the sum (S) of ratios of peak intensities is expressed by the following formula.

$$\text{Sum } (S) \text{ of ratios of peak intensities} = \{(\text{peak intensity at } 2\theta=14.1°\pm0.1°) + (\text{peak intensity at } 2\theta=25.4°\pm0.1°) + (\text{peak intensity at } 2\theta=28.5°\pm0.1°)\}/(\text{peak intensity at } 2\theta=26.5°\pm0.1°) \times 100$$

As a relationship found by the inventors, the selectivity of the catalytic reaction is increased and the activity of the catalytic reaction is decreased with an increase in the parameter S of the first aspect. That is, the present inventors have found that the yield has a local maximum value with respect to the parameter S of the first aspect, and have filed the first aspect of the present invention. The range of the parameter S is 42 or more and 113 or less. The upper limit of the parameter S is 110, 105, 100, 95, 90, 85, 80, or 75 in more preferred order, and most preferably 70, and the lower limit of the parameter S is 44, 46, 48, 50, 52, 53, 54, 56, 58, 60, 62, 64, or 65 in more preferred order, and most preferably 66. That is, a preferred range of the sum (S) of ratios of peak intensities is set by the upper and lower limits, for example, 44 or more and 110 or less, and most preferably 66 or more and 70 or less.

Examples of a method of measuring an X-ray diffraction angle $(2\theta)$ include measuring the X-ray diffraction angle $(2\theta)$ under conditions of X-ray CuKα rays $(\lambda=0.154 \text{ nm})$, an output of 40 kV, 30 mA, a measurement range of 10° to 60°, and a measurement speed of 10° per minute by using Ultima IV manufactured by Rigaku Corporation, but the method is not limited thereto as long as the method does not depart from the measurement principle. For the sum (S) of ratios of peak intensities calculated in the first aspect, the calculation is performed after the background and halo patterns described in Patent Literature 3 have been eliminated from the X-ray diffraction pattern before the calculation. When each of the peaks does not have a clear local maximum value in the corresponding range of 2θ or does not have a peak shape, or when it is not determined that the peak is a clear peak due to too much noise, or when the peak has a local minimum value in the range of 2θ for calculating the local maximum value of the peak, the peak intensity is assumed to be 0 in the first aspect.

Further, the catalyst of the first aspect has an optimum range for individual peak intensities with respect to the peak intensity at $2\theta=26.5°\pm0.1°$ as shown below.

The catalyst of the first aspect has an optimum range for a peak intensity ratio S1 expressed by the following formula, and the lower limit thereof is 5, 10, 14, 16, 18, or 20 in preferred order, and most preferably 21, and the upper limit thereof is 42, 40, 36, 32, or 30 in preferred order, and most preferably 28. That is, the most preferred range of S1 is 21 or more and 28 or less.

$$S1 = (\text{peak intensity at } 2\theta=14.1°\pm0.1°)/(\text{peak intensity at } 2\theta=26.5°\pm0.1°) \times 100$$

The catalyst of the first aspect has an optimal range for a peak intensity ratio S2 expressed by the following formula, and the lower limit thereof is 2, 4, 6, 8, 10, 12, or 14 in preferred order, and most preferably 15, and the upper limit thereof is 20, and most preferably 18. That is, the most preferred range of S2 is 15 or more and 18 or less.

$$S2 = (\text{peak intensity at } 2\theta=25.4°\pm0.1°)/(\text{peak intensity at } 2\theta=26.5°\pm0.1°) \times 100$$

The catalyst of the first aspect has an optimum range for a peak intensity ratio S3 expressed by the following formula, and the lower limit thereof is 10, 15, 20, 22, 24, or 26 in preferred order, and most preferably 27, and the upper limit thereof is 44, 42, 40, 38, 36, 34, or 32 in preferred order, and most preferably 31. That is, the most preferred range of S3 is 27 or more and 31 or less.

$$S3 = (\text{peak intensity at } 2\theta=28.5°\pm0.1°)/(\text{peak intensity at } 2\theta=26.5°\pm0.1°)\times100$$

The catalyst of the first aspect preferably has a peak at $2\theta=27.4°\pm0.1°$ in addition to the above peak in an X-ray diffraction pattern obtained by using CuK$\alpha$ rays as an X-ray source. When the peak intensity is within a specific range, the catalyst is more preferable. When the peak intensity is defined as S4, the lower limit thereof is 2, 4, 6, 8 in preferred order, and most preferably 9, and the upper limit thereof is 16, 15, or 14 in preferred order, and most preferably 13. That is, the most preferred range of S4 is 9 or more and 13 or less.

$$S4 = (\text{peak intensity at } 2\theta=27.4°\pm0.1°)/(\text{peak intensity at } 2\theta=26.5°\pm0.1°)\times100$$

[Catalyst Composition]

A catalytically active component contained in the catalyst of the first aspect preferably has a composition represented by the following formula (I-1).

$$Mo_{a1}Bi_{b1}Ni_{c1}Co_{d1}Fe_{e1}X_{f1}Y_{g1}Z_{h1}O_{i1} \tag{I-1}$$

(in the formula, Mo, Bi, Ni, Co and Fe represent molybdenum, bismuth, nickel, cobalt and iron, respectively; X is at least one element selected from tungsten, antimony, tin, zinc, chromium, manganese, magnesium, silicon, aluminum, cerium and titanium; Y is at least one element selected from sodium, potassium, cesium, rubidium, and thallium; Z belongs to the 1st to 16th groups in the periodic table and means at least one element selected from elements other than the above Mo, Bi, Ni, Co, Fe, X, and Y; $a1$, $b1$, $c1$, $d1$, $e1$, $f1$, $g1$, $h1$, and $i1$ represent the number of atoms of molybdenum, bismuth, nickel, cobalt, iron, X, Y, Z, and oxygen, respectively; when $a1=12$, $0<b1\leq7$, $0\leq c1\leq10$, $0<d1\leq10$, $0<c1+d1\leq20$, $0\leq e1\leq5$, $0\leq g1\leq2$, $0\leq f1\leq3$, $0\leq h1\leq5$, and $i1$ is a value determined by an oxidation state of each element).

In the formula (I-1), the preferred ranges of $b1$ to $i1$ are as follows.

The lower limit of $b1$ is 0.2, 0.5, 0.7, or 0.8 in preferred order, and most preferably 0.9, and the upper limit of $b1$ is 5, 3, 2, 1.6, 1.4, or 1.2 in preferred order, and most preferably 1.1. That is, the most preferred range of $b1$ is $0.9\leq b1\leq1.1$.

The lower limit of $c1$ is 1, 2, 2.5, 2.8, or 3.0 in preferred order, and most preferably 3.1, and the upper limit of $c1$ is 5, 4, 3.8, 3.6, or 3.4 in preferred order, and most preferably 3.2. That is, the most preferred range of $c1$ is $3.1\leq c1\leq3.2$.

The lower limit of $d1$ is 3, 4, 5, 5.3, 5.5, or 5.7 in preferred order, and most preferably 5.8, and the upper limit of $d1$ is 8, 7, 6.5, 6.3, or 6.1 in preferred order, and most preferably 6.0. That is, the most preferred range of $d1$ is $5.8\leq d1\leq6.0$.

The lower limit of $e1$ is 0.5, 1, 1.2, or 1.4 in preferred order, and most preferably 1.5, and the upper limit of $e1$ is 4, 3, 2.5, 2, or 1.8 in preferred order, and most preferably 1.7. That is, the most preferred range of $e1$ is $1.5\leq e1\leq1.7$.

The upper limit of $f1$ is 8, 7, 6, or 5 in preferred order. That is, the most preferred range of $f1$ is $0\leq f1\leq5$.

The lower limit of $g1$ is 0, 0.02, 0.04, or 0.06 in preferred order, and most preferably 0.07, and the upper limit of $g1$ is 1.5, 1, 0.5, 0.2, or 0.15 in preferred order, and most preferably 0.10. That is, the most preferred range of $g1$ is $0.07\leq g1\leq0.10$.

The upper limit of $h1$ is 8, 7, 6, or 5 in preferred order. That is, the most preferred range of $h1$ is $0\leq h1\leq5$.

It is preferable that two or less types of Y are contained, and one type is particularly preferred. In addition, it is particularly preferable that $f1$ and $h1$ are 0.

[Carrying]

The catalyst in which a preliminary calcined powder subjected to preliminary calcination after the preparation of the catalytically active component is carried on the inert carrier is particularly excellent as the catalyst of the first aspect.

As the material of the inert carrier, known materials such as alumina, silica, titania, zirconia, niobia, silica alumina, silicon carbide, carbides, and mixtures thereof can be used. Further, the particle size, water absorption rate, mechanical strength, crystallinity of each crystal phase, mixing ratio, etc. are not limited, and an appropriate range of these should be selected in consideration of the final catalyst performance, molding properties, production efficiency, etc. The mixing ratio of the carrier and the preliminarily calcined powder is calculated as the active mass ratio according to the following equation based on the charged mass of each raw material.

$$\text{Active mass ratio (mass \%)} = (\text{mass of preliminary calcined powder used for molding})/\{(\text{mass of preliminary calcined powder used for molding})+(\text{mass of carrier used for molding})\}\times100$$

The upper limit of the active mass ratio is preferably 80 mass %, and more preferably 60 mass %.

The lower limit is preferably 20 mass %, and more preferably 30 mass %. That is, the most preferred range of the active mass ratio is 30 mass % or more and 60 mass % or less.

As the inert carrier, silica and/or alumina is preferable, and a mixture of silica and alumina is particularly preferable.

For the carrying, it is preferred to use a binder. Specific examples of the binder which can be used include water, ethanol, methanol, propanol, a polyhydric alcohol, polyvinyl alcohol as a polymer-based binder, and a silica sol aqueous solution as an inorganic binder; ethanol, methanol, propanol, and a polyhydric alcohol are preferred; a diol such as ethylene glycol and a triol such as glycerin is preferred; and an aqueous solution having a concentration of glycerin of 5 mass % or more is preferred. Using an appropriate amount of a glycerin aqueous solution allows for obtaining a high-performance catalyst having good molding properties and high mechanical strength. The amount of these binders used is usually 2 to 60 parts by mass with respect to 100 parts by mass of the preliminarily calcined powder. The amount of glycerin aqueous solution is preferably 10 to 30 parts by mass. The binder and the preliminarily calcined powder may be alternately or simultaneously supplied to a molding machine on the occasion of carrying.

For the means for controlling the value of S, the control can be performed by changing each condition in each production process described later, and examples thereof include (I) a method of changing a catalyst composition, (II) a method of changing a calcination condition, (III) a method of changing a temperature decrease condition after calcination, (IV) a method of controlling a catalyst and a precursor thereof such that the catalyst and the precursor are not subjected to mechanical strength in all the steps of the production of the catalyst, (V) a method of using a raw material having high purity, other methods (VI) to (VIII), and a method of combining (I) to (VIII). The details of the methods (VI) to (VIII) will be described later.

Regarding the method (I), in the composition formula (I-1), the upper limit of $e1/b1$ is 1.90, and preferably 1.80; the lower limit of $e1/b1$ is 0.10, 0.50, 1.00, 1.40, or 1.50 in preferred order; the upper limit of $d1/b1$ is 9.0, 8.0, 7.0, or 6.0 in preferred order; the lower limit of $d1/b1$ is 2.0, 3.0, 4.0, 5.0, or 5.5 in preferred order; the upper limit of $c1/e1$ is 4.0, 3.0, or 2.5 in preferred order; the lower limit of $c1/e1$ is 1.5, 1.7, or 1.9 in preferred order; the upper limit of $c1/d1$ is 2.0, 1.0, or 0.8 in preferred order; the lower limit of $c1/d1$ is 0.4 or 0.5 in preferred order; the upper limit of $g1/d1$ is 0.10, 0.05, 0.04, or 0.03 in preferred order; the lower limit of $g1/d1$ is 0.01; the upper limit of $g1/c1$ is 0.041 or 0.039 in preferred order; and the lower limit of $g1/c1$ is 0.017, 0.019 or 0.021 in preferred order.

Regarding the method (II), a temperature in preliminary calcination and main calcination as described later and in both of them is 200° C. or more and 600° C. or less, preferably 300° C. or more and 550° C. or less, and more preferably 460° C. or more and 550° C. or less, and a time in preliminary calcination and main calcination as described later and in both of them is 0.5 hours or more, preferably 1 hour or more and 40 hours or less, more preferably 2 hours or more and 15 hours or less, and most preferably 2 hours or more and 9 hours or less. An atmosphere in preliminary calcination and main calcination as described later and in both of them has 10 vol % or more and 40 vol % or less of the oxygen concentration, preferably 15 vol % or more and 30 vol % or less, and most preferably the atmosphere is an air atmosphere.

Regarding the method (III), in the preliminary calcination and the main calcination as described later and in both of them, a rate of decrease (rate of temperature decrease) of the temperature of a catalyst surface from the maximum temperature (preliminary calcination temperature or main calcination temperature) reached in the calcination step to the room temperature is 1° C./min or more and 200° C./min or less, preferably 5° C./min or more and 150° C./min or less, more preferably 10° C./min or more and 120° C./min or less, and most preferably 50° C./min or more and 100° C./min or less. A temperature decrease method industrially typically taken for achieving the above-described range of the rate of temperature decrease described above, for example, a method of exposing a catalyst taken out from a calcination furnace to an inert atmosphere or a mist of an inert solvent, and a method of rapidly moving a catalyst into a room sufficiently cooled in advance are all included in the first aspect.

The method (IV) is a method of controlling a catalyst precursor to be described later and/or granules formed in each step such that the catalyst precursor and/or granules are not subjected to a mechanical impact, a shear stress, and the like, and the preferred range of the mechanical impact, shear stress, and the like is controlled to 100 kgf or less, preferably 50 kgf or less, more preferably 20 kgf or less, still more preferably 10 kgf or less, and most preferably 5 kgf or less.

The method (V) is not limited as long as the method (V) is a method using a high purity raw material at the level of reagent, and for example, the content of sulfur and a compound thereof, lithium, halogen and a compound thereof, and lead in the raw material is 10000 ppm by weight or less, preferably 1000 ppm by weight or less, more preferably 100 ppm by weight, and most preferably 10 ppm by weight or less.

The method (VI), as described later, is, for example, a method in which a catalyst precursor is once obtained as granules and the granules are molded. Obtaining the catalyst precursor in the form of granules allows for producing the catalyst such that each component of the catalyst can be more uniform.

The method (VII) is a method of controlling a time during which a cobalt raw material and a nickel raw material are mixed, reacted, slurried, and retained in a mixing pot to be as short as possible in the step of preparing the catalyst to be described later, and more specifically, is a method of shortening the retention time in a state in which a metal salt raw material excluding molybdenum and alkali metal is not in the mixing pot and the cobalt raw material and the nickel raw material are present in the mixing pot, or a method of shortening the retention time in a state in which the cobalt raw material and the nickel raw material are present in the mixing pot when a pH in the mixing pot falls within a specific range. The retention time is preferably 24 hours, more preferably 1 hour, still more preferably 30 minutes, and most preferably 10 minutes. The range of pH is 1 or more and 14 or less, preferably 2 or more and 10 or less, more preferably 2 or more and 8 or less, and most preferably 3 or more and 7 or less. The same applies to an iron raw material and a bismuth raw material, a molybdenum raw material, and a bismuth raw material.

The method (VIII) is a method in which each raw material is undividedly charged at once in the preparing step, or a method in which the concentration of nitric acid in a mixed solution is decreased, in the step of preparing a catalyst to be described later. The method of charging each raw material at once means charging a next raw material after charging all the necessary amount of a raw material. Regarding the concentration of nitric acid in the mixed solution, the concentration of nitric acid ions in terms of mass % in the prepared solution when the preparation is completed and before the process proceeds to the next step is preferably 40 mass % or less, more preferably 35 mass % or less, still more preferably 30 mass % or less, and most preferably 25 mass % or less.

[Method for Producing Catalyst]

A starting raw material for each element constituting the catalyst of the first aspect and the preliminary calcined powder thereof is not limited. For example, as a raw material of a molybdenum component, molybdenum oxides such as molybdenum trioxide, molybdic acid or salts thereof such as molybdate, ammonium paramolybdate and ammonium metamolybdate, and heteropolyacids containing molybdenum or salts thereof such as phosphomolybdic acid and silicate molybdic acid, can be used.

As a raw material of a bismuth component, bismuth salts such as bismuth nitrate, bismuth carbonate, bismuth sulfate, and bismuth acetate, bismuth trioxide, metal bismuth and the like can be used. These raw materials can be used as solids or as an aqueous solution, a nitric acid solution, or a slurry of bismuth compounds generated from those aqueous solutions, and the nitrate, a solution thereof, or a slurry obtained from the solution is preferably used.

As a starting raw material for other constituent elements, ammonium salt, nitrate, nitrite, carbonate, subcarbonate, acetate, chloride, inorganic acid, inorganic acid salt, heteropolyacid, heteropolyacid salt, sulfate, hydroxide, organic acid salt, and oxide of metallic elements commonly used in this type of catalyst may be used, or a mixture thereof may be used in combination. Ammonium salts and nitrates are preferably used.

A compound containing these active components may be used alone or in combination of two or more. A slurry liquid can be obtained by uniformly mixing each compound containing an active component and water. The amount of water to be used in the slurry liquid is not limited as long as the total amount of the compound to be used can be completely dissolved or uniformly mixed. The amount of water to be used may be appropriately determined in consideration of the drying method and the drying conditions. Usually, the amount of water to be used is 100 parts by mass or more and 2000 parts by mass or less with respect to 100 parts by mass of the total mass of the compound for preparing a slurry. The amount of water may be large, but too large amount of water causes many disadvantages such as an increase in the energy cost of the drying step and a possible failure to completely dry.

The slurry liquid of the source compound of the above each component element is preferably prepared by (a) a method of mixing each of the above source compounds at once, (b) a method of mixing the above source compounds at once and then performing aging, (c) a method of mixing the above source compounds stepwise, (d) a method of repeating mixing step and aging step stepwise, and (e) a method combining (a) to (d). Here, the above aging means "an operation in which industrial raw materials or semi-finished products are processed under specific conditions such as a certain period of time and a certain temperature to conduct acquisition or improvement of the required physical properties and chemical properties, or proceeding of a predetermined reaction". In the first aspect, the above certain period of time means a range of 5 minutes or longer and 24 hours or shorter, and the above certain temperature means a range from room temperature to a point equal to or lower than a boiling point of an aqueous solution or an aqueous dispersion liquid. Among these, in terms of the activity and yield of the finally obtained catalyst, preferred is the (c) method of mixing the above source compounds stepwise, more preferred is a method in which each raw material to be mixed with a mother liquid stepwise is completely dissolved to be a solution, and most preferred is a method of mixing various mixed solutions of alkali metal solution and nitrate with a mother liquid in which the raw material of the molybdenum is a mixed solution or slurry. However, it is not always necessary to mix all the elements constituting the catalyst in this step, and some elements or some amounts thereof may be added in the subsequent steps.

In the first aspect, the shape of the stirring blade of the stirrer used in mixing the essential active components is not limited. Any stirring blade such as a propeller blade, a turbine blade, a paddle blade, an inclined paddle blade, a screw blade, an anchor blade, a ribbon blade, a large lattice blade can be used in one stage or in two or more stages of which blades are the same or different types in the vertical direction. In addition, a baffle (obstruction plate) may be installed in the reaction tank if necessary.

Then, the slurry liquid thus-obtained is dried. The drying method is not limited so long as the slurry liquid can be completely dried by the method, but examples thereof include drum drying, freeze drying, spray drying and evaporation drying. Among these, spray drying, which allows the slurry liquid to be dried into a powder or granule within a short period of time, is particularly preferred in the first aspect. The temperature of the drying with spray drying varies depending on the concentration of the slurry liquid, the liquid sending speed, or the like. Typically, the temperature at the outlet of a drying machine is 70° C. or higher and 150° C. or lower.

Subjecting the catalyst precursor obtained as described above to preliminary calcination, molding, and then main calcination allows for controlling and holding the obtained shape, and obtaining a catalyst having particularly excellent mechanical strength for industrial use, and the catalyst can exhibit stable catalyst performance.

As for the molding, either a carrying shaping in which the preliminarily calcined powder is carried on a carrier such as silica or a non-carrying shaping in which no carrier is used can be adopted. Specific examples of the molding method include tablet molding, press molding, extrusion molding and granulation molding. As the shape of the molded product, for example, a columnar shape, a ring shape, a spherical shape or the like can be appropriately selected in consideration of operating conditions. Preferred is a carried catalyst in which a catalytically active component is carried on a spherical carrier, particularly an inert carrier such as silica or alumina and in which the average particle size is 3.0 mm or more and 10.0 mm or less, and preferably 3.0 mm or more and 8.0 mm or less. As for the carrying method, a tumbling granulation method, a method using a centrifugal flow coating apparatus, a wash coating method, and the like are widely known. The method is not limited as long as the preliminarily calcined powder can be uniformly carried on the carrier, but the tumbling granulation method is preferred in consideration of the production efficiency of the catalyst and the like. Specifically, the tumbling granulation method is a method in which using a device that has a flat or uneven disk at the bottom of a fixed cylindrical container, a carrier charged into the container is vigorously agitated by means of a repeat of rotation motion and revolution motion of the carrier itself by rotating the disk at a high speed, and then the preliminarily calcined powder is added into the container to carry the powder component on the carrier.

On the occasion of carrying, it is preferred to use a binder. Specific examples of the binder which can be used include water, ethanol, methanol, propanol, a polyhydric alcohol, polyvinyl alcohol as a polymer-based binder and a silica sol aqueous solution as an inorganic binder; ethanol, methanol, propanol, and a polyhydric alcohol are preferred; a diol such as ethylene glycol and a triol such as glycerin is more preferred; and an aqueous solution of glycerin having a concentration of 5 mass % or more is still more preferred. Using an appropriate amount of the glycerin aqueous solution allows for obtaining a high-performance catalyst having good molding properties and high mechanical strength. The amount of these binders to be used is usually 2 to 60 parts by mass with respect to 100 parts by mass of the preliminarily calcined powder, and the amount of the glycerin aqueous solution is preferably 15 to 50 parts by mass. The binder and the preliminarily calcined powder may be alternately supplied to a molding machine or simultaneously supplied to the molding machine on the occasion of the carrying. Further, on the occasion of molding, a small amount of known additives such as graphite and talc may be added. None of a molding aid, a pore-forming agent and a carrier added in the molding is considered as the constituent element of the active component in the first aspect, regardless of whether the molding aid, the pore-forming agent and the carrier have the activity in the sense of converting the raw material into some other product.

The preliminary calcination method, the preliminary calcination conditions, the main calcination method, and the main calcination conditions are not limited, but known treatment methods and conditions can be applied. The preliminary calcination or the main calcination is usually carried out at 200° C. or higher and 600° C. or lower, and preferably 300° C. or higher and 550° C. or lower, for 0.5 hours or longer, and preferably 1 hour or longer and 40 hours or shorter under the conditions that an oxygen-containing gas such as air or an inert gas flow. Here, the inert gas refers to a gas that does not reduce the reaction activity of the catalyst, and specific examples thereof include nitrogen, carbon dioxide, helium and argon. The optimum conditions for the main calcination vary depending on the reaction conditions when an unsaturated aldehyde and/or an unsaturated carboxylic acid are produced using a catalyst, and changing the process parameters of the main calcination step, that is, the oxygen content in the atmosphere, the maximum temperature reached and the calcination time falls within the scope of the first aspect, because the changing is well-known for the skilled person. The main calcination step shall be carried out after the above preliminary calcination step, and the maximum temperature reached (main calcination temperature) in the main calcination step shall be higher than the maximum temperature reached (preliminary calcination temperature) in the above preliminary calcination step. The technique of the calcination includes but not limited to a fluidized bed, rotary kiln, muffle furnace, and tunnel firing furnace, and should be selected within an appropriate range in consideration of the final catalyst performance, mechanical strength, molding properties, production efficiency and the like.

The catalyst of the first aspect is preferably used as a catalyst for producing an unsaturated aldehyde compound, an unsaturated carboxylic acid compound, or a conjugated diene compound, is more preferably used as a catalyst for producing an unsaturated aldehyde compound, and is particularly preferably used as a catalyst for producing acrolein from propylene. In a process of an exothermic reaction such as production of an unsaturated aldehyde compound, an unsaturated carboxylic acid compound, or a conjugated diene compound, it is known to those skilled in the art that different catalyst types are filled in multiple layers so that the activity is increased from an inlet side of a reaction tube toward an outlet side of the reaction tube, for the purpose of preventing deterioration of the catalyst itself due to heat generated by the reaction in an actual plant. The catalyst of the first aspect can be used on either an inlet side of the reaction tube, an outlet side of the reaction tube, or the middle catalyst layer. For example, the catalyst of the first aspect is most preferably used on the most outlet side of the reaction tube, that is, the catalyst of the first aspect is used as the most active catalyst among all catalyst layers in the reaction tube. For the multilayer filling, two-layer or three-layer filling is particularly preferred.

[Catalyst in Second Stage]

When the catalyst of the first aspect is used as a catalyst in a first stage, that is, a catalyst for producing an unsaturated aldehyde compound, an unsaturated carboxylic acid compound can be obtained by performing a second-stage oxidation reaction.

In this case, the catalyst of the first aspect can also be used as a catalyst in a second stage, but a catalyst containing a catalytically active component represented by the following formula (I-2) is preferred.

$$Mo_{12}V_{a2}W_{b2}Cu_{c2}Sb_{d2}X2_{e2}Y2_{f2}Z2_{g2}O_{h2} \qquad \text{(I-2)}$$

(In the formula, Mo, V, W, Cu, Sb and O represent molybdenum, vanadium, tungsten, copper, antimony and oxygen, respectively; X2 represents at least one element selected from the group consisting of an alkali metal and thallium; Y2 represents at least one element selected from the group consisting of magnesium, calcium, strontium, barium and zinc; and Z2 represents at least one element selected from the group consisting of niobium, cerium, tin, chromium, manganese, iron, cobalt, samarium, germanium, titanium and arsenic. a2, b2, c2, d2, e2, f2, g2 and h2 represent the atomic proportion of each element, and with respect to molybdenum atom 12, a2 satisfies $0<a2\leq10$, b2 satisfies $0\leq b2\leq10$, c2 satisfies $0<c2\leq6$, d2 satisfies $0<d2\leq10$, e2 satisfies $0\leq e2\leq0.5$, f2 satisfies $0\leq f2\leq1$, and g2 satisfies $0\leq g2<6$. Further, h2 is the number of oxygen atoms required to satisfy the atomic value of each component.)

In the production of a catalyst containing the catalytically active component represented by the above formula (I-2), a method widely known as a method for preparing this kind of a catalyst, for example, an oxide catalyst or a catalyst having a heteropolyacid or a salt structure thereof, can be adopted. The raw materials that can be used in producing the catalyst are not limited, and various materials can be used. For example, molybdenum oxides such as molybdenum trioxide, molybdic acid or salts thereof such as molybdic acid and an ammonium molybdate, molybdenum-containing heteropolyacids or salts thereof such as phosphomolybdic acid and silicomolybdic acid, and the like can be used. The raw material of an antimony component is not limited, but antimony trioxide or antimony acetate is preferred. As raw materials for other elements such as vanadium, tungsten, copper and the like, nitrate, sulfate, carbonate, phosphate, organic acid salt, halide, hydroxide, oxide or the metal of these elements can be used.

A compound containing these active components may be used alone or in combination of two or more.

Next, the slurry liquid obtained above is dried to obtain a solid of catalytically active component. The drying method is not limited so long as the slurry liquid can be completely dried by the method. However, examples thereof include drum drying, freeze drying, spray drying and evaporation drying. Spray drying is preferred because the slurry liquid can be dried into a powder or granule in a short period of time. The temperature of the drying with spray drying varies depending on the concentration of the slurry liquid, the liquid sending speed or the like, but the temperature at the outlet of a drying machine is approximately 70° C. to 150° C. In this case, the slurry liquid is preferably dried such that the average particle size of a slurry liquid dried product (catalyst precursor) to be obtained is 10 μm to 700 μm.

The solid of catalytically active component in the second stage obtained as described above can be used as it is for a coating mixture, and is preferably subjected to calcination because the molding properties may be improved. The calcination method and the calcination conditions are not limited, and known treatment methods and conditions can be applied. The optimum calcination conditions vary depending on the used raw material for the catalyst, catalyst composition, preparation method and the like. The calcination temperature is usually 100° C. to 350° C., preferably 150° C. to 300° C., and the calcination time is usually 1 to 20 hours.

The calcination is usually carried out in an air atmosphere, but may be carried out in an atmosphere of an inert gas such as nitrogen, carbon dioxide, helium or argon. The calcination in an air atmosphere may be carried out after calcination in an inert gas atmosphere, if necessary. The thus-obtained calcined solid is preferably pulverized before the molding. The pulverizing method is not limited, but it is preferable to use a ball mill.

The compound containing the active component in preparing the slurry for the second stage does not necessarily have to contain all the active components, and a part of the components may be used before the following molding step.

The shape of the catalyst in the second stage is not limited. The catalyst is used by being molded into a columnar shape, a tablet, a ring shape, a spherical shape or the like in order to reduce the pressure loss of a reaction gas in the oxidation reaction. Among these, the solid of catalytically active component is particularly preferably carried on an inert carrier to be a carried catalyst because improvement in selectivity and removal of heat of reaction can be expected. A tumbling granulation method described below is preferred for the carrying. This method is a method in which, for example, in a device that has a flat or uneven disk at the bottom of a fixed container, a carrier in the container is vigorously agitated by repeatedly performing rotation motion and revolution motion by rotating the disk at a high speed, and then a mixture for the carrying including the binder, the solid of catalytically active component and optionally a molding aid and/or a strength improver is carried on the carrier. As a method of adding the binder, any methods may be adapted such as 1) premixing a binder with the mixture for the carrying, 2) adding the binder at the same time as the mixture for the carrying is added into the fixed container, 3) adding the binder after adding the mixture for the carrying into the fixed container, 4) adding the binder before adding the mixture for the carrying into the fixed container, 5) dividedly preparing the mixture for the carrying and the binder independently and adding the whole amount of them in the appropriate combination of 2) to 4). Among these, for example, 5) is preferably performed by adjusting the adding rate using an auto feeder or the like such that the mixture for the carrying does not adhere to the wall of the fixed container and the mixture for the carrying does not aggregate with each other and a predetermined amount of the mixture for the carrying is carried on the carrier. Examples of the binder include water, ethanol, polyhydric alcohol, polyvinyl alcohol as a polymer-based binder, celluloses such as a crystalline cellulose, methyl cellulose and ethyl cellulose, and an aqueous silica sol solution as an inorganic binder. Diols such as cellulose and ethylene glycol and triols such as glycerin are preferred, and an aqueous solution having a concentration of glycerin of 5 mass % or more is particularly preferred. The amount of these binders to be used is usually 2 to 60 parts by mass, preferably 10 to 50 parts by mass, per 100 parts by mass of the mixture for the carrying.

Specific examples of the carrier in the above carrying include a spherical carrier having a diameter of 1 mm to 15 mm, and preferably 2.5 mm to 10 mm, such as silicon carbide, alumina, silica alumina, mullite and arandom. The carriers having a porosity of 10% to 70% are usually used. The carrier and the mixture for the carrying at the ratio of the mixture for the carrying/(mixture for the carrying+carrier) =10 mass % to 75 mass % are usually used, and the carrier and the mixture for the carrying at the ratio of the mixture for the carrying/(mixture for the carrying+carrier)=15 mass % to 60 mass % are preferably used. When the ratio of the mixture for the carrying tends to be large, the reaction activity of the carried catalyst is large, but the mechanical strength tends to be small. On the contrary, when the ratio of the mixture for the carrying is small, the mechanical strength tends to be large, but the reaction activity tends to be small. In the above, examples of the molding aid to be used as necessary include silica gel, diatomite, and alumina powder. The amount of the molding aid to be used is usually 1 to 60 parts by mass with respect to 100 parts by mass of the solid of catalytically active component. If necessary, the use of inorganic fibers (for example, ceramic fibers or whiskers) that are inactive to the solid of catalytically active component and the reaction gas as the strength improver is useful for improving the mechanical strength of the catalyst, and glass fibers are preferred. The amount of the fiber to be used is usually 1 to 30 parts by mass with respect to 100 parts by mass of the solid of catalytically active component. None of a molding aid, a pore-forming agent and a carrier added in the molding of the catalyst for the first stage is considered as the constituent element of the active component in the first aspect, regardless of whether the molding aid, the pore-forming agent and the carrier have the activity in the sense of converting the raw material into some other product.

The carried catalyst obtained as described above can be used as a catalyst for the catalytic gas phase oxidation, and is preferably subjected to calcination because the molding properties may be improved. The calcination method and the calcination conditions are not limited, and known treatment methods and conditions can be applied. The optimum calcination conditions vary depending on the raw material for the catalyst to be used, the catalyst composition, the preparation method, and the like, but the calcination temperature is usually $100° C.$ to $450° C.$, preferably $270° C.$ to $420° C.$, and the calcination time is usually 1 to 20 hours. The calcination is usually carried out in an air atmosphere, and may be carried out in an atmosphere of an inert gas such as nitrogen, carbon dioxide, helium or argon. The calcination in an air atmosphere may be carried out after the calcination in an inert gas atmosphere, if necessary.

When the catalyst of the first aspect is used in a reaction of using propylene, isobutylene, t-butyl alcohol and the like as raw materials to produce the corresponding unsaturated aldehyde, unsaturated carboxylic acid, and particularly, in a reaction of producing acrolein and acrylic acid by catalytic gas phase oxidation of propylene with molecular oxygen or a gas containing molecular oxygen, using the catalyst of the first aspect allows for improving the catalytic activity and the yield, and is very effective in improving the price competitiveness of the product as compared with the known method. In addition, the effect of improving the process stability of the partial oxidation reaction accompanied by heat generation, such as reduction of the hot spot temperature can be expected. Further, the catalyst of the first aspect is also effective in reducing by-products that adversely influences the environment and the quality of the final product, such as carbon monoxide (CO), carbon dioxide ($CO_2$), acetaldehyde, acetic acid, and formaldehyde.

The thus-obtained catalyst of the first aspect can be used, for example, for producing acrolein and/or acrylic acid by catalytic gas phase oxidation of propylene using a molecular oxygen-containing gas. In the production method of the first aspect, the method for flowing the raw material gas may be an ordinary single-flow method or a recycling method, and can be carried out under widely used conditions, and is not limited. For example, a mixed gas containing 1 vol % to 10 vol % and preferably 4 vol % to 9 vol % of propylene, 3 vol % to 20 vol % and preferably 4 vol % to 18 vol % of molecular oxygen, 0 vol % to 60 vol % and preferably 4 vol % to 50 vol % of water vapor at room temperature as a starting raw material, and 20 vol % to 80 vol % and preferably 30 vol % to 60 vol % of an inert gas such as carbon dioxide and nitrogen is introduced to the catalyst of the first aspect filled in a reaction tube at $250° C.$ to $450° C.$ under normal pressure to 10 atm and a space velocity of 300 to 5000 $h^{-1}$ to perform a reaction.

In the first aspect, unless otherwise specified, the improvement of the catalytic activity means that the conversion rate of the raw material is high when the catalytic reaction is carried out at the same salt bath temperature.

In the first aspect, unless otherwise specified, a high yield means that the total yield of the corresponding unsaturated aldehyde and/or unsaturated carboxylic acid is high when the oxidation reaction is performed using propylene, isobutylene, t-butyl alcohol, and the like as raw materials. Unless otherwise specified, the yield refers to a useful yield described later.

In the first aspect, unless otherwise specified, the constituent elements of the catalytically active component refer to all the elements to be used in the method for producing a catalyst, but the raw materials and the constituent elements thereof that disappear, sublimate, volatilize, and burn at the maximum temperature or lower in the main calcination step are not included in the constituent elements of the catalytically active component. Further, silicon and the other elements constituting inorganic materials contained in the molding aid and the carrier in the shaping step are not included in the constituent elements of the catalytically active component.

In the first aspect, the hot spot temperature refers to the maximum temperature in the temperature distribution in the catalyst-filled bed that is measured in thermocouples installed in the multi-tube reaction tube in the long axis direction, and the salt bath temperature refers to a set temperature of a heat medium used for the purpose of cooling the heat generated in the reaction tube. The number of measuring points in the temperature distribution is not limited, but for example, the catalyst filling length is evenly divided from 10 to 1000.

In the first aspect, the unsaturated aldehyde and the unsaturated aldehyde compound refers to organic compounds having at least one double bond and at least one aldehyde in the molecule, such as acrolein and methacrolein. In the first aspect, the unsaturated carboxylic acid and the unsaturated carboxylic acid compound refers to organic compounds having at least one double bond and at least one carboxy group or an ester group of the carboxyl group in the molecule, and are, for example, acrylic acid, methacrylic acid, and methyl methacrylate. In the first aspect, the conjugated diene refers to a diene in which a double bond is separated by one single bond and which is chemically conjugated, and is, for example, 1,3-butadiene.

Further, the catalyst of the first aspect has advantages that the reaction process can be stably maintained from the reason that (1) the hot spot temperature is reduced and (2) the activity of the catalyst is stable even when the salt bath temperature is low.

[[Second Aspect]]
[Changing Rate (Q1) of Peak Intensity at $2\theta=25.3°\pm0.2°$ in X-Ray Diffraction Pattern per 1000 Hours of Reaction Time]

A production method of a second aspect of the present invention is characterized in that a changing rate (Q1) per 1000 hours of reaction time represented by the following formulae (II-1) to (II-4) is suppressed to 10.0 or less in regard to the peak intensity at $2\theta=25.3°\pm0.2°$ in an X-ray diffraction pattern obtained by using CuKα rays as an X-ray source.

$$Q1=\{(U1/F1-1)\times100\}/T\times1000 \qquad \text{(II-1)}$$

$$F1=\text{(peak intensity of catalyst before oxidation reaction at }2\theta=25.3°\pm0.2°\text{)/(peak intensity of catalyst before oxidation reaction at }2\theta=26.5°\pm0.2°\text{)}\times100 \qquad \text{(II-2)}$$

$$U1=\text{(peak intensity of catalyst after oxidation reaction at }2\theta=25.3°\pm0.2°\text{)/(peak intensity of catalyst after oxidation reaction at }2\theta=26.5°\pm0.2°\text{)}\times100 \qquad \text{(II-3)}$$

$$T=\text{time (hr) for which oxidation reaction is carried out} \qquad \text{(II-4)}$$

The peak intensity (F1) and the peak intensity (U1) are determined by normalization based on the peak intensity observed at $2\theta=26.5°\pm0.2°$, but for the changing rate (Q1), U1 is divided by F1, and thus the peak intensity (F1) and the peak intensity (U1) are calculated substantially based on a value determined by (peak intensity value of catalyst after oxidation reaction at $2\theta=25.3°\pm0.2°$)/(peak intensity value of catalyst before oxidation reaction at $2\theta=25.3°\pm0.2°$).

Here, the peak intensity will be described. The peak intensity at $2\theta=25.3°\pm0.2°$ means a local maximum value of a signal observed in a range of $2\theta=25.3°\pm0.2°$, and the nature thereof indicates a peak height of a crystal phase of α-$CoMoO_4$. The peak intensity at $2\theta=26.5°\pm0.2°$ means a local maximum value of a signal observed in a range of $2\theta=26.5°\pm0.2°$, and the nature thereof indicates a peak height of a crystal phase of β-$CoMoO_4$. That is, the second aspect is based on the finding that when the changing rate (Q1) of the peak intensity of the crystal phase of α-$CoMoO_4$ observed at $2\theta=25.3°\pm0.2°$ per 1000 hours of reaction time due to the oxidation reaction with respect to the peak intensity of the crystal phase of β-$CoMoO_4$ observed at $2\theta=26.5°\pm0.2°$ is equal to or less than a certain value, specifically, is 10.0 or less, the selectivity is stabilized in a high state.

As will be described later, the change in the crystal phase of α-$CoMoO_4$ can be adjusted by, for example, controlling the oxygen concentration at the outlet of the reaction tube. This can be confirmed particularly by focusing on the changing rate (Q1) of the peak intensity at $2\theta=25.3°\pm0.2°$ per 1000 hours of reaction time. The range of Q1 is 10.0 or less as described above, and an upper limit of the range is more preferably 9.5, 9.0, or 8.5 in order, still more preferably 8.2, yet still more preferably 8.0, and most preferably 7.9. A lower limit of the range may not be set, but is preferably $-100$, $-80$, $-60$, $-40$, and $-20$ in order, more preferably $-15$, still more preferably $-10$, and most preferably $-8.0$. That is, a more preferred range of the changing rate (Q1) of the peak intensity per 1000 hours of reaction time is set by the upper and lower limits described above, and is, for example, $-40$ to 8.0, and most preferably $-8.0$ to $-7.9$.

Examples of a method of measuring an X-ray diffraction angle ($2\theta$) include measuring the X-ray diffraction angle ($2\theta$) under conditions of X-ray CuKα rays (λ=0.154 nm), an output of 40 kV, 30 mA, a measurement range of 10° to 60°, and a measurement speed of 10° per minute by using Ultima IV manufactured by Rigaku Corporation, but the method is not limited thereto as long as the method does not depart from the measurement principle. In addition, for the peak intensity of the second aspect, the calculation is performed after the background and halo pattern are eliminated as described in Patent Literature 3 in the X-ray diffraction pattern. In addition, when each of the peaks does not have a clear local maximum value within the corresponding range of $2\theta$, or does not have a peak shape, or when it is not determined that the peak is a clear peak due to too much noise, the peak intensity is assumed to be 0 in the second aspect.

[Amount of Change (D1) of Peak Intensity at $2\theta=25.3°\pm0.2°$ Per 1000 Hours of Reaction Time in X-Ray Diffraction Pattern]

The catalyst of the second aspect is preferably characterized in an amount of change (D1) per 1000 hours of reaction time represented by the following formula (II-5) and the above formulae (II-2) to (II-4) with respect to the peak intensity at $2\theta=25.3\pm0.2°$ in an X-ray diffraction pattern obtained by using CuKα rays as an X-ray source.

$$D1=(U1-F1)/T\times1000 \tag{II-5}$$

It has been found that when the amount of change (D1) of the peak intensity at $2\theta=25.3°\pm0.2°$ per 1000 hours of reaction time for the oxidation reaction with respect to the peak intensity at $2\theta=26.5°\pm0.2°$ is equal to or less than a certain value, specifically, is as small as 4.0 or less, the catalyst is stabilized with the high selectivity kept.

As will be described later, the crystal phase of α-CoMoO$_4$ changes and the stability thereof also changes by a method of controlling the oxygen concentration at the outlet of the reaction tube or the like. This can be confirmed particularly by focusing on the amount of change (D1) of the peak intensity at $2\theta=25.3°\pm0.2°$ per 1000 hours of reaction time. The range of D1 is preferably 4.0 or less as described above, and the upper limit value thereof is more preferably 3.8, 3.5, or 3.0 in order, still more preferably 2.8, yet still more preferably 2.5, and most preferably 2.0. The lower limit value thereof may not be set, but is preferably −17, −15, and −10 in order, more preferably −5.0, still more preferably −2.0, and most preferably −1.5. That is, a more preferred range of the amount of change (D1) of the peak intensity per 1000 hours of reaction time is set by the upper and lower limits described above, and is, for example, −10 to 2.5, and most preferably −1.5 to 2.0.

[Time T (Hr) for which Oxidation Reaction is Carried Out]

The oxidation reaction time T (hr) in the second aspect is determined within a specific time of 300 hours or more and 30000 hours or less, preferably 800 hours or more and 28000 hours or less, more preferably 1000 hours or more and 26000 hours or less, and most preferably 6600 hours.

However, for the characteristics of the catalyst of the second aspect, Q1 is particularly preferably 10.0 or less at any time within 300 hours or more and 30000 hours or less. It should be noted that when substituting into the above calculation formula, it is preferable to perform the calculation with two significant digits.

The catalyst used in the production method of the second aspect preferably has a peak at $2\theta=27.4°\pm0.1°$ in addition to the above peak, in the X-ray diffraction pattern obtained by using CuKα rays as an X-ray source. When the peak intensity is within a specific range, the catalyst is more preferable. Assuming that the peak intensity is S3 represented by the following, the lower limit of S3 is 10.0, 10.2, or 10.5 in preferred order, and most preferably 11.0, and the upper limit of S3 is 15.0 or 14.5 in preferred order, and most preferably 13.5. That is, the preferred range of S3 is 12.0 or more and 14.0 or less, and most preferred range of S3 is 11.0 or more and 13.5 or less.

$$S3=(\text{peak intensity at } 2\theta=27.4°\pm0.1°)/(\text{peak intensity}$$
$$\text{at } 2\theta=26.5°\pm0.1°)\times100$$

In the second aspect, the effect of the second aspect can be clarified by evaluating and comparing the catalyst before the oxidation reaction and the catalyst after the oxidation reaction under the same evaluation conditions. The evaluation conditions may be any conditions, but it is preferable that the evaluation is performed under a condition in which a propylene space velocity is as large as 300 hr$^{-1}$ or more because it is easy to find a difference between the catalysts before and after the oxidation reaction.

When the evaluation is performed under the condition of the propylene space velocity of 300 hr$^{-1}$ or more, it is preferable to use a reactor having a small scale because the evaluation can be easily performed. For the change of the reactor, when the catalyst is extracted from the reaction tube in order to obtain the catalyst after the oxidation reaction, the reaction tube may be equally divided into three or more sections in the longitudinal direction, and the catalyst may be sampled in equal amounts from the respective positions and mixed, and then the evaluation may be performed.

[Catalyst Composition]

The catalytically active component contained in the catalyst of the second aspect preferably has a composition represented by the following formula (II-A).

$$Mo_{a3}Bi_{b3}Ni_{c3}Co_{d3}Fe_{e3}X3_{f3}Y3_{g3}Z3_{h3}O_{i3} \tag{II-A}$$

(in the formula, Mo, Bi, Ni, Co and Fe represent molybdenum, bismuth, nickel, cobalt and iron, respectively; X3 is at least one element selected from tungsten, antimony, tin, zinc, chromium, manganese, magnesium, silicon, aluminum, cerium and titanium; Y3 is at least one element selected from sodium, potassium, cesium, rubidium, and thallium; Z3 belongs to the 1st to 16th groups in the periodic table and means at least one element selected from elements other than the above Mo, Bi, Ni, Co, Fe, X3, and Y3; a3, b3, c3, d3, e3, f3, g3, h3, and i3 represent the number of atoms of molybdenum, bismuth, nickel, cobalt, X3, Y3, Z3, and oxygen, respectively; when a3=12, 0<b3≤7, 0≤c3≤10, 0<d3≤10, 0<c3+d3≤20, 0≤e3≤5, 0≤g3≤2, 0≤f3≤3, 0≤h3≤5, and i3 is a value determined by an oxidation state of each element).

In the above formula (II-A), preferred ranges of b3 to i3 are as follows.

The lower limit of b3 is 0.2, 0.5, 0.7, or 0.8 in preferred order, and most preferably 0.9, and the upper limit of b3 is 5, 3, 2, 1.6, 1.4, or 1.2 in preferred order, and most preferably 1.1. That is, the most preferred range of b3 is 0.9≤b3≤1.1.

The lower limit of c3 is 1, 2, 2.5, 2.8, or 3.0 in preferred order, and most preferably 3.1, and the upper limit of c3 is 5, 4, 3.8, 3.6, or 3.4 in preferred order, and most preferably 3.2. That is, the most preferred range of c3 is 3.1≤c3≤3.2.

The lower limit of d3 is 3, 4, 5, 5.3, 5.5, or 5.7 in preferred order, and most preferably 5.8, and the upper limit of d3 is 8, 7, 6.5, 6.3, or 6.1 in preferred order, and most preferably 6.0. That is, the most preferred range of d3 is 5.8≤d3≤6.0.

The lower limit of e3 is 0.5, 1, 1.2, or 1.4 in preferred order, and most preferably 1.5, and the upper limit of e3 is 4, 3, 2.5, 2, or 1.8 in preferred order, and most preferably 1.7. That is, the most preferred range of e3 is 1.5≤e3≤1.7.

The upper limit of f1 is 8, 7, 6, or 5 in preferred order. That is, the most preferred range of f1 is 0≤f3≤5.

The lower limit of g3 is 0, 0.02, 0.04, or 0.06 in preferred order, and most preferably 0.07, and the upper limit of g3 is 1.5, 1, 0.5, 0.2, or 0.15 in preferred order, and most preferably 0.10. That is, the most preferred range of g3 is 0.07≤g3≤0.10.

The upper limit of h3 is 8, 7, 6, or 5 in preferred order. That is, the most preferred range of h3 is 0≤h3≤5.

It is preferable that two or less types of Y3 are contained, and one type is particularly preferred. In addition, it is particularly preferable that f3 and h3 are 0.

[Carrying]

The catalyst in which a preliminary calcined powder subjected to preliminary calcination after the preparation of the catalytically active component is carried on the inert carrier is particularly excellent as the catalyst of the first aspect.

As the material of the inert carrier, known materials such as alumina, silica, titania, zirconia, niobia, silica alumina, silicon carbide, carbides, and mixtures thereof can be used. Further, the particle size, water absorption rate, mechanical strength, crystallinity of each crystal phase, mixing ratio, etc. are not limited, and an appropriate range of these should be selected in consideration of the final catalyst performance, molding properties, production efficiency, etc. The mixing ratio of the carrier and the preliminarily calcined powder is calculated as the active mass ratio according to the following equation based on the charged mass of each raw material.

$$\text{Active mass ratio (mass \%)} = \text{(mass of preliminary calcined powder used for molding)}/\{\text{(mass of preliminary calcined powder used for molding)} + \text{(mass of carrier used for molding)}\} \times 100$$

The upper limit of the active mass ratio is preferably 80 mass %, and more preferably 60 mass %.

The lower limit is preferably 20 mass %, and more preferably 30 mass %. That is, the most preferred range of the active mass ratio is 30 mass % or more and 60 mass % or less.

As the inert carrier, silica and/or alumina is preferable, and a mixture of silica and alumina is particularly preferable.

For the carrying, it is preferred to use a binder. Specific examples of the binder which can be used include water, ethanol, methanol, propanol, a polyhydric alcohol, polyvinyl alcohol as a polymer-based binder, and a silica sol aqueous solution as an inorganic binder; ethanol, methanol, propanol, and a polyhydric alcohol are preferred; a diol such as ethylene glycol and a triol such as glycerin is preferred; and an aqueous solution having a concentration of glycerin of 5 mass % or more is preferred. Using an appropriate amount of a glycerin aqueous solution allows for obtaining a high-performance catalyst having good molding properties and high mechanical strength. The amount of these binders used is usually 2 to 60 parts by mass with respect to 100 parts by mass of the preliminarily calcined powder. The amount of glycerin aqueous solution is preferably 10 to 30 parts by mass. The binder and the preliminarily calcined powder may be alternately or simultaneously supplied to a molding machine on the occasion of carrying.

[Means for Adjusting Q1, D1, and S3]

For means for controlling Q1, D1, and S3, the control can be performed by changing each condition in each production process of the catalyst to be described later, but the control can be performed by changing the conditions for producing the unsaturated aldehyde compound, the unsaturated carboxylic acid compound, and/or the conjugated diene. Examples thereof include (I) a method of controlling a hot spot temperature of a catalyst layer, (II) a method of controlling an oxygen concentration at an outlet of a reaction tube, (III) a method of controlling a steam concentration at an inlet of a reaction tube, (IV) a method of controlling a rate of temperature decrease when any process for temperature decrease is performed during the reaction, (V) a method of preventing a mechanical impact on a catalyst, (VI) a method of controlling a load of a raw material during a reaction such that the load is constant, (VII) a method of appropriately switching to an nitrogen purge operation during a reaction, and a method of combining the methods (I) to (VII).

The method (I) is a method of controlling the hot spot temperature of the catalyst layer at 427° C. or lower for producing an unsaturated aldehyde compound, an unsaturated carboxylic acid compound, and/or a conjugated diene, and the upper limit of the hot spot temperature is preferably 420° C. or lower, 410° C. or lower, 400° C. or lower, 390° C. or lower, or 380° C. or lower. That is, the hot spot temperature is most preferably 380° C. or lower. The time for controlling the hot spot temperature is 500 hours or less, preferably 300 hours or less, more preferably 200 hours or less, still more preferably 100 hours or less, and most preferably 50 hours or less.

The method (II) is a method of controlling the oxygen concentration at the outlet of the reaction tube for producing an unsaturated aldehyde compound, an unsaturated carboxylic acid compound, and/or a conjugated diene to 3.0 vol % or more and 4.7 vol % or less. The lower limit of the oxygen concentration is preferably 3.5 vol % or more, more preferably 3.8 vol % or more, and particularly preferably 4.0 vol % or more. The upper limit of the oxygen concentration is preferably 4.6 vol %, more preferably 4.5 vol %, and particularly preferably 4.4 vol %. That is, the oxygen concentration at the outlet of the reaction tube is most preferably 3.8 vol % or more and 4.4 vol % or less.

The method (III) is a method of controlling the steam concentration at the inlet of the reaction tube for producing an unsaturated aldehyde compound, an unsaturated carboxylic acid compound, and/or a conjugated diene to 30 vol % or less. The upper limit of the steam concentration is 25 vol % or less, 20 vol % or less, 15 vol % or less, 10 vol % or less, and 9 vol % or less in preferred order. That is, the steam concentration is most preferably 9 vol % or less.

Regarding the method (IV), a rate of decrease (rate of temperature decrease) of the temperature of the catalyst itself from a salt bath temperature to 100° C. or less is 1° C./min or more and 200° C./min or less, preferably 5° C./min or more and 150° C./min or less, more preferably 10° C./min or more and 120° C./min or less, and most preferably 50° C./min or more and 100° C./min or less. In order to achieve the above-described range of the rate of temperature decrease, all methods industrially typically taken for the temperature decrease fall within the second aspect.

The method (V) is a method of controlling the catalyst such that the catalyst is not subjected to a mechanical impact, a shear stress, and the like in any step from the filling of the catalyst to the reaction, and the preferred range of the mechanical impact, the shear stress, and the like is controlled to 100 kgf or less, preferably 50 kgf or less, more preferably 20 kgf or less, still more preferably 10 kgf or less, and most preferably 5 kgf or less.

The method (VI) is a method of controlling a load (SV) of the raw material during the reaction not to vary. Typically, a commercial plant performs production control by changing the load according to the market of the target product, but it is not preferable from the viewpoint of stability of the catalyst performance, and it is preferable to perform the control of the load to make the load constant after checking Q1 and D1 of the second aspect, and further to perform production control by shutting down as necessary. The control range in which the load is kept constant should be controlled within a range of ±20% with respect to the target value of the load of the raw material for reaction, and is more preferably ±15%, still more preferably ±10%, and most preferably ±5%. In addition, a pressure difference (differential pressure) between the inlet and the outlet of a catalyst-filled layer may also vary in accordance with the variation of the load. The differential pressure should also be controlled to be constant and as low as possible after checking Q1 and D1, and is preferably 50 kPaG or less, and more preferably 30 kPaG or less.

The method (VII) is a method of performing an operation (nitrogen purge) of allowing only nitrogen gas to flow through the catalyst during a reaction. Switching to the nitrogen purge operation for the catalyst is not preferable as an operation method of the commercial plant, but the embodiment of the switching should be performed from the viewpoint of stability of the catalyst performance. That is, after confirming Q1 and D1 of the second aspect, the switching to the nitrogen purge operation is appropriately performed, and the number of times for the switching is not limited, and the flow rate is 100 $hr^{-1}$ or more, preferably 250 $hr^{-1}$ or more, more preferably 500 $hr^{-1}$ or more, and most preferably 1000 $hr^{-1}$ as SV of nitrogen with respect to the catalyst, and the nitrogen purge time is 10 hr or more, preferably 100 hr or more, and more preferably 500 hr or more.

Q1, D1, and S3 in the production method of the second aspect vary depending on the catalyst, it is also useful to devise the production method of the catalyst itself. For example, the following method (VIII) to (XVIII) can be used:

(VIII) a method of changing a catalyst composition, (IX) a method of changing calcination conditions, (X) a method of changing conditions of temperature decrease after calcination, (XI) a method of controlling a catalyst and a precursor thereof such that the catalyst and the precursor are not subjected to a mechanical strength in all steps of production of the catalyst, (XII) a method of using a raw material having high purity, other methods (XIII) to (XVIII). The method of combining (VIII) to (XVIII) can be also used. The details of the other methods (XIII) to (XVIII) will be described later.

The method (VIII) is a method of adjusting d3/(b3+c3+e3) in the composition formula (II-A) to a specific range, and the upper limit thereof is 1.25, preferably 1.20, and more preferably 1.10, and the lower limit thereof is 0.10, 0.30, 0.50, 0.70, 0.80, 0.90, or 1.00 in preferred order. That is, the most preferred range is 1.00 or more and 1.10 or less.

In addition, the upper limit of e3/b3 is 1.90, preferably 1.80; the lower limit of e3/b3 is 0.10, 0.50, 1.00, 1.40, or 1.50 in preferred order; the upper limit of d3/b3 is 9.0, 8.0, 7.0, or 6.0 in preferred order; the lower limit of d3/b3 is 2.0, 3.0, 4.0, 5.0, or 5.5 in preferred order; the upper limit of c3/e3 is 4.0, 3.0, or 2.5 in preferred order; the lower limit of c3/e3 is 1.5, 1.7, or 1.9 in preferred order; the upper limit of c3/d3 is 2.0, 1.0, or 0.8 in preferred order; the lower limit of c3/d3 is 0.4, or 0.5 in preferred order; the upper limit of g3/d3 is 0.20, 0.19, 0.18, 0.17, 0.16, 0.15, 0.14, or 0.10 in preferred order; the lower limit of g3/d3 is 0.01, 0.02, 0.03, 0.04, or 0.05 in preferred order; the upper limit of g3/c3 is 0.041, 0.039, 0.037, 0.035, 0.033, 0.031, 0.029, 0.025, or 0.023 in preferred order; and the lower limit of g3/c3 is 0.017, 0.019, or 0.021 in preferred order. Furthermore, in the composition formula (II-A), the lower limit of c3+d3+e3 is 7.0, 7.5, 8.0, 8.5, 9.0, or 9.5 in preferred order, the upper limit of c3+d3+e3 is 13.0, 12.5, 12.0, 11.5, 11.0, or 10.5 in preferred order, the lower limit of b3+c3+d3+e3 is 8.0, 8.5, 9.0, 9.5, 10.0, 10.5, or 11.0 in preferred order, and the upper limit of b3+c3+d3+e3 is 14.0, 13.5, 13.0, 12.5, 12.0, or 11.5 in preferred order.

Regarding the method (IX), a temperature in preliminary calcination and main calcination as described later and in both of them is 200° C. or more and 600° C. or less, preferably 300° C. or more and 550° C. or less, and more preferably 460° C. or more and 550° C. or less, and a time in preliminary calcination and main calcination as described later and in both of them is 0.5 hours or more, preferably 1 hour or more and 40 hours or less, more preferably 2 hours or more and 15 hours or less, and most preferably 2 hours or more and 9 hours or less. An atmosphere in preliminary calcination and main calcination as described later and in both of them has 10 vol % or more and 40 vol % or less of the oxygen concentration, preferably 15 vol % or more and 30 vol % or less, more preferably 10% to 25%, and most preferably the atmosphere is an air atmosphere.

Regarding the method (X), in the preliminary calcination and the main calcination as described later and in both of them, a rate of decrease (rate of temperature decrease) of the temperature of a catalyst surface from the maximum temperature (preliminary calcination temperature or main calcination temperature) reached in the calcination step to the room temperature is 1° C./min or more and 200° C./min or less, preferably 5° C./min or more and 150° C./min or less, more preferably 10° C./min or more and 120° C./min or less, and most preferably 50° C./min or more and 100° C./min or less. A temperature decrease method industrially typically taken for achieving the range of the rate of temperature decrease described above, for example, a method of exposing a calcined catalyst taken out from a calcination furnace to an inert atmosphere or a mist of an inert solvent, and a method of rapidly moving a calcined catalyst into a room sufficiently cooled in advance are all included in the second aspect.

The method (XI) is a method of controlling a catalyst precursor to be described later and/or granules formed in each step such that the catalyst precursor and/or granules are not subjected to a mechanical impact, a shear stress, and the like, and the preferred range of the mechanical impact, shear stress, and the like is controlled to 100 kgf or less, preferably 50 kgf or less, more preferably 20 kgf or less, still more preferably 10 kgf or less, and most preferably 5 kgf or less.

The method (XII) is not limited as long as the method (XII) is a method using a high purity raw material at the level of reagent, and for example, the content of sulfur and a compound thereof, lithium, halogen and a compound thereof, and lead in the raw material is 10000 ppm by weight or less, preferably 1000 ppm by weight or less, more preferably 100 ppm by weight, and most preferably 10 ppm by weight or less.

Regarding the method (XIII), as described later, is, for example, a method in which a catalyst precursor is once obtained as granules and the granules are molded. Obtaining the catalyst precursor in the form of granules allows for producing the catalyst such that each component of the catalyst can be more uniform.

The method (XIV) is a method of controlling a time during which a cobalt raw material and a nickel raw material are mixed, reacted, slurried, and retained in a mixing pot to be as short as possible in the step of preparing the catalyst to be described later, and more specifically, is a method of shortening the retention time in a state in which a metal salt raw material excluding molybdenum and alkali metal is not in the mixing pot and the cobalt raw material and the nickel raw material are present in the mixing pot, or a method of shortening the retention time in a state in which the cobalt raw material and the nickel raw material are present in the mixing pot when a pH in the mixing pot falls within a specific range. The retention time is preferably 24 hours, more preferably 1 hour, still more preferably 30 minutes, and most preferably 10 minutes. The range of pH is 1 or more and 14 or less, preferably 2 or more and 10 or less, more preferably 2 or more and 8 or less, and most preferably 3 or more and 7 or less. The same applies to an iron raw material and a bismuth raw material, a molybdenum raw material, and a bismuth raw material.

The method (XV) is a method in which, in the step of preparing a catalyst to be described later, the raw materials are charged in two or more times in a divided manner instead of charging a necessary amount of each raw material at a time. After the divided raw material is charged once, a certain interval is preferably set until the raw material is charged next. The time of the interval is preferably 5 seconds or more and 1 hour or less, more preferably 30 seconds or more and 45 minutes or less, still more preferably 1 minute or more and 30 minutes or less, and most preferably 3 minutes or more and 15 minutes or less. The number of divisions of one raw material is preferably 2 or more, more preferably 3 or more, still more preferably 4 or more, and most preferably 5 or more. Some raw materials can be divided in a series of preparation steps, each raw material may be divided individually, the raw materials may be mixed as described below and then divided collectively, or the raw materials divided individually may be alternately charged.

Regarding the method (XVI), when the aqueous solutions of the respective raw materials are mixed and stirred to prepare a suspended slurry in the step of preparing a catalyst to be described later, an adding time of the two or more aqueous solutions used for the mixing is preferably 1 second or more and 30 minutes or less, more preferably 10 seconds or more and 20 minutes or less, still more preferably 30 seconds or more and 5 minutes or less, and most preferably 1 minute or more and 5 minutes or less.

Regarding the method (XVII), in the step of preparing a catalyst to be described later, a transfer time from preparing the suspended slurry in a final state to moving to the drying step as a next step is preferably 10 seconds or more and 1 hour or less, more preferably 30 seconds or more and 10 minutes or less, and most preferably 1 minute or more and 5 minutes or less.

The method (XVIII) is a method for adding an organic substance before or after each raw material is added, in the step of preparing a catalyst to be described later, and the lower limit of the amount of the organic substance to be added to the molybdenum raw material is preferably 0.001 mol % or more, more preferably 0.01 mol % or more, still more preferably 0.1 mol % or more, and most preferably 1 mol % or more, and the upper limit of the amount of the organic substance to be added to the molybdenum raw material is preferably 100 mol % or less, more preferably 90 mol % or less, still more preferably 80 mol % or less, and most preferably 60 mol % or less. Carboxylic acids and alcohols are preferable as the organic substance to be added. Examples of the organic substance include acetic acid, propionic acid, lactic acid, citric acid, stearic acid, oleic acid, ethylenediamine tetraacetic acid, methanol, ethanol, propanol, ethylene glycol, and glycerin.

[Method for Producing Catalyst]

A starting raw material for each element constituting the catalyst to be used for production method of the second aspect and the preliminary calcined powder thereof is not limited. For example, as a raw material of a molybdenum component, molybdenum oxides such as molybdenum trioxide, molybdic acid or salts thereof such as molybdate, ammonium paramolybdate and ammonium metamolybdate, and heteropolyacids containing molybdenum or salts thereof such as phosphomolybdic acid and silicate molybdic acid, can be used.

As a raw material of a bismuth component, bismuth salts such as bismuth nitrate, bismuth carbonate, bismuth sulfate, and bismuth acetate, bismuth trioxide, metal bismuth and the like can be used. These raw materials can be used as solids or as an aqueous solution, a nitric acid solution, or a slurry of bismuth compounds generated from those aqueous solutions, and the nitrate, a solution thereof, or a slurry obtained from the solution is preferably used.

As a starting raw material for other constituent elements, ammonium salt, nitrate, nitrite, carbonate, subcarbonate, acetate, chloride, inorganic acid, inorganic acid salt, heteropolyacid, heteropolyacid salt, sulfate, hydroxide, organic acid salt, and oxide of metallic elements commonly used in this type of catalyst may be used, or a mixture thereof may be used in combination. Ammonium salts and nitrates are preferably used.

A compound containing these active components may be used alone or in combination of two or more. A slurry liquid can be obtained by uniformly mixing each compound containing an active component and water. The amount of water to be used in the slurry liquid is not limited as long as the total amount of the compound to be used can be completely dissolved or uniformly mixed. The amount of water to be used may be appropriately determined in consideration of the drying method and the drying conditions. Usually, the amount of water to be used is 100 parts by mass or more and 2000 parts by mass or less with respect to 100 parts by mass of the total mass of the compound for preparing a slurry. The amount of water may be large, but too large amount of water causes many disadvantages such as an increase in the energy cost of the drying step and a possible failure to completely dry.

The slurry liquid of the source compound of the above each component element is preferably prepared by (a) a method of mixing each of the above source compounds at once, (b) a method of mixing the above source compounds at once and then performing aging, (c) a method of mixing the above source compounds stepwise, (d) a method of repeating mixing step and aging step stepwise, and (e) a method combining (a) to (d). Here, the above aging means "an operation in which industrial raw materials or semi-finished products are processed under specific conditions such as a certain period of time and a certain temperature to conduct acquisition or improvement of the required physical properties and chemical properties, or proceeding of a predetermined reaction". In the second aspect, the above certain period of time means a range of 5 minutes or longer and 24 hours or shorter, and the above certain temperature means a range from room temperature to a point equal to or lower than a boiling point of an aqueous solution or an aqueous dispersion liquid. Among these, in terms of the activity and yield of the finally obtained catalyst, preferred is the (c) method of mixing the above source compounds stepwise, more preferred is a method in which each raw material to be mixed with a mother liquid stepwise is completely dissolved to be a solution, and most preferred is a method of mixing various mixed solutions of alkali metal solution and nitrate with a mother liquid in which the raw material of the molybdenum is a mixed solution or slurry. However, it is not always necessary to mix all the elements constituting the catalyst in this step, and some elements or some amounts thereof may be added in the subsequent steps.

In the second aspect, the shape of the stirring blade of the stirrer used in mixing the essential active components is not limited. Any stirring blade such as a propeller blade, a turbine blade, a paddle blade, an inclined paddle blade, a screw blade, an anchor blade, a ribbon blade, a large lattice blade can be used in one stage or in two or more stages of which blades are the same or different types in the vertical direction. In addition, a baffle (obstruction plate) may be installed in the reaction tank if necessary.

Then, the slurry liquid thus-obtained is dried. The drying method is not limited so long as the slurry liquid can be completely dried by the method, but examples thereof include drum drying, freeze drying, spray drying and evaporation drying. Among these, spray drying, which allows the slurry liquid to be dried into a powder or granule within a short period of time, is particularly preferred in the second aspect. The temperature of the drying with spray drying varies depending on the concentration of the slurry liquid, the liquid sending speed, or the like. Typically, the temperature at the outlet of a drying machine is 70° C. or higher and 150° C. or lower.

Subjecting the catalyst precursor obtained as described above to preliminary calcination, molding, and then main calcination allows for controlling and holding the obtained shape, and obtaining a catalyst having particularly excellent mechanical strength for industrial use, and the catalyst can exhibit stable catalyst performance.

As for the molding, either a carrying shaping in which the preliminarily calcined powder is carried on a carrier such as silica or a non-carrying shaping in which no carrier is used can be adopted. Specific examples of the molding method include tablet molding, press molding, extrusion molding and granulation molding. As the shape of the molded product, for example, a columnar shape, a ring shape, a spherical shape or the like can be appropriately selected in consideration of operating conditions. Preferred is a carried catalyst in which a catalytically active component is carried on a spherical carrier, particularly an inert carrier such as silica or alumina and in which the average particle size is 3.0 mm or more and 10.0 mm or less, and preferably 3.0 mm or more and 8.0 mm or less. As for the carrying method, a tumbling granulation method, a method using a centrifugal flow coating apparatus, a wash coating method, and the like are widely known. The method is not limited as long as the preliminarily calcined powder can be uniformly carried on the carrier, but the tumbling granulation method is preferred in consideration of the production efficiency of the catalyst and the like. Specifically, the tumbling granulation method is a method in which using a device that has a flat or uneven disk at the bottom of a fixed cylindrical container, a carrier charged into the container is vigorously agitated by means of a repeat of rotation motion and revolution motion of the carrier itself by rotating the disk at a high speed, and then the preliminarily calcined powder is added into the container to carry the powder component on the carrier.

On the occasion of carrying, it is preferred to use a binder. Specific examples of the binder which can be used include water, ethanol, methanol, propanol, a polyhydric alcohol, polyvinyl alcohol as a polymer-based binder and a silica sol aqueous solution as an inorganic binder; ethanol, methanol, propanol, and a polyhydric alcohol are preferred; a diol such as ethylene glycol and a triol such as glycerin is more preferred; and an aqueous solution of glycerin having a concentration of 5 mass % or more is still more preferred. Using an appropriate amount of the glycerin aqueous solution allows for obtaining a high-performance catalyst having good molding properties and high mechanical strength. The amount of these binders to be used is usually 2 to 60 parts by mass with respect to 100 parts by mass of the preliminarily calcined powder, and the amount of the glycerin aqueous solution is preferably 15 to 50 parts by mass. The binder and the preliminarily calcined powder may be alternately supplied to a molding machine or simultaneously supplied to the molding machine on the occasion of the carrying. Further, on the occasion of molding, a small amount of known additives such as graphite and talc may be added. None of a molding aid, a pore-forming agent and a carrier added in the molding is considered as the constituent element of the active component in the second aspect, regardless of whether the molding aid, the pore-forming agent and the carrier have the activity in the sense of converting the raw material into some other product.

The preliminary calcination method, the preliminary calcination conditions, the main calcination method, and the main calcination conditions are not limited, but known treatment methods and conditions can be applied. The preliminary calcination or the main calcination is usually carried out at 200° C. or higher and 600° C. or lower, and preferably 300° C. or higher and 550° C. or lower, for 0.5 hours or longer, and preferably 1 hour or longer and 40 hours or shorter under the conditions that an oxygen-containing gas such as air or an inert gas flow. Here, the inert gas refers to a gas that does not reduce the reaction activity of the catalyst, and specific examples thereof include nitrogen, carbon dioxide, helium and argon. The optimum conditions for the main calcination vary depending on the reaction conditions when an unsaturated aldehyde and/or an unsaturated carboxylic acid are produced using a catalyst, and changing the process parameters of the main calcination step, that is, the oxygen content in the atmosphere, the maximum temperature reached and the calcination time falls within the scope of the second aspect, because the changing is well-known for the skilled person. The main calcination step shall be carried out after the above preliminary calcination step, and the maximum temperature reached (main calcination temperature) in the main calcination step shall be higher than the maximum temperature reached (preliminary calcination temperature) in the above preliminary calcination step. The technique of the calcination includes but not limited to a fluidized bed, rotary kiln, muffle furnace, and tunnel firing furnace, and should be selected within an appropriate range in consideration of the final catalyst performance, mechanical strength, molding properties, production efficiency and the like.

The production method of the second aspect is preferably used as a method for producing an unsaturated aldehyde compound, an unsaturated carboxylic acid compound, or a conjugated diene compound, is more preferably used as a method for producing an unsaturated aldehyde compound, and is particularly preferably used as a method for producing acrolein from propylene. In a process of an exothermic reaction such as production of an unsaturated aldehyde compound, an unsaturated carboxylic acid compound, or a conjugated diene compound, it is known to those skilled in the art that different catalyst types are filled in multiple layers so that the activity is increased from an inlet side of a reaction tube toward an outlet side of the reaction tube, for the purpose of preventing deterioration of the catalyst itself due to heat generated by the reaction in an actual plant. The second aspect can be performed by either single-layer filling or multi-layer filling, but two-layer or three-layer filling is particularly preferred.

[Catalyst in Second Stage]

In the production method of the second aspect, for example, when the above catalyst is used as a catalyst in a first stage, that is, used as a catalyst for producing an unsaturated aldehyde compound, an unsaturated carboxylic acid compound can be obtained by performing a second-stage oxidation reaction.

In this case, the catalyst described above can also be used as a catalyst in a second stage, but a catalyst containing a catalytically active component represented by the following formula (II-B) is preferred.

$$Mo_{12}V_{a4}W_{b4}Cu_{c4}Sb_{d4}X4_{e4}Y4_{f4}Z4_{g4}O_{h4} \qquad \text{(II-B)}$$

(in the formula, Mo, V, W, Cu, Sb and O represent molybdenum, vanadium, tungsten, copper, antimony and oxygen, respectively; X4 represents at least one element selected from the group consisting of an alkali metal and thallium; Y4 represents at least one element selected from the group consisting of magnesium, calcium, strontium, barium and zinc; and Z4 represents at least one element selected from the group consisting of niobium, cerium, tin, chromium, manganese, iron, cobalt, samarium, germanium, titanium and arsenic. a4, b4, c4, d4, e4, f4, g4 and h4 represent the atomic proportion of each element, and with respect to molybdenum atom 12, a4 satisfies $0 < a4 \leq 10$, b4 satisfies $0 \leq b4 \leq 10$, c4 satisfies $0 < c4 \leq 6$, d4 satisfies $0 < d4 \leq 10$, e4 satisfies $0 \leq e4 \leq 0.5$, f4 satisfies $0 \leq f4 \leq 1$, and g4 satisfies $0 \leq g4 < 6$. Further, h4 is the number of oxygen atoms required to satisfy the atomic value of each component).

In the production of a catalyst containing the catalytically active component represented by the above formula (II-B), a method widely known as a method for preparing this kind of a catalyst, for example, an oxide catalyst or a catalyst having a heteropolyacid or a salt structure thereof, can be adopted. The raw materials that can be used in producing the catalyst are not limited, and various materials can be used. For example, molybdenum oxides such as molybdenum trioxide, molybdic acid or salts thereof such as molybdic acid and an ammonium molybdate, molybdenum-containing heteropolyacids or salts thereof such as phosphomolybdic acid and silicomolybdic acid, and the like can be used. The raw material of an antimony component is not limited, but antimony trioxide or antimony acetate is preferred. As raw materials for other elements such as vanadium, tungsten, copper and the like, nitrate, sulfate, carbonate, phosphate, organic acid salt, halide, hydroxide, oxide or the metal of these elements can be used.

A compound containing these active components may be used alone or in combination of two or more.

Next, the slurry liquid obtained above is dried to obtain a solid of catalytically active component. The drying method is not limited so long as the slurry liquid can be completely dried by the method. However, examples thereof include drum drying, freeze drying, spray drying and evaporation drying. Spray drying is preferred because the slurry liquid can be dried into a powder or granule in a short period of time. The temperature of the drying with spray drying varies depending on the concentration of the slurry liquid, the liquid sending speed or the like, but the temperature at the outlet of a drying machine is approximately 70° C. to 150° C. In this case, the slurry liquid is preferably dried such that the average particle size of a slurry liquid dried product (catalyst precursor) to be obtained is 10 μm to 700 μm.

The solid of catalytically active component in the second stage obtained as described above can be used as it is for a coating mixture, and is preferably subjected to calcination because the molding properties may be improved. The calcination method and the calcination conditions are not limited, and known treatment methods and conditions can be applied. The optimum calcination conditions vary depending on the used raw material for the catalyst, catalyst composition, preparation method and the like. The calcination temperature is usually 100° C. to 350° C., preferably 150° C. to 300° C., and the calcination time is usually 1 to 20 hours. The calcination is usually carried out in an air atmosphere, but may be carried out in an atmosphere of an inert gas such as nitrogen, carbon dioxide, helium or argon. The calcination in an air atmosphere may be carried out after calcination in an inert gas atmosphere, if necessary. The thus-obtained calcined solid is preferably pulverized before the molding. The pulverizing method is not limited, but it is preferable to use a ball mill.

The compound containing the active component in preparing the slurry for the second stage does not necessarily have to contain all the active components, and a part of the components may be used before the following molding step.

The shape of the catalyst in the second stage is not limited. The catalyst is used by being molded into a columnar shape, a tablet, a ring shape, a spherical shape or the like in order to reduce the pressure loss of a reaction gas in the oxidation reaction. Among these, the solid of catalytically active component is particularly preferably carried on an inert carrier to be a carried catalyst because improvement in selectivity and removal of heat of reaction can be expected. A tumbling granulation method described below is preferred for the carrying. This method is a method in which, for example, in a device that has a flat or uneven disk at the bottom of a fixed container, a carrier in the container is vigorously agitated by repeatedly performing rotation motion and revolution motion by rotating the disk at a high speed, and then a mixture for the carrying including the binder, the solid of catalytically active component and optionally a molding aid and/or a strength improver is carried on the carrier. As a method of adding the binder, any methods may be adapted such as 1) premixing a binder with the mixture for the carrying, 2) adding the binder at the same time as the mixture for the carrying is added into the fixed container, 3) adding the binder after adding the mixture for the carrying into the fixed container, 4) adding the binder before adding the mixture for the carrying into the fixed container, 5) dividedly preparing the mixture for the carrying and the binder independently and adding the whole amount of them in the appropriate combination of 2) to 4). Among these, for example, 5) is preferably performed by adjusting the adding rate using an auto feeder or the like such that the mixture for the carrying does not adhere to the wall of the fixed container and the mixture for the carrying does not aggregate with each other and a predetermined amount of the mixture for the carrying is carried on the carrier. Examples of the binder include water, ethanol, polyhydric alcohol, polyvinyl alcohol as a polymer-based binder, celluloses such as a crystalline cellulose, methyl cellulose and ethyl cellulose, and an aqueous silica sol solution as an inorganic binder. Diols such as cellulose and ethylene glycol and triols such as glycerin are preferred, and an aqueous solution having a concentration of glycerin of 5 mass % or more is particularly preferred. The amount of these binders to be used is usually 2 to 60 parts by mass, preferably 10 to 50 parts by mass, per 100 parts by mass of the mixture for the carrying.

Specific examples of the carrier in the above carrying include a spherical carrier having a diameter of 1 mm to 15 mm, and preferably 2.5 mm to 10 mm, such as silicon carbide, alumina, silica alumina, mullite and arandom. The carriers having a porosity of 10% to 70% are usually used. The carrier and the mixture for the carrying at the ratio of the mixture for the carrying/(mixture for the carrying+carrier) =10 mass % to 75 mass % are usually used, and the carrier and the mixture for the carrying at the ratio of the mixture for the carrying/(mixture for the carrying+carrier)=15 mass % to 60 mass % are preferably used. When the ratio of the mixture for the carrying tends to be large, the reaction activity of the carried catalyst is large, but the mechanical strength tends to be small. On the contrary, when the ratio of the mixture for the carrying is small, the mechanical strength tends to be large, but the reaction activity tends to be small. In the above, examples of the molding aid to be used as necessary include silica gel, diatomite, and alumina powder. The amount of the molding aid to be used is usually 1 to 60 parts by mass with respect to 100 parts by mass of the solid of catalytically active component. If necessary, the use of inorganic fibers (for example, ceramic fibers or whiskers) that are inactive to the solid of catalytically active component and the reaction gas as the strength improver is useful for improving the mechanical strength of the catalyst, and glass fibers are preferred. The amount of the fiber to be used is usually 1 to 30 parts by mass with respect to 100 parts by mass of the solid of catalytically active component. None of a molding aid, a pore-forming agent and a carrier added in the molding of the catalyst for the first stage is considered as the constituent element of the active component in the second aspect, regardless of whether the molding aid, the pore-forming agent and the carrier have the activity in the sense of converting the raw material into some other product.

The carried catalyst obtained as described above can be used as a catalyst for the catalytic gas phase oxidation, and is preferably subjected to calcination because the molding properties may be improved. The calcination method and the calcination conditions are not limited, and known treatment methods and conditions can be applied. The optimum calcination conditions vary depending on the raw material for the catalyst to be used, the catalyst composition, the preparation method, and the like, but the calcination temperature is usually 100° C. to 450° C., preferably 270° C. to 420° C., and the calcination time is usually 1 to 20 hours. The calcination is usually carried out in an air atmosphere, and may be carried out in an atmosphere of an inert gas such as nitrogen, carbon dioxide, helium or argon. The calcination in an air atmosphere may be carried out after the calcination in an inert gas atmosphere, if necessary.

When the catalyst of the second aspect is used in a reaction of using propylene, isobutylene, t-butyl alcohol and the like as raw materials to produce the corresponding unsaturated aldehyde, unsaturated carboxylic acid, and particularly, in a reaction of producing acrolein and acrylic acid by catalytic gas phase oxidation of propylene with molecular oxygen or a gas containing molecular oxygen, using the catalyst of the second aspect allows for improving the catalytic activity and the yield, and is very effective in improving the price competitiveness of the product as compared with the known method. In addition, the effect of improving the process stability of the partial oxidation reaction accompanied by heat generation, such as reduction of the hot spot temperature can be expected. Further, the catalyst of the second aspect is also effective in reducing by-products that adversely influences the environment and the quality of the final product, such as carbon monoxide (CO), carbon dioxide ($CO_2$), acetaldehyde, acetic acid, and formaldehyde.

The thus-obtained catalyst of the second aspect can be used, for example, for producing acrolein and/or acrylic acid by catalytic gas phase oxidation of propylene using a molecular oxygen-containing gas. In the production method of the second aspect, the method for flowing the raw material gas may be an ordinary single-flow method or a recycling method, and can be carried out under widely used conditions, and is not limited. For example, a mixed gas containing 1 vol % to 10 vol % and preferably 4 vol % to 9 vol % of propylene, 3 vol % to 20 vol % and preferably 4 vol % to 18 vol % of molecular oxygen, 0 vol % to 60 vol % and preferably 4 vol % to 50 vol % of water vapor at room temperature as a starting raw material, and 20 vol % to 80 vol % and preferably 30 vol % to 60 vol % of an inert gas such as carbon dioxide and nitrogen is introduced to the catalyst of the second aspect filled in a reaction tube at 250°

C. to 450° C. under normal pressure to 10 atm and a space velocity of 300 to 5000 h$^{-1}$ to perform a reaction.

In the second aspect, unless otherwise specified, the improvement of the catalytic activity means that the conversion rate of the raw material is high when the catalytic reaction is carried out at the same salt bath temperature.

In the second aspect, unless otherwise specified, a high yield means that the total yield of the corresponding unsaturated aldehyde and/or unsaturated carboxylic acid is high when the oxidation reaction is performed using propylene, isobutylene, t-butyl alcohol, and the like as raw materials. Unless otherwise specified, the yield refers to a useful yield described later.

In the second aspect, unless otherwise specified, the constituent elements of the catalytically active component refer to all the elements to be used in the method for producing a catalyst, but the raw materials and the constituent elements thereof that disappear, sublimate, volatilize, and burn at the maximum temperature or lower in the main calcination step are not included in the constituent elements of the catalytically active component. Further, silicon and the other elements constituting inorganic materials contained in the molding aid and the carrier in the shaping step are not included in the constituent elements of the catalytically active component.

In the second aspect, the hot spot temperature refers to the maximum temperature in the temperature distribution in the catalyst-filled bed that is measured in thermocouples installed in the multi-tube reaction tube in the long axis direction, and the salt bath temperature refers to a set temperature of a heat medium used for the purpose of cooling the heat generated in the reaction tube. The number of measuring points in the temperature distribution is not limited, but for example, the catalyst filling length is evenly divided from 10 to 1000. Further, in the measurement of the hot spot temperature, it is well-known to the skilled person that a temperature sensor sheath is installed in a long axis direction of the reaction tube, and the thermocouple is installed therein, for the purpose of stabilizing the measurement by the thermocouple. An outer diameter of the temperature sensor sheath is not limited, but is, for example, preferably 7 mm or less, more preferably 6 mm or less, and even more preferably 3.5 mm or less, and the outer diameter of the thermocouple is also not limited, but is, for example, preferably 6 mm or less, more preferably 4 mm or less, and even more preferably 3 mm or less.

In the second aspect, the unsaturated aldehyde and the unsaturated aldehyde compound refers to organic compounds having at least one double bond and at least one aldehyde in the molecule, such as acrolein and methacrolein. In the second aspect, the unsaturated carboxylic acid and the unsaturated carboxylic acid compound refers to organic compounds having at least one double bond and at least one carboxy group or an ester group of the carboxyl group in the molecule, and are, for example, acrylic acid, methacrylic acid, and methyl methacrylate. In the second aspect, the conjugated diene refers to a diene in which a double bond is separated by one single bond and which is chemically conjugated, and is, for example, 1,3-butadiene.

Further, the production method of the second aspect allows the reaction process to be stably maintained from the reason that (1) the hot spot temperature is reduced and (2) the activity of the catalyst is stable even when the salt bath temperature is low.

[[Third Aspect]]

A third aspect of the present invention relates to a method for filling a catalyst, the method including filling a composite metal oxide catalyst containing molybdenum, bismuth, and cobalt as an essential component such that two or more layers are stacked in a tube axis direction for multi-layer filling, in which a composition of the composite metal oxide catalyst contained in one catalyst layer is different from a composition of the composite metal oxide catalyst contained in at least one of the other catalyst layers, in which a ratio of a component amount of bismuth to a component amount of molybdenum in a catalyst layer closest to a gas inlet side of a tube axis is smaller than a ratio of a component amount of bismuth to a component amount of molybdenum in a catalyst layer closest to a gas outlet side of the tube axis, and in which, in any of two catalyst layers adjacent to each other, the catalysts are filled such that a ratio of the component amount of bismuth to the component amount of molybdenum in a catalyst layer on the gas inlet side of the tube axis is equal to or smaller than a ratio of the component amount of bismuth to the component amount of molybdenum in a catalyst layer on the gas outlet side of the tube axis.

Filling the catalyst as described above is very effective in improving the catalytic activity and the yield in a catalytic gas phase oxidation or a catalytic gas phase oxidation dehydrogenation, and allows for improving the yield of a target product when propylene, isobutylene, t-butyl alcohol, or the like as a raw material are used to produce a corresponding unsaturated aldehyde or unsaturated carboxylic acid.

[Catalyst Layer Closest to Inlet Side of Tube Axis and Catalyst Layer Closest to Outlet Side of Tube Axis]

The catalyst layer closest to the inlet side of the tube axis means, for example, a first catalyst layer from the inlet side for the raw material gas such as propylene, isobutylene, t-butyl alcohol, or 1,3-butene when n-layered catalyst layers are provided. The catalyst layer closest to the outlet side means the n-th catalyst layer.

The third aspect has a characteristic that the ratio of the component amount of bismuth when the component amount of molybdenum in the catalyst layer closest to the inlet side (first layer) is taken as 12 is smaller than the ratio of the component amount of bismuth when the component amount of molybdenum in the catalyst layer closest to the outlet side (n-th layer) is taken as 12. The difference thereof (=gas inlet side−gas outlet side) is preferably −2.0 or more and less than 0.0. The lower limit thereof is more preferably −1.5, −1.2, −1.0, −0.8, −0.6, or −0.4 in preferred order, and particularly preferably −0.2. That is, the most preferred range is −0.2 or more and less than 0.0. Further, a ratio of Bi in these catalyst layers (=gas inlet side/gas outlet side) is preferably 0.01 or more and less than 1.00. The lower limit thereof is 0.05, 0.10, 0.20, 0.30, 0.40, 0.50, 0.60, 0.70, or 0.80 in preferred order, and the upper limit thereof is 0.99, 0.95, or 0.90 in preferred order. That is, the most preferred range is 0.80 or more and 0.90 or less.

In addition, the third aspect has a characteristic that, in any of the two catalyst layers adjacent to each other, the ratio of the component amount of bismuth when the component amount of molybdenum in the catalyst layer on the gas inlet side of the tube axis is taken as 12 is equal to or smaller than the ratio of the component amount of bismuth when the component amount of molybdenum in the catalyst layer on the gas outlet side of the tube axis is taken as 12. The difference between the ratio of the component amount of bismuth on the gas inlet side and the ratio of the component amount of bismuth on the gas outlet side in the two catalyst layers adjacent to each other (=gas inlet side−gas outlet side) is preferably −2.0 or more and 0.0 or less when the atomic proportion of molybdenum is taken as 12. The lower limit thereof is −1.5, −1.2, −1.0, −0.8, −0.6, or −0.4 in preferred order, and most preferably −0.2. Further, the ratio of Bi in these catalyst layers (=gas inlet side/gas outlet side) is preferably 0.01 or more and 1.00 or less. The lower limit thereof is 0.05, 0.10, 0.20, 0.30, 0.40, 0.50, 0.60, 0.70, or 0.80 in preferred order, and the upper limit thereof is 0.99, 0.95, or 0.90 in preferred order. That is, the most preferred range is 0.80 or more and 0.90 or less.

These features allow for achieving a high yield of the catalytic gas phase oxidation.

[Sum (S) of Ratios of Peak Intensities in X-Ray Diffraction Pattern]

The method for filling a catalyst of the third aspect is characterized in a relationship between the catalysts of the respective catalyst layers. Specifically, the method for filling a catalyst is characterized in a sum (S) of ratios of peak intensities at $2\theta=14.1°±0.1°$, $25.4°±0.1°$, and $28.5°±0.1°$ to a peak intensity at $2\theta=26.5°±0.1°$ in an X-ray diffraction pattern obtained by using CuKα rays as an X-ray source. The peak intensity at $2\theta=26.5°±0.1°$ means a maximum value of a peak observed in a range of $2\theta=26.5°±0.1°$, and the nature of the peak intensity indicates a peak height of a crystal phase of β-CoMo. Similarly, the peak intensities at $2\theta=14.1°±0.1°$, $25.4°±0.1°$, and $28.5°±0.1°$ indicate a peak height of a crystal phase of α-CoMo. That is, nature of the third aspect is that the catalyst exhibits a high yield by being filled such that the peak intensity of the crystal phase of α-CoMo observed at $2\theta=14.1°±0.1°$, $25.4°±0.1°$, and $28.5°±0.1°$ with respect to the peak intensity of the crystal phase of β-CoMo observed at $2\theta=26.5°±0.1°$ is within a certain range. As will be described later, since the peak intensity of the crystal phase of α-CoMo, more specifically, the peak intensity of each crystal plane changes depending on the composition and the production method of the catalyst, the sum of the peak intensities of specific crystal planes among α-CoMo is particularly important. The peaks corresponding to the specific crystal planes appear at $2\theta=14.1°±0.1°$, $25.4°±0.1°$, and $28.5°±0.1°$ described above, and nature of the third aspect is to find a relationship between the filling method related to a parameter S and the catalytic performance. More specifically, the sum (S) of ratios of peak intensities is expressed by the following formula.

$$\text{Sum } (S) \text{ of ratios of peak intensities} = \{(\text{peak intensity at } 2\theta=14.1°±0.1°) + (\text{peak intensity at } 2\theta=25.4°±0.1°) + (\text{peak intensity at } 2\theta=28.5°±0.1°)\} / (\text{peak intensity at } 2\theta=26.5°±0.1°) \times 100$$

The method for filling a catalyst found by the inventors is a method for filling a catalyst layer containing a composite metal oxide catalyst containing molybdenum, bismuth, and cobalt as an essential component, in which the catalysts are filled such that two or more layers are stacked in a tube axis direction for multi-layer filling, and the catalysts are filled such that, with respect to the ratio (S) of the peak intensity of the catalyst contained in one catalyst layer in an X-ray diffraction pattern obtained by using CuKα rays as an X-ray source, the ratio (S) of the peak intensity of the catalyst contained in the catalyst layer closest to the gas outlet side of the tube axis is smaller than the ratio (S) of the peak intensity of the catalyst contained in the catalyst layer closest to the gas inlet side of the tube axis, and in any of two catalyst layers adjacent to each other, the ratio (S) of the peak intensity of the catalyst contained in the catalyst layer on the gas outlet side of the tube axis is equal to or smaller than the ratio (S) of the peak intensity of the catalyst contained in the catalyst layer on the gas inlet side of the tube axis.

The difference between S on the gas inlet side and S on the gas outlet side in the two catalyst layers adjacent to each other (=gas inlet side−gas outlet side) is preferably 0.0 or more and 50.0 or less. The lower limit thereof is preferably 0.5, 1.0, 2.5, 5.0, 10.0, or 15.0 in preferred order, and particularly preferably 20.0. The upper limit thereof is preferably 45.0 or 40.0 in preferred order, and particularly preferably 37.0. That is, the most preferred range of the difference between S on the gas inlet side and S on the gas outlet side in the two catalyst layers adjacent to each other is 20.0 or more and 37.0 or less. In the case of filling with three or more layers, there may be two or more values as the difference between S on the gas inlet side and S on the gas outlet side in the two catalyst layers adjacent to each other. In this case, it is a particularly preferable filling method that all of the differences fall within the above range.

In addition, the method for filling a catalyst in the third aspect is preferably a method in which the catalysts are filled such that two or more layers are stacked in a tube axis direction for multi-layer filling, and the catalysts are filled such that, with respect to a ratio (S1) of a peak intensity of the catalyst contained in one catalyst layer, which is expressed by the following formula in an X-ray diffraction pattern obtained by using CuKα rays as an X-ray source, the ratio (S1) of a peak intensity of the catalyst contained in the catalyst layer closest to the gas outlet side of the tube axis is smaller than the ratio (S1) of a peak intensity of the catalyst contained in the catalyst layer closest to the gas inlet side of the tube axis. Further, the method for filling a catalyst is preferably a method in which, in any of the two catalyst layers adjacent to each other, the catalysts are filled such that the ratio (S1) of a peak intensity of the catalyst contained in the catalyst layer on the gas outlet side of the tube axis is the equal to or smaller than the ratio (S1) of a peak intensity of the catalyst contained in the catalyst layer on the gas inlet side of the tube axis.

$$S1 = (\text{peak intensity at } 2\theta = 14.1° \pm 0.1°)/(\text{peak intensity at } 2\theta = 26.5° \pm 0.1°) \times 100$$

The difference between S1 on the gas inlet side and S1 on the gas outlet side in the two catalyst layers adjacent to each other (=gas inlet side−gas outlet side) is preferably 1.0 or more and 50.0 or less. The lower limit thereof is preferably 1.5, 2.5, 5.0, 7.5, or 10.0 in preferred order, and particularly preferably 12.0. The upper limit thereof is preferably 40.0, 30.0, 25.0, or 20.0 in preferred order, and particularly preferably 17.0. That is, the most preferred range of the difference between S1 on the gas inlet side and S1 on the gas outlet side in the two catalyst layers adjacent to each other is 12.0 or more and 17.0 or less. In the case of filling with three or more layers, there may be two or more values as the difference between S1 on the gas inlet side and S1 on the gas outlet side in two catalyst layers adjacent to each other. In this case, it is a particularly preferable filling method that all of the differences fall within the above range.

In addition, the method for filling a catalyst in the third aspect is preferably a method in which the catalysts are filled such that two or more layers are stacked in a tube axis direction for multi-layer filling, and the catalysts are filled such that, with respect to a ratio (S2) of a peak intensity of the catalyst contained in one catalyst layer, which is expressed by the following formula in an X-ray diffraction pattern obtained by using CuKα rays as an X-ray source, the ratio (S2) of a peak intensity of the catalyst contained in the catalyst layer closest to the gas outlet side of the tube axis is smaller than the ratio (S2) of a peak intensity of the catalyst contained in the catalyst layer closest to the gas inlet side of the tube axis. Further, the method for filling a catalyst is preferably a method in which, in any of the two catalyst layers adjacent to each other, the catalysts are filled such that the ratio (S2) of a peak intensity of the catalyst contained in the catalyst layer on the gas outlet side of the tube axis is the equal to or smaller than the ratio (S2) of a peak intensity of the catalyst contained in the catalyst layer on the gas inlet side of the tube axis.

$$S2 = (\text{peak intensity at } 2\theta = 25.4° \pm 0.1°)/(\text{peak intensity at } 2\theta = 26.5° \pm 0.1°) \times 100$$

The difference between S2 on the gas inlet side and S2 on the gas outlet side of the two catalyst layers adjacent to each other (=gas inlet side−gas outlet side) is preferably 0.0 or more and 20.0 or less. The lower limit thereof is preferably 0.5, 1.0, 2.5, 3.0, or 3.5 in preferred order, and particularly preferably 4.0. The upper limit is preferably 18.0, 15.0, 12.0, 10.0, or 8.0 in preferred order, and particularly preferably 6.0. That is, the most preferred range of the difference between S2 on the gas inlet side and S2 on the gas outlet side of two adjacent catalyst layers is 4.0 or more and 6.0 or less. In the case of filling with three or more layers, there may be two or more values as the difference between S2 on the gas inlet side and S2 on the gas outlet side of the two catalyst layers adjacent to each other. In this case, it is a particularly preferable filling method that all of the differences fall within the above range.

In addition, the method for filling a catalyst in the third aspect is preferably a method in which the catalysts are filled such that two or more layers are stacked in a tube axis direction for multi-layer filling, and the catalysts are filled such that, with respect to a ratio (S3) of a peak intensity of the catalyst contained in one catalyst layer, which is expressed by the following formula in an X-ray diffraction pattern obtained by using CuKα rays as an X-ray source, the ratio (S3) of a peak intensity of the catalyst contained in the catalyst layer closest to the gas outlet side of the tube axis is smaller than the ratio (S3) of a peak intensity of the catalyst contained in the catalyst layer closest to the gas inlet side of the tube axis. Further, the method for filling a catalyst is preferably a method in which, in any of the two catalyst layers adjacent to each other, the catalysts are filled such that the ratio (S3) of a peak intensity of the catalyst contained in the catalyst layer on the gas outlet side of the tube axis is the equal to or smaller than the ratio (S3) of a peak intensity of the catalyst contained in the catalyst layer on the gas inlet side of the tube axis.

$$S3 = (\text{peak intensity at } 2\theta = 28.5° \pm 0.1°)/(\text{peak intensity at } 2\theta = 26.5° \pm 0.1°) \times 100$$

The difference between S3 on the gas inlet side and S3 on the gas outlet side of the two catalyst layers adjacent to each other (=gas inlet side−gas outlet side) is preferably 0.0 or more and 20.0 or less. The lower limit thereof is 0.5, 1.0, 2.5, or 3.0 in preferred order, and particularly preferably 3.5. The upper limit thereof is 18.0, 15.0, 12.0, 10.0, or 8.0 in preferred order, and particularly preferably 5.0. That is, the most preferred range of the difference between S3 on the gas inlet side and S3 on the gas outlet side of two adjacent catalyst layers is 3.5 or more and 5.0 or less. In the case of filling with three or more layers, there may be two or more values as the difference between S3 on the gas inlet side and S3 on the gas outlet side of the two catalyst layers adjacent to each other. In this case, it is a particularly preferable filling method that all of the differences fall within the above range.

Examples of a method of measuring an X-ray diffraction angle ($2\theta$) include measuring the X-ray diffraction angle ($2\theta$) under conditions of X-ray CuK$\alpha$ rays ($\lambda$=0.154 nm), an output of 40 kV, 30 mA, a measurement range of 10° to 60°, and a measurement speed of 10° per minute by using Ultima IV manufactured by Rigaku Corporation, but the method is not limited thereto as long as the method does not depart from the measurement principle. For the sum (S) of ratios of peak intensities calculated in the third aspect, the calculation is performed after the background and halo patterns described in Patent Literature 3 have been eliminated from the X-ray diffraction pattern before the calculation. When each of the peaks does not have a clear local maximum value in the corresponding range of 20 or does not have a peak shape, or when it is not determined that the peak is a clear peak due to too much noise, or when the peak has a local minimum value in the range of 20 for calculating the local maximum value of the peak, the peak intensity is assumed to be 0 in the third aspect.

The range of the parameter S of each catalyst to be used in the filling method of the third aspect is preferably 42 or more and 113 or less. In addition, the upper limit value of the parameter S is 110, 105, 100, 95, 90, 85, 80, or 75 in more preferred order, and most preferably 70, and the lower limit value of the parameter S is 44, 46, 48, 50, 52, 53, 54, or 60 in more preferred order, and most preferably 65. That is, a preferred range of the sum (S) of ratios of peak intensities is set by the upper and lower limits, for example, 44 or more and 110 or less, and most preferably 65 or more and 70 or less. Preferably, any one of the catalysts to be used in the third aspect satisfies the range of S, but all of the catalysts most preferably satisfy the range.

Further, each catalyst to be used in the filling method of the third aspect preferably has an optimum range for the ratio S1 of a peak intensity expressed by the following formula. The lower limit thereof is 5, 10, 14, 16, 18, or 20 in preferred order, and most preferable 21, and the upper limit thereof is 42, 40, 36, 32, or 30 in preferred order, and most preferable 28. That is, the most preferred range of 51 is 21 or more and 28 or less. Preferably, any one of the catalysts used in the third aspect satisfies the range of S1, but all of the catalysts most preferably satisfy the range.

$$S1 = (\text{peak intensity at } 2\theta = 14.1° \pm 0.1°)/(\text{peak intensity at } 2\theta = 26.5° \pm 0.1°) \times 100$$

Each catalyst to be used in the filling method of the third aspect preferably has an optimum range for the ratio S2 of a peak intensity expressed by the following formula. The lower limit thereof is 2, 4, 6, 8, 10, 12, or 14 in preferred order, and most preferable 15, and the upper limit thereof is 20, and most preferable 18. That is, the most preferred range of S2 is 15 or more and 18 or less. Preferably, any one of the catalysts used in the third aspect satisfies the range of S2, but all of the catalysts most preferably satisfy the range.

$$S2 = (\text{peak intensity at } 2\theta = 25.4° \pm 0.1°)/(\text{peak intensity at } 2\theta = 26.5° \pm 0.1°) \times 100$$

Each catalyst to be used in the filling method of the third aspect preferably has an optimum range for the ratio S3 of a peak intensity expressed by the following formula. The lower limit thereof is 10, 15, 20, 22, 24, or 26 in preferred order, and most preferably 27, and the upper limit thereof is 44, 42, 40, 38, 36, 34, or 32 in preferred order, and most preferably 31. That is, the most preferred range of S3 is 27 or more and 31 or less. Preferably, any one of the catalysts used in the third aspect satisfies the range of S3, but all of the catalysts most preferably satisfy the range.

$$S3 = (\text{peak intensity at } 2\theta = 28.5° \pm 0.1°)/(\text{peak intensity at } 2\theta = 26.5° \pm 0.1°) \times 100$$

Each catalyst to be used in the filling method of the third aspect preferably has a peak at $2\theta = 27.4° \pm 0.1°$ in addition to the peak in an X-ray diffraction pattern obtained by using CuK$\alpha$ rays as an X-ray source. When the peak intensity is within a specific range, the catalyst is more preferable. When the peak intensity is defined as S4, the lower limit thereof is 2, 4, 6, 8 in preferred order, and most preferably 9, and the upper limit thereof is 16, 15, or 14 in preferred order, and most preferably 13. That is, a preferred range of S4 is 2 or more and 16 or less, and a most preferred range thereof is 9 or more and 13 or less. Preferably, any one of the catalysts used in the third aspect satisfies the range of S4, but all of the catalysts most preferably satisfy the range.

$$S4 = (\text{peak intensity at } 2\theta = 27.4° \pm 0.1°)/(\text{peak intensity at } 2\theta = 26.5° \pm 0.1°) \times 100$$

[Catalyst Composition]

The catalytically active component contained in each catalyst used in the filling method of the third aspect preferably has a composition represented by the following formula (III-1). Preferably, any one of the catalysts used in the third aspect has a composition represented by the following formula (III-1), but all of the catalysts most preferably have a composition represented by the following formula (III-1).

$$Mo_{a5}Bi_{b5}Ni_{c5}Co_{d5}Fe_{e5}X5_{f5}Y5_{g5}Z5_{h5}O_{i5} \tag{III-1}$$

(in the formula, Mo, Bi, Ni, Co and Fe represent molybdenum, bismuth, nickel, cobalt and iron, respectively; X5 is at least one element selected from tungsten, antimony, tin, zinc, chromium, manganese, magnesium, silicon, aluminum, cerium and titanium; Y5 is at least one element selected from sodium, potassium, cesium, rubidium, and thallium; Z5 belongs to the 1st to 16th groups in the periodic table and means at least one element selected from elements other than the above Mo, Bi, Ni, Co, Fe, X5, and Y5; a5, b5, c5, d5, e5, f5, g5, h5, and i5 represent the number of atoms of molybdenum, bismuth, nickel, cobalt, iron, X5, Y5, Z5, and oxygen, respectively; when a5=12, $0 < b5 \leq 7$, $0 \leq c5 \leq 10$, $0 < d5 \leq 10$, $0 < c5 + d5 \leq 20$, $0 \leq e5 \leq 5$, $0 \leq g5 \leq 2$, $0 \leq f5 \leq 3$, $0 \leq h5 \leq 5$, and i5 is a value determined by an oxidation state of each element).

In the above formula (III-1), preferred ranges of b5 to i5 are as follows.

The lower limit of b5 is 0.2, 0.5, 0.7, or 0.8 in preferred order, and most preferably 0.9. The upper limit of b5 is 5, 3, 2, 1.6, 1.4, or 1.2 in preferred order, and most preferably 1.1. That is, the most preferred range of b5 is $0.9 \leq b5 \leq 1.1$.

The lower limit of c5 is 1, 2, 2.5, 2.8, or 3.0 in preferred order, and most preferably 3.1, and the upper limit of c5 is 5, 4, 3.8, 3.6, or 3.4 in preferred order, and most preferably 3.2. That is, the most preferred range of c5 is $3.1 \leq c5 \leq 3.2$.

The lower limit of d5 is 3, 4, 5, 5.3, 5.5, or 5.7 in preferred order, and most preferably 5.8, and the upper limit of d5 is 8, 7, 6.5, 6.3, or 6.1 in preferred order, and most preferably 6.0. That is, the most preferred range of d5 is $5.8 \leq d5 \leq 6.0$.

The lower limit of e5 is 0.5, 1, 1.2, or 1.4 in preferred order, and most preferably 1.5, and the upper limit of e5 is 4, 3, 2.5, 2, or 1.8 in preferred order, and most preferably 1.7. That is, the most preferred range of e5 is $1.5 \leq e5 \leq 1.7$.

The upper limit of f5 is 8, 7, 6, or 5 in preferred order. That is, the most preferred range of f5 is $0 \leq f5 \leq 5$.

The lower limit of g5 is 0, 0.02, 0.04, or 0.06 in preferred order, and most preferably 0.07, and the upper limit of g5 is 1.5, 1, 0.5, 0.2, or 0.15 in preferred order, and most preferably 0.10. That is, the most preferred range of g5 is $0.07 \leq g5 \leq 0.10$.

The upper limit of h5 is 8, 7, 6, or 5 in preferred order. That is, the most preferred range of h5 is $0 \leq h5 \leq 5$.

Y5 is preferably contained in two or less types, and one type is particularly preferred. Further, it is a particularly preferred embodiment that f5 and h5 are 0.

In the third aspect, as the catalyst composition to be used, a type or an element ratio of an alkali metal is particularly preferably different between the layer on the inlet side of the reaction tube and the layer on the outlet side of the reaction tube. Specifically, Z5 and/or h5 are made different in $Z5_{h5}$ in the above (III-1). For example, Z5 is cesium, or cesium and potassium in the layer closest to the inlet side and the second layer from the inlet side, and Z5 is potassium in the layer on the outlet side.

[Carrying]

The catalyst in which a preliminary calcined powder subjected to preliminary calcination after the preparation of the catalytically active component is carried on the inert carrier is particularly excellent as the catalyst to be used for the filling method of the third aspect.

As the material of the inert carrier, known materials such as alumina, silica, titania, zirconia, niobia, silica alumina, silicon carbide, carbides, and mixtures thereof can be used. Further, the particle size, water absorption rate, mechanical strength, crystallinity of each crystal phase, mixing ratio, etc. are not limited, and an appropriate range of these should be selected in consideration of the final catalyst performance, molding properties, production efficiency, etc. The mixing ratio of the carrier and the preliminarily calcined powder is calculated as the active mass ratio according to the following equation based on the charged mass of each raw material.

Active mass ratio (mass %)=(mass of preliminary calcined powder used for molding)/{(mass of preliminary calcined powder used for molding)+(mass of carrier used for molding)}×100

The upper limit of the active mass ratio is preferably 80 mass %, and more preferably 60 mass %.

The lower limit is preferably 20 mass %, and more preferably 30 mass %. That is, the most preferred range of the active mass ratio is 30 mass % or more and 60 mass % or less.

As the inert carrier, silica and/or alumina is preferable, and a mixture of silica and alumina is particularly preferable.

For the carrying, it is preferred to use a binder. Specific examples of the binder which can be used include water, ethanol, methanol, propanol, a polyhydric alcohol, polyvinyl alcohol as a polymer-based binder, and a silica sol aqueous solution as an inorganic binder; ethanol, methanol, propanol, and a polyhydric alcohol are preferred; a diol such as ethylene glycol and a triol such as glycerin is preferred; and an aqueous solution having a concentration of glycerin of 5 mass % or more is preferred. Using an appropriate amount of a glycerin aqueous solution allows for obtaining a high-performance catalyst having good molding properties and high mechanical strength. The amount of these binders used is usually 2 to 60 parts by mass with respect to 100 parts by mass of the preliminarily calcined powder. The amount of glycerin aqueous solution is preferably 10 to 30 parts by mass. The binder and the preliminarily calcined powder may be alternately or simultaneously supplied to a molding machine on the occasion of carrying.

For the means for controlling the value of S, the control can be performed by changing each condition in each production process described later, and examples thereof include (I) a method of changing a catalyst composition, (II) a method of changing a calcination condition, (III) a method of changing a condition of temperature decrease after calcination, (IV) a method of controlling a catalyst and a precursor thereof such that the catalyst and the precursor are not subjected to mechanical strength in all the steps of the production of the catalyst, (V) a method of using a raw material having high purity, other methods (VI) to (VIII), and a method of combining (I) to (VIII). The details of the methods (VI) to (VIII) will be described later.

Regarding the method (I), in the composition formula (III-1), the upper limit of e5/b5 is 1.90, and preferably 1.80; the lower limit of e5/b5 is 0.10, 0.50, 1.00, 1.40, or 1.50 in preferred order; the upper limit of d5/b5 is 9.0, 8.0, 7.0, or 6.0 in preferred order; the lower limit of d5/b5 is 2.0, 3.0, 4.0, 5.0, or 5.5 in preferred order; the upper limit of c5/e5 is 4.0, 3.0, or 2.5 in preferred order; the lower limit of c5/e5 is 1.5, 1.7, or 1.9 in preferred order; the upper limit of c5/d5 is 2.0, 1.0, or 0.8 in preferred order; the lower limit of c5/d5 is 0.4 or 0.5 in preferred order; the upper limit of g5/d5 is 0.10, 0.05, 0.04, or 0.03 in preferred order; the lower limit of g5/d5 is 0.01; the upper limit of g5/c5 is 0.041 or 0.039 in preferred order; and the lower limit of g5/c5 is 0.017, 0.019 or 0.021 in preferred order.

Regarding the method (II), in preliminary calcination and main calcination as described later, and both of them, a temperature is 200° C. or more and 600° C. or less, preferably 300° C. or more and 550° C. or less, and more preferably 460° C. or more and 550° C. or less, and the time for the calcination is 0.5 hours or more, preferably 1 hour or more and 40 hours or less, more preferably 2 hours or more and 15 hours or less, and most preferably 2 hours or more and 9 hours or less, and as an atmosphere, the oxygen concentration is 10 vol % or more and 40 vol % or less, preferably 15 vol % or more and 30 vol % or less, and the atmosphere is most preferably an air atmosphere.

Regarding the method (III), in the preliminary calcination and the main calcination as described later, and both of them, a rate of decrease (rate of temperature decrease) of the temperature of a catalyst surface from the maximum temperature (preliminary calcination temperature or main calcination temperature) reached in the calcination step to the room temperature is 1° C./min or more and 200° C./min or less, preferably 5° C./min or more and 150° C./min or less, more preferably 10° C./min or more and 120° C./min or less, and most preferably 50° C./min or more and 100° C./min or less. In order to achieve the range of the rate of temperature decrease described above, a temperature drop method generally industrially taken out, for example, a method of exposing a catalyst after calcination taken out from a calcination furnace to an inert atmosphere or a mist of an inert solvent, and a method of rapidly moving a catalyst after calcination into a room sufficiently cooled in advance are all included in the third aspect.

The method (IV) is a method of controlling a catalyst precursor and/or granules formed in each step to be described later such that the catalyst and the precursor are not subjected to a mechanical impact, a shear stress, and the like, and the preferred range of the mechanical impact, shear stress, and the like is controlled to 100 kgf or less, preferably 50 kgf or less, more preferably 20 kgf or less, still more preferably 10 kgf or less, and most preferably 5 kgf or less.

The method (VII) is a method of controlling a time during which a cobalt raw material and a nickel raw material are mixed, reacted, slurried, and retained in a mixing pot to be as short as possible in the step of preparing the catalyst to be described later, and more specifically, is a method of shortening the retention time in a state in which a metal salt raw material excluding molybdenum and alkali metal is not in the mixing pot and the cobalt raw material and the nickel raw material are present in the mixing pot, or a method of shortening the retention time in a state in which the cobalt raw material and the nickel raw material are present in the mixing pot when a pH in the mixing pot falls within a specific range. The retention time is preferably 24 hours, more preferably 1 hour, still more preferably 30 minutes, and most preferably 10 minutes. The range of pH is 1 or more and 14 or less, preferably 2 or more and 10 or less, more preferably 2 or more and 8 or less, and most preferably 3 or more and 7 or less. The same applies to an iron raw material and a bismuth raw material, a molybdenum raw material, and a bismuth raw material.

The method (VI), as described later, is, for example, a method in which a catalyst precursor is once obtained as granules and the granules are molded. Obtaining the catalyst precursor in the form of granules allows for producing the catalyst such that each component of the catalyst can be more uniform.

The method (VII) is a method of controlling a time during which a cobalt raw material and a nickel raw material are mixed, reacted, slurried, and retained in a mixing pot to be as short as possible in the step of preparing the catalyst to be described later, and more specifically, is a method of shortening the retention time in a state in which a metal salt raw material excluding molybdenum and alkali metal is not in the mixing pot and the cobalt raw material and the nickel raw material are present in the mixing pot, or a method of shortening the retention time in a state in which the cobalt raw material and the nickel raw material are present in the mixing pot when a pH in the mixing pot falls within a specific range. The retention time is preferably 24 hours, more preferably 1 hour, still more preferably 30 minutes, and most preferably 10 minutes. The range of pH is 1 or more and 14 or less, preferably 2 or more and 10 or less, more preferably 2 or more and 8 or less, and most preferably 3 or more and 7 or less. The same applies to an iron raw material and a bismuth raw material, a molybdenum raw material, and a bismuth raw material.

The method (VIII) is a method in which each raw material is undividedly charged at once in the preparing step, or a method in which the concentration of nitric acid in a mixed solution is decreased, in the step of preparing a catalyst to be described later. The method of charging each raw material at once means charging a next raw material after charging all the necessary amount of a raw material. Regarding the concentration of nitric acid in the mixed solution, the concentration of nitric acid ions in terms of mass % in the prepared solution when the preparation is completed and before the process proceeds to the next step is preferably 40 mass % or less, more preferably 35 mass % or less, still more preferably 30 mass % or less, and most preferably 25 mass % or less.

[Method for Producing Catalyst]

A starting raw material for each element constituting the catalyst to be used for the filling method of the third aspect and the preliminary calcined powder thereof is not limited. For example, as a raw material of a molybdenum component, molybdenum oxides such as molybdenum trioxide, molybdic acid or salts thereof such as molybdate, ammonium paramolybdate and ammonium metamolybdate, and heteropolyacids containing molybdenum or salts thereof such as phosphomolybdic acid and silicate molybdic acid, can be used.

As a raw material of a bismuth component, bismuth salts such as bismuth nitrate, bismuth carbonate, bismuth sulfate, and bismuth acetate, bismuth trioxide, metal bismuth and the like can be used. These raw materials can be used as solids or as an aqueous solution, a nitric acid solution, or a slurry of bismuth compounds generated from those aqueous solutions, and the nitrate, a solution thereof, or a slurry obtained from the solution is preferably used.

As a starting raw material for other constituent elements, ammonium salt, nitrate, nitrite, carbonate, subcarbonate, acetate, chloride, inorganic acid, inorganic acid salt, heteropolyacid, heteropolyacid salt, sulfate, hydroxide, organic acid salt, and oxide of metallic elements commonly used in this type of catalyst may be used, or a mixture thereof may be used in combination. Ammonium salts and nitrates are preferably used.

A compound containing these active components may be used alone or in combination of two or more. A slurry liquid can be obtained by uniformly mixing each compound containing an active component and water. The amount of water to be used in the slurry liquid is not limited as long as the total amount of the compound to be used can be completely dissolved or uniformly mixed. The amount of water to be used may be appropriately determined in consideration of the drying method and the drying conditions. Usually, the amount of water to be used is 100 parts by mass or more and 2000 parts by mass or less with respect to 100 parts by mass of the total mass of the compound for preparing a slurry. The amount of water may be large, but too large amount of water causes many disadvantages such as an increase in the energy cost of the drying step and a possible failure to completely dry.

The slurry liquid of the source compound of the above each component element is preferably prepared by (a) a method of mixing each of the above source compounds at once, (b) a method of mixing the above source compounds at once and then performing aging, (c) a method of mixing the above source compounds stepwise, (d) a method of repeating mixing step and aging step stepwise, and (e) a method combining (a) to (d). Here, the above aging means "an operation in which industrial raw materials or semi-finished products are processed under specific conditions such as a certain period of time and a certain temperature to conduct acquisition or improvement of the required physical properties and chemical properties, or proceeding of a predetermined reaction". In the third aspect, the above certain period of time means a range of 5 minutes or longer and 24 hours or shorter, and the above certain temperature means a range from room temperature to a point equal to or lower than a boiling point of an aqueous solution or an aqueous dispersion liquid. Among these, in terms of the activity and yield of the finally obtained catalyst, preferred is the (c) method of mixing the above source compounds stepwise, more preferred is a method in which each raw material to be mixed with a mother liquid stepwise is completely dissolved to be a solution, and most preferred is a method of mixing various mixed solutions of alkali metal solution and nitrate with a mother liquid in which the raw material of the molybdenum is a mixed solution or slurry. However, it is not always necessary to mix all the elements constituting the catalyst in this step, and some elements or some amounts thereof may be added in the subsequent steps.

In the catalyst used in the third aspect, the shape of the stirring blade of the stirrer used in mixing the essential active components is not limited. Any stirring blade such as a propeller blade, a turbine blade, a paddle blade, an inclined paddle blade, a screw blade, an anchor blade, a ribbon blade, a large lattice blade can be used in one stage or in two or more stages of which blades are the same or different types in the vertical direction. In addition, a baffle (obstruction plate) may be installed in the reaction tank if necessary.

Then, the slurry liquid thus-obtained is dried. The drying method is not limited so long as the slurry liquid can be completely dried by the method, but examples thereof include drum drying, freeze drying, spray drying and evaporation drying. Among these, spray drying, which allows the slurry liquid to be dried into a powder or granule within a short period of time, is particularly preferred in the third aspect. The temperature of the drying with spray drying varies depending on the concentration of the slurry liquid, the liquid sending speed, or the like. Typically, the temperature at the outlet of a drying machine is 70° C. or higher and 150° C. or lower.

Subjecting the catalyst precursor obtained as described above to preliminary calcination, molding, and then main calcination allows for controlling and holding the obtained shape, and obtaining a catalyst having particularly excellent mechanical strength for industrial use, and the catalyst can exhibit stable catalyst performance.

As for the molding, either a carrying shaping in which the preliminarily calcined powder is carried on a carrier such as silica or a non-carrying shaping in which no carrier is used can be adopted. Specific examples of the molding method include tablet molding, press molding, extrusion molding and granulation molding. As the shape of the molded product, for example, a columnar shape, a ring shape, a spherical shape or the like can be appropriately selected in consideration of operating conditions. Preferred is a carried catalyst in which a catalytically active component is carried on a spherical carrier, particularly an inert carrier such as silica or alumina and in which the average particle size is 3.0 mm or more and 10.0 mm or less, and preferably 3.0 mm or more and 8.0 mm or less. As for the carrying method, a tumbling granulation method, a method using a centrifugal flow coating apparatus, a wash coating method, and the like are widely known. The method is not limited as long as the preliminarily calcined powder can be uniformly carried on the carrier, but the tumbling granulation method is preferred in consideration of the production efficiency of the catalyst and the like. Specifically, the tumbling granulation method is a method in which using a device that has a flat or uneven disk at the bottom of a fixed cylindrical container, a carrier charged into the container is vigorously agitated by means of a repeat of rotation motion and revolution motion of the carrier itself by rotating the disk at a high speed, and then the preliminarily calcined powder is added into the container to carry the powder component on the carrier.

On the occasion of carrying, it is preferred to use a binder. Specific examples of the binder which can be used include water, ethanol, methanol, propanol, a polyhydric alcohol, polyvinyl alcohol as a polymer-based binder and a silica sol aqueous solution as an inorganic binder; ethanol, methanol, propanol, and a polyhydric alcohol are preferred; a diol such as ethylene glycol and a triol such as glycerin is more preferred; and an aqueous solution of glycerin having a concentration of 5 mass % or more is still more preferred. Using an appropriate amount of the glycerin aqueous solution allows for obtaining a high-performance catalyst having good molding properties and high mechanical strength. The amount of these binders to be used is usually 2 to 60 parts by mass with respect to 100 parts by mass of the preliminarily calcined powder, and the amount of the glycerin aqueous solution is preferably 15 to 50 parts by mass. The binder and the preliminarily calcined powder may be alternately supplied to a molding machine or simultaneously supplied to the molding machine on the occasion of the carrying. Further, on the occasion of molding, a small amount of known additives such as graphite and talc may be added. None of a molding aid, a pore-forming agent and a carrier added in the molding is considered as the constituent element of the active component in the third aspect, regardless of whether the molding aid, the pore-forming agent and the carrier have the activity in the sense of converting the raw material into some other product.

The preliminary calcination method, the preliminary calcination conditions, the main calcination method, and the main calcination conditions are not limited, but known treatment methods and conditions can be applied. The preliminary calcination or the main calcination is usually carried out at 200° C. or higher and 600° C. or lower, and preferably 300° C. or higher and 550° C. or lower, for 0.5 hours or longer, and preferably 1 hour or longer and 40 hours or shorter under the conditions that an oxygen-containing gas such as air or an inert gas flow. Here, the inert gas refers to a gas that does not reduce the reaction activity of the catalyst, and specific examples thereof include nitrogen, carbon dioxide, helium and argon. The optimum conditions for the main calcination vary depending on the reaction conditions when an unsaturated aldehyde and/or an unsaturated carboxylic acid are produced using a catalyst, and changing the process parameters of the main calcination step, that is, the oxygen content in the atmosphere, the maximum temperature reached and the calcination time falls within the scope of the third aspect, because the changing is well-known for the skilled person. The main calcination step shall be carried out after the above preliminary calcination step, and the maximum temperature reached (main calcination temperature) in the main calcination step shall be higher than the maximum temperature reached (preliminary calcination temperature) in the above preliminary calcination step. The technique of the calcination includes but not limited to a fluidized bed, rotary kiln, muffle furnace, and tunnel firing furnace, and should be selected within an appropriate range in consideration of the final catalyst performance, mechanical strength, molding properties, production efficiency and the like.

The reaction tube filled by the method for filling a catalyst of the third aspect is preferably used as a reaction tube for producing an unsaturated aldehyde compound, an unsaturated carboxylic acid compound, or a conjugated diene compound, is more preferably used as a reaction tube for producing an unsaturated aldehyde compound, and is particularly preferably used as a catalyst for producing acrolein from propylene. In a process of an exothermic reaction such as production of an unsaturated aldehyde compound, an unsaturated carboxylic acid compound, or a conjugated diene compound, it is known to the skilled person that catalyst types having different activities are filled in multiple layers from the inlet side of the reaction tube toward the outlet side of the reaction tube.

[Catalyst in Second Stage]

When the reaction tube filled by the filling method of the third aspect is used for the first stage, that is, used for producing the unsaturated aldehyde compound, an unsaturated carboxylic acid compound can be obtained by performing a second-stage oxidation reaction separately.

In this case, the catalyst of the third aspect can also be used as a catalyst in a second stage, but a catalyst containing a catalytically active component represented by the following formula (III-2) is preferable.

$$Mo_{12}V_{a6}W_{b6}Cu_{c6}Sb_{d6}X6_{e6}Y6_{f6}Z6_{g6}O_{h6} \qquad \text{(III-2)}$$

(in the formula, Mo, V, W, Cu, Sb and O represent molybdenum, vanadium, tungsten, copper, antimony and oxygen, respectively; X6 represents at least one element selected from the group consisting of an alkali metal and thallium; Y6 represents at least one element selected from the group consisting of magnesium, calcium, strontium, barium and zinc; and Z6 represents at least one element selected from the group consisting of niobium, cerium, tin, chromium, manganese, iron, cobalt, samarium, germanium, titanium and arsenic. a6, b6, c6, d6, e6, f6, g6 and h6 represent the atomic proportion of each element, and with respect to molybdenum atom 12, a6 satisfies $0 < a6 \leq 10$, b6 satisfies $0 \leq b6 \leq 10$, c6 satisfies $0 < c6 \leq 6$, d6 satisfies $0 < d6 \leq 10$, e6 satisfies $0 \leq e6 \leq 0.5$, f6 satisfies $0 \leq f6 \leq 1$, and g6 satisfies $0 \leq g6 < 6$. Further, h6 is the number of oxygen atoms required to satisfy the atomic value of each component).

In the production of a catalyst containing the catalytically active component represented by the above formula (I-2), a method widely known as a method for preparing this kind of a catalyst, for example, an oxide catalyst or a catalyst having a heteropolyacid or a salt structure thereof, can be adopted. The raw materials that can be used in producing the catalyst are not limited, and various materials can be used. For example, molybdenum oxides such as molybdenum trioxide, molybdic acid or salts thereof such as molybdic acid and an ammonium molybdate, molybdenum-containing heteropolyacids or salts thereof such as phosphomolybdic acid and silicomolybdic acid, and the like can be used. The raw material of an antimony component is not limited, but antimony trioxide or antimony acetate is preferred. As raw materials for other elements such as vanadium, tungsten, copper and the like, nitrate, sulfate, carbonate, phosphate, organic acid salt, halide, hydroxide, oxide or the metal of these elements can be used.

A compound containing these active components may be used alone or in combination of two or more.

Next, the slurry liquid obtained above is dried to obtain a solid of catalytically active component. The drying method is not limited so long as the slurry liquid can be completely dried by the method. However, examples thereof include drum drying, freeze drying, spray drying and evaporation drying. Spray drying is preferred because the slurry liquid can be dried into a powder or granule in a short period of time. The temperature of the drying with spray drying varies depending on the concentration of the slurry liquid, the liquid sending speed or the like, but the temperature at the outlet of a drying machine is approximately 70° C. to 150° C. In this case, the slurry liquid is preferably dried such that the average particle size of a slurry liquid dried product (catalyst precursor) to be obtained is 10 μm to 700 μm.

The solid of catalytically active component in the second stage obtained as described above can be used as it is for a coating mixture, and is preferably subjected to calcination because the molding properties may be improved. The calcination method and the calcination conditions are not limited, and known treatment methods and conditions can be applied. The optimum calcination conditions vary depending on the used raw material for the catalyst, catalyst composition, preparation method and the like. The calcination temperature is usually 100° C. to 350° C., preferably 150° C. to 300° C., and the calcination time is usually 1 to 20 hours. The calcination is usually carried out in an air atmosphere, but may be carried out in an atmosphere of an inert gas such as nitrogen, carbon dioxide, helium or argon. The calcination in an air atmosphere may be carried out after calcination in an inert gas atmosphere, if necessary. The thus-obtained calcined solid is preferably pulverized before the molding. The pulverizing method is not limited, but it is preferable to use a ball mill.

The compound containing the active component in preparing the slurry for the second stage does not necessarily have to contain all the active components, and a part of the components may be used before the following molding step.

The shape of the catalyst in the second stage is not limited. The catalyst is used by being molded into a columnar shape, a tablet, a ring shape, a spherical shape or the like in order to reduce the pressure loss of a reaction gas in the oxidation reaction. Among these, the solid of catalytically active component is particularly preferably carried on an inert carrier to be a carried catalyst because improvement in selectivity and removal of heat of reaction can be expected. A tumbling granulation method described below is preferred for the carrying. This method is a method in which, for example, in a device that has a flat or uneven disk at the bottom of a fixed container, a carrier in the container is vigorously agitated by repeatedly performing rotation motion and revolution motion by rotating the disk at a high speed, and then a mixture for the carrying including the binder, the solid of catalytically active component and optionally a molding aid and/or a strength improver is carried on the carrier. As a method of adding the binder, any methods may be adapted such as 1) premixing a binder with the mixture for the carrying, 2) adding the binder at the same time as the mixture for the carrying is added into the fixed container, 3) adding the binder after adding the mixture for the carrying into the fixed container, 4) adding the binder before adding the mixture for the carrying into the fixed container, 5) dividedly preparing the mixture for the carrying and the binder independently and adding the whole amount of them in the appropriate combination of 2) to 4). Among these, for example, 5) is preferably performed by adjusting the adding rate using an auto feeder or the like such that the mixture for the carrying does not adhere to the wall of the fixed container and the mixture for the carrying does not aggregate with each other and a predetermined amount of the mixture for the carrying is carried on the carrier. Examples of the binder include water, ethanol, polyhydric alcohol, polyvinyl alcohol as a polymer-based binder, celluloses such as a crystalline cellulose, methyl cellulose and ethyl cellulose, and an aqueous silica sol solution as an inorganic binder. Diols such as cellulose and ethylene glycol and triols such as glycerin are preferred, and an aqueous solution having a concentration of glycerin of 5 mass % or more is particularly preferred. The amount of these binders to be used is usually 2 to 60 parts by mass, preferably 10 to 50 parts by mass, per 100 parts by mass of the mixture for the carrying.

Specific examples of the carrier in the above carrying include a spherical carrier having a diameter of 1 mm to 15 mm, and preferably 2.5 mm to 10 mm, such as silicon carbide, alumina, silica alumina, mullite and arandom. The carriers having a porosity of 10% to 70% are usually used. The carrier and the mixture for the carrying at the ratio of the mixture for the carrying/(mixture for the carrying+carrier) =10 mass % to 75 mass % are usually used, and the carrier and the mixture for the carrying at the ratio of the mixture for the carrying/(mixture for the carrying+carrier)=15 mass % to 60 mass % are preferably used. When the ratio of the mixture for the carrying tends to be large, the reaction activity of the carried catalyst is large, but the mechanical strength tends to be small. On the contrary, when the ratio of the mixture for the carrying is small, the mechanical strength tends to be large, but the reaction activity tends to be small. In the above, examples of the molding aid to be used as necessary include silica gel, diatomite, and alumina powder. The amount of the molding aid to be used is usually 1 to 60 parts by mass with respect to 100 parts by mass of the solid of catalytically active component. If necessary, the use of inorganic fibers (for example, ceramic fibers or whiskers) that are inactive to the solid of catalytically active component and the reaction gas as the strength improver is useful for improving the mechanical strength of the catalyst, and glass fibers are preferred. The amount of the fiber to be used is usually 1 to 30 parts by mass with respect to 100 parts by mass of the solid of catalytically active component. None of a molding aid, a pore-forming agent and a carrier added in the molding of the catalyst for the first stage is considered as the constituent element of the active component in the third aspect, regardless of whether the molding aid, the pore-forming agent and the carrier have the activity in the sense of converting the raw material into some other product.

The carried catalyst obtained as described above can be used as a catalyst for the catalytic gas phase oxidation, and is preferably subjected to calcination because the molding properties may be improved. The calcination method and the calcination conditions are not limited, and known treatment methods and conditions can be applied. The optimum calcination conditions vary depending on the raw material for the catalyst to be used, the catalyst composition, the preparation method, and the like, but the calcination temperature is usually 100° C. to 450° C., preferably 270° C. to 420° C., and the calcination time is usually 1 to 20 hours. The calcination is usually carried out in an air atmosphere, and may be carried out in an atmosphere of an inert gas such as nitrogen, carbon dioxide, helium or argon. The calcination in an air atmosphere may be carried out after the calcination in an inert gas atmosphere, if necessary.

When the catalyst of the third aspect is used in a reaction of using propylene, isobutylene, t-butyl alcohol and the like as raw materials to produce the corresponding unsaturated aldehyde, unsaturated carboxylic acid, and particularly, in a reaction of producing acrolein and acrylic acid by catalytic gas phase oxidation of propylene with molecular oxygen or a gas containing molecular oxygen, using the catalyst of the third aspect allows for improving the catalytic activity and the yield, and is very effective in improving the price competitiveness of the product as compared with the known method. In addition, the effect of improving the process stability of the partial oxidation reaction accompanied by heat generation, such as reduction of the hot spot temperature can be expected. Further, the catalyst of the third aspect is also effective in reducing by-products that adversely influences the environment and the quality of the final product, such as carbon monoxide (CO), carbon dioxide ($CO_2$), acetaldehyde, acetic acid, and formaldehyde.

The thus-obtained catalyst of the third aspect can be used, for example, for producing acrolein and/or acrylic acid by catalytic gas phase oxidation of propylene using a molecular oxygen-containing gas. In the production method of the third aspect, the method for flowing the raw material gas may be an ordinary single-flow method or a recycling method, and can be carried out under widely used conditions, and is not limited. For example, a mixed gas containing 1 vol % to 10 vol % and preferably 4 vol % to 9 vol % of propylene, 3 vol % to 20 vol % and preferably 4 vol % to 18 vol % of molecular oxygen, 0 vol % to 60 vol % and preferably 4 vol % to 50 vol % of water vapor at room temperature as a starting raw material, and 20 vol % to 80 vol % and preferably 30 vol % to 60 vol % of an inert gas such as carbon dioxide and nitrogen is introduced to the catalyst of the third aspect filled in a reaction tube at 250° C. to 450° C. under normal pressure to 10 atm and a space velocity of 300 to 5000 h$^{-1}$ to perform a reaction.

In the third aspect, unless otherwise specified, the improvement of the catalytic activity means that the conversion rate of the raw material is high when the catalytic reaction is carried out at the same salt bath temperature.

In the third aspect, unless otherwise specified, a high yield means that the total yield of the corresponding unsaturated aldehyde and/or unsaturated carboxylic acid is high when the oxidation reaction is performed using propylene, isobutylene, t-butyl alcohol, and the like as raw materials. Unless otherwise specified, the yield refers to a useful yield described later.

In the third aspect, unless otherwise specified, the constituent elements of the catalytically active component refer to all the elements to be used in the method for producing a catalyst, but the raw materials and the constituent elements thereof that disappear, sublimate, volatilize, and burn at the maximum temperature or lower in the main calcination step are not included in the constituent elements of the catalytically active component. Further, silicon and the other elements constituting inorganic materials contained in the molding aid and the carrier in the shaping step are not included in the constituent elements of the catalytically active component.

In the third aspect, the hot spot temperature refers to the maximum temperature in the temperature distribution in the catalyst-filled bed that is measured in thermocouples installed in the multi-tube reaction tube in the long axis direction, and the salt bath temperature refers to a set temperature of a heat medium used for the purpose of cooling the heat generated in the reaction tube. The number of measuring points in the temperature distribution is not limited, but for example, the catalyst filling length is evenly divided from 10 to 1000.

In the third aspect, the unsaturated aldehyde and the unsaturated aldehyde compound refers to organic compounds having at least one double bond and at least one aldehyde in the molecule, such as acrolein and methacrolein. In the third aspect, the unsaturated carboxylic acid and the unsaturated carboxylic acid compound refers to organic compounds having at least one double bond and at least one carboxy group or an ester group of the carboxyl group in the molecule, and are, for example, acrylic acid, methacrylic acid, and methyl methacrylate. In the third aspect, the conjugated diene refers to a diene in which a double bond is separated by one single bond and which is chemically conjugated, and is, for example, 1,3-butadiene.

In the third aspect, Bi means bismuth among the constituent elements of the catalytically active component, unless otherwise specified. Similarly, Mo indicates molybdenum, Fe indicates iron, Co indicates cobalt, Ni indicates nickel, K indicates potassium, and Cs indicates cesium.

EXAMPLE

Example of First Aspect

Hereinafter, the first aspect of the present invention will be described in more detail with reference to Examples. In Examples, a conversion rate of a raw material, a useful yield, a butadiene yield, a useful selectivity, and an active mass ratio were calculated according to the following formulae.

Conversion rate (%) of raw material=(number of
moles of reacted propylene,t-butyl alcohol,
isobutylene or butene)/(number of moles of
supplied propylene,t-butyl alcohol,isobutylene
or butene)×100

Useful yield (%)=(total number of moles of pro-
duced acrolein and acrylic acid, or total number
of moles of produced methacrolein and meth-
acrylic acid)/(number of moles of supplied pro-
pylene,t-butyl alcohol or isobutylene)×100

Butadiene yield (%)=(total number of moles of pro-
duced butadiene)/(number of moles of supplied
butene)×100

Useful selectivity (%)=(total number of moles of
produced acrolein and acrylic acid,total number
of moles of produced methacrolein and meth-
acrylic acid, or total number of moles of pro-
duced butadiene)/(number of moles of reacted
propylene,t-butyl alcohol,isobutylene or
n-butene)×100

Active mass ratio (mass %)=(mass of preliminary
calcined powder used for molding)/{(mass of
preliminary calcined powder used for mold-
ing)+(mass of carrier used for molding)}×100

An X-ray diffraction (XRD) angle (2θ) was measured by using Ultima IV manufactured by Rigaku Corporation under conditions of an X-ray CuKα ray (λ=0.154 nm), an output of 40 kV, 30 mA, a measurement range of 10° to 60°, and a measurement rate of 10° per minute. Further, a calcination time described in each of the following examples means a holding time from a time when each calcination temperature reaches, in which a time of temperature increase and temperature decrease is not included.

Example I-1

100 parts by mass of ammonium heptamolybdate having a purity of 81% as MoO₃ was completely dissolved in 380 parts by mass of pure water heated to 60° C. (mother liquid 1). Next, 0.17 parts by mass of potassium nitrate having a purity of 99.0% was dissolved in 1.9 parts by mass of pure water, and the mixture was added to the mother liquid 1. Next, 37 parts by mass of ferric nitrate having a purity of 99.5%, 90 parts by mass of cobalt nitrate having a purity of 99.0%, and 33 parts by mass of nickel nitrate having a purity of 99.9% were dissolved in 85 parts by mass of pure water heated to 60° C., and the mixture was added dropwise to the mother liquid 1. Subsequently, 16 parts by mass of bismuth nitrate having a purity of 99.5% was dissolved in an aqueous nitric acid solution prepared by adding 4.1 parts by mass of nitric acid (60 mass %) to 17 parts by mass of pure water heated to 60° C., and the mixture was added dropwise to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:0.7:2.0:6.5:2.4:0.04) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 530° C. and 4 hours to obtain a catalyst I-1. The X-ray diffraction angle (2θ) of the catalyst I-1 was measured.

Example I-2

100 parts by mass of ammonium heptamolybdate was completely dissolved in 380 parts by mass of pure water heated to 60° C. (mother liquid 1). Next, 0.37 parts by mass of potassium nitrate was dissolved in 3.5 parts by mass of pure water, and the mixture was added to the mother liquid 1. Next, 28 parts by mass of ferric nitrate, 81 parts by mass of cobalt nitrate, and 47 parts by mass of nickel nitrate were dissolved in 82 parts by mass of pure water heated to 60° C., and the mixture was added to the mother liquid 1. Subsequently, 23 parts by mass of bismuth nitrate was dissolved in an aqueous nitric acid solution prepared by adding 5.8 parts by mass of nitric acid (60 mass %) to 24 parts by mass of pure water heated to 60° C., and the mixture was added to the mother liquid 1. The mother liquid 1 was dried by spray drying, and the obtained dried powder was prelimi-nary calcined at 440° C. for 4 hours. Five mass % of a crystalline cellulose with respect to the preliminarily cal-cined powder (the atomic proportion calculated from the charged raw materials was Mo:Bi:Fe:Co:Ni:K=12:1.0:1.5: 5.9:3.4:0.08) was added to the preliminarily calcined pow-der, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 510° C. and 4 hours to obtain a catalyst I-2. The X-ray diffraction angle (2θ) of the catalyst I-2 was measured.

Example I-3

100 parts by mass of ammonium heptamolybdate was completely dissolved in 380 parts by mass of pure water heated to 60° C. (mother liquid 1). Next, 0.37 parts by mass of potassium nitrate was dissolved in 3.5 parts by mass of pure water, and the mixture was added to the mother liquid 1. Next, 31 parts by mass of ferric nitrate, 81 parts by mass of cobalt nitrate, and 44 parts by mass of nickel nitrate were dissolved in 82 parts by mass of pure water heated to 60° C., and the mixture was added to the mother liquid 1. Subse-quently, 23 parts by mass of bismuth nitrate was dissolved in an aqueous nitric acid solution prepared by adding 5.8 parts by mass of nitric acid (60 mass %) to 24 parts by mass of pure water heated to 60° C., and the mixture was added to the mother liquid 1. The mother liquid 1 was dried by spray drying, and the obtained dried powder was prelimi-nary calcined at 440° C. for 4 hours. Five mass % of a crystalline cellulose with respect to the preliminarily cal-cined powder (the atomic proportion calculated from the charged raw materials was Mo:Bi:Fe:Co:Ni:K=12:1.0:1.6: 5.9:3.2:0.08) was added to the preliminarily calcined pow-der, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 510° C. and 4 hours to obtain a catalyst I-3. The X-ray diffraction angle (2θ) of the catalyst I-3 was measured. FIG. 1 is a diagram illustrating an X-ray diffraction pattern of the catalyst I-3.

Example I-4

100 parts by mass of ammonium heptamolybdate was completely dissolved in 380 parts by mass of pure water heated to 60° C. (mother liquid 1). Next, 0.37 parts by mass of potassium nitrate was dissolved in 3.5 parts by mass of pure water, and the mixture was added to the mother liquid 1. Next, 33 parts by mass of ferric nitrate, 70 parts by mass of cobalt nitrate, and 49 parts by mass of nickel nitrate were dissolved in 81 parts by mass of pure water heated to 60° C., and the mixture was added to the mother liquid 1. Subsequently, 23 parts by mass of bismuth nitrate was dissolved in an aqueous nitric acid solution prepared by adding 5.8 parts by mass of nitric acid (60 mass %) to 24 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:1.0:1.8: 5.1:3.6:0.08) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 520° C. and 4 hours to obtain a catalyst I-4. The X-ray diffraction angle (2θ) of the catalyst I-4 was measured.

Example I-5

100 parts by mass of ammonium heptamolybdate was completely dissolved in 380 parts by mass of pure water heated to 60° C. (mother liquid 1). Next, 0.56 parts by mass of potassium nitrate was dissolved in 5.3 parts by mass of pure water, and the mixture was added to the mother liquid 1. Next, 33 parts by mass of ferric nitrate, 81 parts by mass of cobalt nitrate, and 44 parts by mass of nickel nitrate were dissolved in 84 parts by mass of pure water heated to 60° C., and the mixture was added to the mother liquid 1. Subsequently, 23 parts by mass of bismuth nitrate was dissolved in an aqueous nitric acid solution prepared by adding 5.8 parts by mass of nitric acid (60 mass %) to 24 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:1.0:1.8: 5.9:3.2:0.12) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 520° C. and 4 hours to obtain a catalyst I-5. The X-ray diffraction angle (2θ) of the catalyst I-5 was measured.

Comparative Example I-1

100 parts by mass of ammonium heptamolybdate was completely dissolved in 380 parts by mass of pure water heated to 60° C. (mother liquid 1). Next, 0.33 parts by mass of potassium nitrate was dissolved in 3.4 parts by mass of pure water, and the mixture was added to the mother liquid 1. Next, 31 parts by mass of ferric nitrate, 103 parts by mass of cobalt nitrate, and 23 parts by mass of nickel nitrate were dissolved in 85 parts by mass of pure water heated to 60° C., and the mixture was added to the mother liquid 1. Subsequently, 18 parts by mass of bismuth nitrate was dissolved in an aqueous nitric acid solution prepared by adding 5.0 parts by mass of nitric acid (60 mass %) to 19 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:0.8:1.6: 7.5:1.7:0.07) was added to the preliminarily calcined powder, followed by thoroughly being mixed. The mixture was carried and molded into a spherical shape on an inert carrier by using a 33 mass % glycerin solution as a binder by tumbling granulation method so that an active mass ratio was 50 mass %. The thus-obtained spherical molded product having a particle size of 5.3 mm was subjected to main calcination under the conditions of 480° C. and 4 hours to obtain a catalyst I-6. The X-ray diffraction angle (2θ) of the catalyst I-6 was measured.

Comparative Example I-2

100 parts by mass of ammonium heptamolybdate was completely dissolved in 380 parts by mass of pure water heated to 60° C. (mother liquid 1). Next, 0.19 parts by mass of potassium nitrate was dissolved in 1.9 parts by mass of pure water, and the mixture was added to the mother liquid 1. Next, 31 parts by mass of ferric nitrate, 82 parts by mass of cobalt nitrate, and 32 parts by mass of nickel nitrate were dissolved in 77 parts by mass of pure water heated to 60° C., and the mixture was added to the mother liquid 1. Subsequently, 14 parts by mass of bismuth nitrate was dissolved in an aqueous nitric acid solution prepared by adding 3.5 parts by mass of nitric acid (60 mass %) to 15 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:0.6:1.6: 6.0:2.3:0.04) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 530° C. and 4 hours to obtain a catalyst I-7. The X-ray diffraction angle (2θ) of the catalyst I-7 was measured.

Comparative Example I-3

100 parts by mass of ammonium heptamolybdate was completely dissolved in 380 parts by mass of pure water heated to 60° C. (mother liquid 1). Next, 0.17 parts by mass of potassium nitrate was dissolved in 1.9 parts by mass of pure water, and the mixture was added to the mother liquid 1. Next, 37 parts by mass of ferric nitrate, 90 parts by mass of cobalt nitrate, and 33 parts by mass of nickel nitrate were dissolved in 85 parts by mass of pure water heated to 60° C., and the mixture was added to the mother liquid 1. Subsequently, 16 parts by mass of bismuth nitrate was dissolved in an aqueous nitric acid solution prepared by adding 4.1 parts by mass of nitric acid (60 mass %) to 17 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:0.7:2.0:6.5:2.4:0.04) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 550° C. and 4 hours to obtain a catalyst I-8. The X-ray diffraction angle (2θ) of the catalyst I-8 was measured.

Production Example I-1

100 parts by mass of ammonium heptamolybdate was completely dissolved in 380 parts by mass of pure water being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 530° C. and 4 hours to obtain a catalyst I-9. As a result of measurement of the X-ray diffraction angle (2θ) of the catalyst I-9, it was found that S=39.1, S1=21.9, S2=17.3, S3=0, and S4=11.4.

Using the catalysts I-1 to I-8, an oxidation reaction of propylene was carried out by the following method to determine a conversion rate of a raw material and a useful yield. The catalyst I-9 was charged into a gas inlet side of a stainless steel reaction tube having an inner diameter of 28.4 mm, and the catalysts I-1 to I-8 were charged into a gas outlet side of the stainless steel reaction tube, respectively, and a mixed gas having a gas volume ratio of propylene:oxygen:water vapor:nitrogen=1.0:2.6:8.3:7.4 was introduced at a propylene space velocity of 100 hr⁻¹ with respect to all the catalysts in the reaction tube to carry out the oxidation reaction of propylene. After the aging reaction at a salt bath temperature of 315° C. for 20 hours or more from the start of the reaction, the conversion rate of the raw material and the useful yield shown in Table 1 were determined by analyzing the gas at the outlet of the reaction tube at a reaction blade temperature of 320° C. In addition, S, S1, S2, S3, and S4 described above are also shown in Table 1.

TABLE 1

| | Catalyst at reaction tube outlet | S | S1 | S2 | S3 | S4 | Conversion rate (%) | Useful yield (%) | Useful selectivity (%) |
|---|---|---|---|---|---|---|---|---|---|
| Example I-1 | Catalyst I-1 | 65.6 | 19.6 | 13.8 | 32.1 | 14.2 | 97.0 | 91.3 | 94.2 |
| Example I-2 | Catalyst I-2 | 55.2 | 14.8 | 12.2 | 28.2 | 9.4 | 97.0 | 91.7 | 94.5 |
| Example I-3 | Catalyst I-3 | 69.4 | 22.1 | 17.1 | 30.2 | 12.3 | 96.6 | 91.7 | 94.9 |
| Example I-4 | Catalyst I-4 | 73.6 | 26.9 | 18.9 | 27.8 | 11.1 | 96.8 | 91.6 | 94.7 |
| Example I-5 | Catalyst I-5 | 91.2 | 28.8 | 22.9 | 39.5 | 10.6 | 96.6 | 91.5 | 94.7 |
| Comparative Example I-1 | Catalyst I-6 | 41.5 | 17.6 | 14.4 | 9.5 | 23.4 | 97.7 | 90.1 | 92.3 |
| Comparative Example I-2 | Catalyst I-7 | 160.1 | 65.9 | 21.1 | 73.1 | 15.9 | 79.4 | 76.0 | 95.8 |
| Comparative Example I-3 | Catalyst I-8 | 113.6 | 42.9 | 23.8 | 46.9 | 12.7 | 96.7 | 91.1 | 94.2 | heated to 60° C. (mother liquid 1). Next, 0.45 parts by mass of potassium nitrate was dissolved in 45 parts by mass of pure water and added to the mother liquid 1. Next, 33 parts by mass of ferric nitrate, 72 parts by mass of cobalt nitrate, and 38 parts by mass of nickel nitrate were dissolved in 76 parts by mass of pure water heated to 60° C., and the mixture was added to the mother liquid 1. Subsequently, 38 parts by mass of bismuth nitrate was dissolved in an aqueous nitric acid solution prepared by adding 9.7 parts by mass of nitric acid (60 mass %) to 41 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:1.7:1.8:5.2:2.8:0.10) was added to the preliminarily calcined powder, followed by thoroughly From Table 1, it can be seen that the catalysts I-1 to I-5 in which S is within the range of the first aspect exhibit a very high useful yield. Further, the relationship of the useful yield with respect to S is represented as an upwardly convex curve, and it has been clarified by the inventors that S has a preferable range from the viewpoint of the useful yield.

Example I-6

100 parts by mass of ammonium heptamolybdate was completely dissolved in 380 parts by mass of pure water heated to 80° C. (mother liquid 1). Next, 1.38 parts by mass of cesium nitrate was dissolved in 15.0 parts by mass of pure water, and the mixture was added to the mother liquid 1. Next, 37 parts by mass of ferric nitrate, 99 parts by mass of cobalt nitrate, and 11 parts by mass of nickel nitrate were dissolved in 78 parts by mass of pure water heated to 60° C., and the mixture was added to the mother liquid 1. Subsequently, 34 parts by mass of bismuth nitrate was dissolved in an aqueous nitric acid solution prepared by adding 8.7 parts by mass of nitric acid (60 mass %) to 36 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:1.5:2.0: 7.2:0.8:0.15) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 4.4 mm was subjected to main calcination under the conditions of 520° C. and 4 hours to obtain a catalyst I-10. The X-ray diffraction angle (2θ) of the catalyst I-10 was measured.

Examples I-6A and I-6B and Comparative Example I-5

The reaction of catalyst I-10 was evaluated by the following method. A stainless-steel reaction tube was filled with 34 ml of each catalyst, and an aging reaction of TOS for 20 hours or more was performed at a salt bath temperature of 350° C. under the conditions of an outlet pressure of 50 kPaG and a GHSV of 1200 hr$^{-1}$ using a mixed gas having a gas volume ratio of isobutylene:oxygen:nitrogen:water vapor=1:2.2:12.5:1.0. Then, the salt bath temperature was set to 330° C., a condensed liquid component and a gas component were separated by a condenser at the outlet of the reaction tube, and each component in the gas and the condensed liquid was respectively quantitatively analyzed by a gas chromatograph equipped with a flame ionization detector and a thermal conductivity detector. Each data obtained by the gas chromatograph was subjected to factor correction, and the conversion rate of the raw material and the useful yield shown in Table 2 were determined. In addition, S, S1, S2, S3, and S4 described above are also shown in Table 2.

TABLE 2

| | Catalyst | S | S1 | S2 | S3 | S4 | Conversion rate (%) | Useful yield (%) | Useful selectivity (%) |
|---|---|---|---|---|---|---|---|---|---|
| Example I-6A | Catalyst I-10 | 94.1 | 29.0 | 21.7 | 43.4 | 27.5 | 98.7 | 81.6 | 82.7 |

Comparative Example I-5

16.5 parts by mass of nitric acid (60 mass %) was added to 300 parts by mass of pure water heated to 60° C., 0.42 parts by mass of cesium nitrate, 10 parts by mass of bismuth nitrate, 11 parts by mass of ferric nitrate, 28 parts by mass of cobalt nitrate, and 3 parts by mass of nickel nitrate were added thereto, and the mixture was stirred and completely dissolved, and naturally cooled (mother liquid 1). Next, the mother liquid 1 was carried on 30 parts by mass of CARI-ACT Q-50C (particle size: 4.4 mm) manufactured by FUJI SILYSIA CHEMICAL LTD., by an incidence wetness method, and the carried one was preliminary calcined at 440° C. for 4 hours. A mother liquid obtained by completely dissolving 100 parts by mass of ammonium heptamolybdate The reaction of the catalyst I-10 and the catalyst I-11 were evaluated by the following method. A stainless steel reaction tube was filled with 53 ml of each catalyst, and an aging reaction of TOS for 20 hours or more was performed by changing a salt bath temperature so that the conversion rate=98.0±1.0% can be maintained under the conditions of normal pressure and GHSV of 1200 hr$^{-1}$ by using a mixed gas having a gas volume ratio of 1-butene:oxygen:nitrogen: water vapor=1:1:7:1. Then, the salt bath temperature was set to 370° C., a liquid component and a gas component were separated by a condenser at the outlet of the reaction tube, and each component in the gas component was respectively quantitatively analyzed by a gas chromatograph equipped with a flame ionization detector and a thermal conduction detector. Each data obtained by gas chromatography was subjected to factor correction, and the conversion rate of the raw material and the butadiene yield shown in Table 3 were determined. In addition, S, S1, S2, S3, and S4 described above are shown in Table 3.

TABLE 3

| | Catalyst | S | S1 | S2 | S3 | S4 | Conversion rate (%) | Useful yield (%) | Useful selectivity (%) |
|---|---|---|---|---|---|---|---|---|---|
| Example I-6B | Catalyst I-10 | 94.1 | 29.0 | 21.7 | 43.4 | 27.5 | 97.2 | 85.9 | 88.4 |
| Comparative Example I-3 | Catalyst I-11 | 17.2 | 0.0 | 17.2 | 0.0 | 95.4 | 92.0 | 77.1 | 83.8 | in 380 parts by mass of pure water heated to 80° C. was further carried on the thus-obtained catalyst precursor by the incidence wetness method, and the carried one was preliminary calcined at 440° C. for 4 hours, and then subjected to main calcination under the conditions of 520° C. for 4 hours to obtain a catalyst I-11. The X-ray diffraction angle (2θ) of the catalyst I-11 was measured. The atomic proportion of the catalyst I-11 calculated from the charged raw materials was Mo:Bi:Fe:Co:Ni:K=12:1.5:2.0:7.2:0.8:0.15.

From Tables 2 and 3, it was clarified by the inventors that S has a preferable range from the viewpoint of yield in the partial oxidation reaction of isobutylene and the oxidative dehydrogenation reaction of butene in addition to the partial oxidation reaction of propylene.

Example I-7

100 parts by mass of ammonium heptamolybdate was completely dissolved in 380 parts by mass of pure water heated to 80° C. (mother liquid 1). Next, 0.48 parts by mass of potassium nitrate was dissolved in 48.0 parts by mass of pure water, and the mixture was added to the mother liquid 1. Next, 38 parts by mass of ferric nitrate, 88 parts by mass of cobalt nitrate, and 34 parts by mass of nickel nitrate were dissolved in 85 parts by mass of pure water heated to 60° C., and the mixture was added to the mother liquid 1. Subsequently, 18 parts by mass of bismuth nitrate was dissolved in an aqueous nitric acid solution prepared by adding 4.7 parts by mass of nitric acid (60 mass %) to 19 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:0.8:2.0: 6.4:2.5:0.10) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50

% glycerin solution as a binder by tumbling granulation so that an active mass ratio was 50 mass %. The thus-obtained spherical molded product having a particle size of 5.3 mm was subjected to main calcination under the conditions of 535° C. and 4 hours to obtain a catalyst I-13. The X-ray diffraction angle (2θ) of the catalyst I-13 was measured.

Using the catalyst I-12 and the catalyst I-13, an oxidation reaction of propylene was carried out by the following method, and the conversion rate of the raw material and the useful yield were determined. A stainless-steel reaction tube having an inner diameter of 28.4 mm was filled with each catalyst, and a mixed gas having a gas volume ratio of propylene:oxygen:water vapor:nitrogen=1.0:1.7:1.3:9.0 was introduced at a propylene space velocity of 160 hr$^{-1}$ with respect to all the catalysts in the reaction tube to carry out an oxidation reaction of propylene. After the aging reaction at a salt bath temperature of 320° C. for 20 hours or more from the start of the reaction, the conversion rate of the raw material and the useful yield shown in Table 4 were determined by analyzing the gas at the outlet of the reaction tube at a reaction blade temperature of 325° C. In addition, S, S1, S2, S3, and S4 described above are also shown in Table 4.

TABLE 4

|  | Catalyst | S | S1 | S2 | S3 | S4 | Conversion rate (%) | Useful yield (%) | Useful selectivity (%) |
|---|---|---|---|---|---|---|---|---|---|
| Example I-7 | Catalyst I-12 | 90.3 | 34.0 | 22.6 | 33.7 | 18.3 | 82.3 | 78.9 | 95.8 |
| Comparative Example I-6 | Catalyst I-13 | 144.0 | 55.6 | 31.6 | 56.8 | 21.4 | 69.2 | 67.0 | 96.9 | mass %. The thus-obtained spherical molded product having a particle size of 5.3 mm was subjected to main calcination under the conditions of 535° C. and 4 hours to obtain a catalyst I-12. The X-ray diffraction angle (2θ) of the catalyst I-12 was measured.

Comparative Example I-6

100 parts by mass of ammonium heptamolybdate was completely dissolved in 380 parts by mass of pure water heated to 80° C. (mother liquid 1). Next, 0.48 parts by mass of potassium nitrate was dissolved in 48.0 parts by mass of pure water, and the mixture was added to the mother liquid 1. Next, 88 parts by mass of cobalt nitrate and 34 parts by mass of nickel nitrate were dissolved in 65 parts by mass of pure water heated to 60° C. to prepare a mother liquid 2. Subsequently, 18 parts by mass of bismuth nitrate and 38 parts by mass of ferric nitrate were dissolved in an aqueous nitric acid solution prepared by adding 4.7 parts by mass of nitric acid (60 mass %) to 39 parts by mass of pure water heated to 60° C. to prepare a mother liquid 3. After 37 parts by mass of the mother liquid 2 was added to the mother liquid 1 and 30 minutes passed (step 6a), 20 parts by mass of the mother liquid 3 was added thereto and 30 minutes passed (step 6b). The operations of step 6a and step 6b were repeated four times in total to proceed with the preparation. The thus-obtained mixed solution was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:0.8:2.0:6.4:2.5:0.10) was added to the preliminarily calcined powder, followed by thoroughly being mixed. The mixture was carried and molded into a spherical shape on an inert carrier by using a 33 mass From Table 4, it was revealed by the inventors that the optimum range of S was valid in the partial oxidation reaction of propylene, even under reaction conditions and using methods different from those in Table 1.

Example of Second Aspect

Hereinafter, the second aspect of the present invention will be described in more detail with reference to Examples. In Examples, a conversion rate of a raw material, a useful selectivity, a butadiene selectivity, an active mass ratio, and an oxygen concentration at an outlet were calculated according to the following formulae.

Conversion rate (%) of raw material=(number of moles of reacted propylene,t-butyl alcohol, isobutylene or butene)/(number of moles of supplied propylene,t-butyl alcohol,isobutylene or butene)×100

Useful selectivity (%)=(total number of moles of produced acrolein and acrylic acid, or total number of moles of produced methacrolein and methacrylic acid)/(number of moles of reacted propylene,t-butyl alcohol or isobutylene)×100

Butadiene selectivity (%)=(total number of moles of produced butadiene)/(number of moles of reacted butene)×100

Active mass ratio (mass %)=(mass of preliminary calcined powder used for molding)/{(mass of preliminary calcined powder used for molding)+(mass of carrier used for molding)}×100

Oxygen concentration at outlet (vol %)=(number of moles of oxygen at outlet of reaction tube)/ (number of moles of total gas at outlet of reaction tube containing water vapor)×100

An X-ray diffraction (XRD) angle (2θ) was measured by using Ultima IV manufactured by Rigaku Corporation under conditions of an X-ray CuKα ray (λ=0.154 nm), an output of 40 kV, 30 mA, a measurement range of 10° to 60°, and a measurement rate of 10° per minute. Further, a calcination time described in each of the following examples means a holding time from a time when each calcination temperature reaches, in which a time of temperature increase and temperature decrease is not included.

In addition, an aging treatment described later means that a reaction tube having a specified thickness is filled with a catalyst, propylene is caused to flow at a specified flow rate, and an oxidation reaction is performed for a specified period. The salt bath temperature at this time is any temperature, but the lower limit thereof is 300° C.

Production Example II-1

Figure 2:
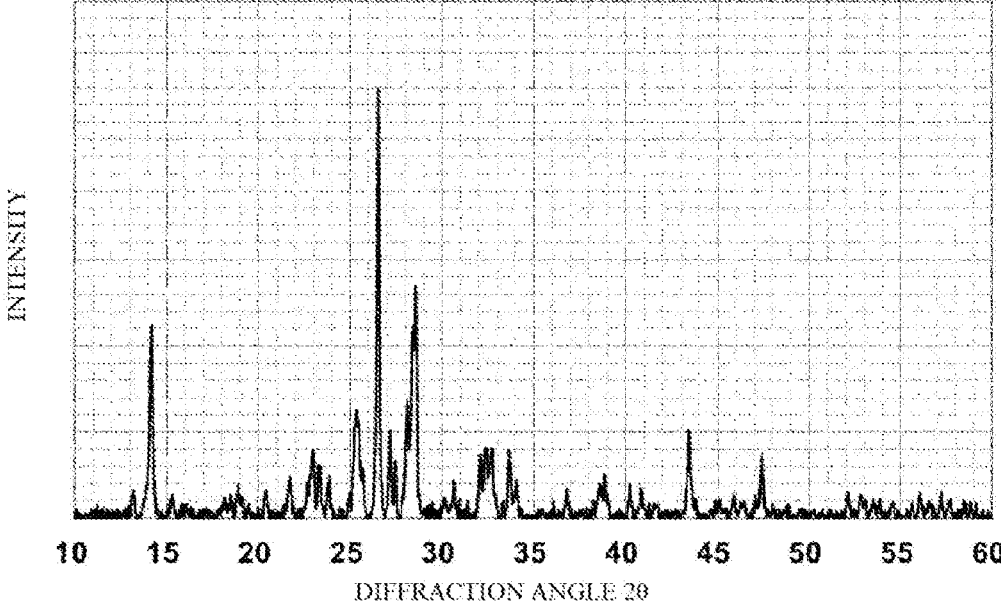
FIG. 2 is a graph representing an X-ray diffraction pattern of a catalyst (catalyst II-1-1) in Production Example II-1.

100 parts by mass of ammonium heptamolybdate was completely dissolved in 380 parts by mass of pure water heated to 60° C. (mother liquid 1). Next, 0.46 parts by mass of potassium nitrate was dissolved in 4.1 parts by mass of pure water, and the mixture was added to the mother liquid 1. Next, 38 parts by mass of ferric nitrate, 89 parts by mass of cobalt nitrate, and 33 parts by mass of nickel nitrate were dissolved in 85 parts by mass of pure water heated to 60° C., and the mixture was added to the mother liquid 1. Subsequently, 16 parts by mass of bismuth nitrate was dissolved in an aqueous nitric acid solution prepared by adding 4.1 parts by mass of nitric acid (60 mass %) to 17 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:0.7:2.0:6.5:2.4:0.10) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 540° C. and 4 hours to obtain a catalyst II-1-1. The X-ray diffraction angle (2θ) of the catalyst II-1-1 was measured. FIG. 2 is a diagram illustrating an X-ray diffraction pattern of the catalyst II-1-1. S3 was 13.5.

Example II-1

Figure 3:
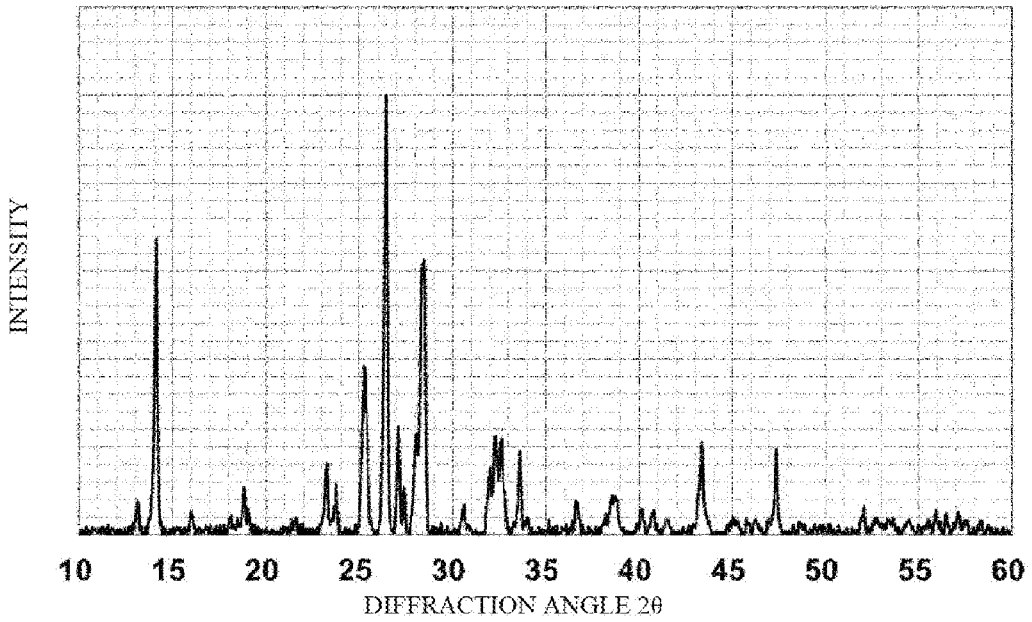
FIG. 3 is a graph representing an X-ray diffraction pattern of a catalyst (catalyst II-1-2) in Example II-1.

A stainless-steel reaction tube having an inner diameter of 25 mm was filled with the catalyst II-1-1, and an aging treatment was carried out for 6600 hours under the conditions of a propylene concentration of 8 vol % and a propylene space velocity of 160 hr$^{-1}$ with respect to all the catalysts in the reaction tube. The maximum value of the temperature of the catalyst layer in the reaction tube during the aging treatment was 428° C., and the minimum value of the oxygen concentration of the gas at the outlet of the reaction tube was 4.2 vol %. Thereafter, the mixture was taken out of the reaction tube to obtain a catalyst II-1-2. The X-ray diffraction angles (2θ) of the catalyst II-1-2 were measured. FIG. 3 is a diagram illustrating an X-ray diffraction pattern of the catalyst II-1-2.

Comparative Example II-1

Figure 4:
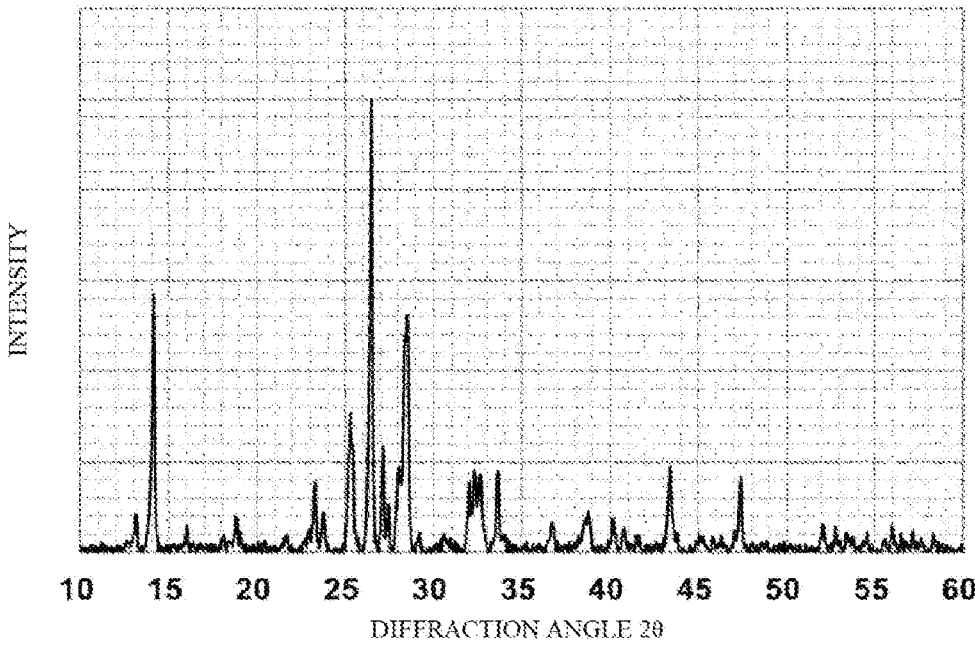
FIG. 4 is a graph representing an X-ray diffraction pattern of a catalyst (catalyst II-1-3) in Comparative Example II-1.

A stainless-steel reaction tube having an inner diameter of 25 mm was filled with the catalyst II-1-1, and an aging treatment was carried out for 1300 hours under the conditions of a propylene concentration of 8 vol % and a propylene space velocity of 160 hr$^{-1}$ with respect to all the catalysts in the reaction tube. The maximum value of the temperature of the catalyst layer in the reaction tube during the aging treatment was 444° C., and the minimum value of the oxygen concentration of the gas at the outlet of the reaction tube was 4.8 vol %. Thereafter, the mixture was taken out of the reaction tube to obtain a catalyst II-1-3. The X-ray diffraction angle (2θ) of the catalyst II-1-3 was measured. FIG. 4 is a diagram illustrating an X-ray diffraction pattern of the catalyst II-1-3.

Using the catalyst II-1-1 and the catalysts II-1-2 and II-1-3 taken out from the reaction tube after the aging treatment, an oxidation reaction of propylene was carried out by the following method to determine a conversion rate of a raw material and a useful selectivity. A stainless-steel reaction tube having an inner diameter of 18.4 mm was filled with each catalyst, and a mixed gas having a gas volume ratio of propylene:oxygen:water vapor=1:1.7:3.0 was introduced at a propylene space velocity of 400 hr$^{-1}$ with respect to all the catalysts in the reaction tube to carry out an oxidation reaction of propylene. The gas at the outlet of the reaction tube was analyzed between 100 hr and 150 hr from the start of introduction of propylene. The results of the salt bath temperature, the conversion rate of the raw material, the useful selectivity, and the XRD measurement of the catalyst II-1-1 are shown in Table 5, and the results of the salt bath temperature, the conversion rate of the raw material, the useful selectivity, and the XRD measurement of the catalysts II-1-2 and II-1-3 are shown in Table 6.

TABLE 5

| | Salt bath temperature (° C.) | Conversion rate of raw material (%) | Useful selectivity (%) | F1 |
|---|---|---|---|---|
| Catalyst II-1-1 | 400 | 49.7 | 96.6 | 25.22 |

TABLE 6

| | Salt bath temperature (° C.) | rate of raw material (%) | Useful selectivity (%) | U1 |
|---|---|---|---|---|
| Catalyst II-1-2 | 380 | 46.5 | 95.0 | 38.26 |
| Catalyst II-1-3 | 400 | 49.3 | 95.1 | 30.67 |

Q1, D1, and the amount of decrease in the useful selectivity per 1000 hours of reaction time in consideration of a reaction time T (hr) during which the oxidation reaction was carried out are shown in Table 7.

TABLE 7

| | Catalyst before aging treatment | Catalyst after aging treatment | Amount of decrease in useful selectivity (%) | Q1 | D1 |
|---|---|---|---|---|---|
| Example II-1 | Catalyst II-1-1 | Catalyst II-1-2 | −0.24 | 7.83 | 1.98 |
| Comparative Example II-1 | Catalyst II-1-1 | Catalyst II-1-3 | −1.15 | 16.62 | 4.19 |

Production Example II-2

100 parts by mass of ammonium heptamolybdate was completely dissolved in 380 parts by mass of pure water heated to 60° C. (mother liquid 1). Next, 0.17 parts by mass of potassium nitrate was dissolved in 1.5 parts by mass of pure water, and the mixture was added to the mother liquid 1. Next, 38 parts by mass of ferric nitrate, 89 parts by mass of cobalt nitrate, and 33 parts by mass of nickel nitrate were dissolved in 85 parts by mass of pure water heated to 60° C., and the mixture was added dropwise to the mother liquid 1. Subsequently, 21 parts by mass of bismuth nitrate was dissolved in an aqueous nitric acid solution prepared by adding 5.4 parts by mass of nitric acid (60 mass %) to 23 parts by mass of pure water heated to 60° C., and the mixture was added dropwise to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:0.93:2.0:6.5:2.4:0.040) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 550° C. and 4 hours to obtain a catalyst II-2-1. The X-ray diffraction angle (2θ) of the catalyst II-2-1 was measured. S3 was 11.3.

Example II-2

A stainless-steel reaction tube having an inner diameter of 25 mm was filled with the catalyst II-2-1, and an aging treatment was carried out for 26000 hours under the conditions of a propylene concentration of 8 vol % and a propylene space velocity of 95 hr$^{-1}$ with respect to all the catalysts in the reaction tube. The maximum value of the temperature of the catalyst layer in the reaction tube during the aging treatment was 384° C., and the minimum value of the oxygen concentration of the gas at the outlet of the reaction tube was 3.9 vol %. Thereafter, the mixture was taken out of the reaction tube to obtain a catalyst II-2-2. The X-ray diffraction angle (2θ) of the catalysts II-2-2 was measured.

As for the catalysts II-2-1 and II-2-2, a stainless-steel reaction tube having an inner diameter of 18.4 mm was filled with each catalyst, and a mixed gas having a gas volume ratio of propylene:oxygen:water vapor=1:1.7:3.0 was introduced at a propylene space velocity of 400 hr$^{-1}$ with respect to all the catalysts in the reaction tube to carry out an oxidation reaction of propylene. The gas at the outlet of the reaction tube was analyzed between 100 hr and 150 hr from the start of introduction of propylene. The results of the salt bath temperature, the conversion rate of the raw material, the useful selectivity, and the XRD measurement of the catalyst II-2-1 are shown in Table 8, the salt bath temperature, the conversion rate of the raw material, the useful selectivity, and the XRD measurement of the catalyst II-2-2 are shown in Table 9, and Q1, D1, and the amount of decrease of the useful selectivity per 1000 hours of the reaction time in consideration of the reaction time T (hr) during which the oxidation reaction was carried out are shown in Table 10.

TABLE 8

| | Salt bath temperature (° C.) | rate of raw material (%) | Useful selectivity (%) | F1 |
|---|---|---|---|---|
| Catalyst II-2-1 | 420 | 60.9 | 94.1 | 25.88 |

TABLE 9

| | Salt bath temperature (° C.) | rate of raw material (%) | Useful selectivity (%) | U1 |
|---|---|---|---|---|
| Catalyst II-2-2 | 440 | 59.1 | 91.6 | 29.90 |

TABLE 10

| | Catalyst before aging treatment | Catalyst after aging treatment | Amount of decrease in useful selectivity (%) | Q1 | D1 |
|---|---|---|---|---|---|
| Example II-2 | Catalyst II-2-1 | Catalyst II-2-2 | −0.096 | 0.60 | 0.16 |

Production Example II-3

100 parts by mass of ammonium heptamolybdate was completely dissolved in 380 parts by mass of pure water heated to 60° C. (mother liquid 1). Next, 0.18 parts by mass of potassium nitrate was dissolved in 1.6 parts by mass of pure water, and the mixture was added to the mother liquid 1. Next, 38 parts by mass of ferric nitrate, 89 parts by mass of cobalt nitrate, and 33 parts by mass of nickel nitrate were dissolved in 85 parts by mass of pure water heated to 60° C., and the mixture was added to the mother liquid 1. Subsequently, 16 parts by mass of bismuth nitrate was dissolved in an aqueous nitric acid solution prepared by adding 4.1 parts by mass of nitric acid (60 mass %) to 17 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:0.7:2.0:6.5:2.4:0.04) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 540° C. and 4 hours to obtain a catalyst II-3-1. The X-ray diffraction angle (2θ) of the catalyst II-3-1 was measured. F1 was 69.54.

Reference Example II-1

Stainless steel reaction tubes having an inner diameter of 22 mm were filled with 250 cm of the catalyst II-3-1 on an outlet side of the reaction tube and 100 cm of the catalyst II-1-1 on an inlet side of the reaction tube, and a temperature sensor sheath having an outer diameter of 3.2 mm was installed at a center in a plane of each reaction tube in order to measure a temperature distribution in the catalyst tank. Continuous operation was carried out at 12000 hr under the conditions of a propylene concentration of 8 vol % and a

Reference Example II-2

As for the catalyst II-1-5 obtained in Reference Example II-1, an oxidation reaction of propylene was carried out in exactly the same manner. The gas at the outlet of the reaction tube was analyzed between 20 hr and 24 hr from the start of introduction of propylene. The activity and yield of each catalyst before and after use, Q1 and D1 are shown in Table 11.

Reference Example II-3

As for the catalyst II-3-2 obtained in Reference Example II-1, an oxidation reaction of propylene was carried out in exactly the same manner. The gas at the outlet of the reaction tube was analyzed between 20 hr and 24 hr from the start of introduction of propylene. The activity and yield of each catalyst before and after use, Q1 and D1 are shown in Table 11.

TABLE 11

| | Catalyst before reaction | | | | Catalyst after reaction | | | | | |
| --- | --- | --- | --- | --- | --- | --- | --- | --- | --- | --- |
| | Catalyst name | Reaction temperature (° C.) | Conversion rate (%) of propylene | Useful yield (%) | Catalyst name | Reaction temperature (° C.) | Conversion rate (%) of propylene | Useful yield (%) | Q1 | D1 |
| Reference Example II-1 | Catalyst II-1-1 | 330 | 97.0 | 92.1 | Catalyst II-1-4 | 330 | 82.1 | 72.5 | 23.8 | 6.0 |
| Reference Example II-2 | Catalyst II-1-1 | 330 | 97.0 | 92.1 | Catalyst II-1-5 | 330 | 84.9 | 73.9 | 23.1 | 5.8 |
| Reference Example II-3 | Catalyst II-3-1 | 311 | 98.4 | 91.4 | Catalyst II-3-2 | 311 | 95.2 | 85.0 | 21.1 | 5.3 | propylene space velocity of 95 $hr^{-1}$ with respect to all catalysts in the reaction tube. During this time for 1000 hours, the maximum temperature of the catalyst layer was 391° C., and the minimum oxygen concentration of the gas at the outlet of the reaction tube was 3.9 vol %. Further, during this time, the propylene space velocity was frequently varied, and the operation of 140 $hr^{-1}$ was performed three times, and the total time of the operation was 2500 hr. A differential pressure was 30 kPaG on average. Then, the catalyst was taken out from the reaction tube, and a half of the catalysts on the inlet side of the reaction tube, from the inlet side of the reaction tube, was obtained as a catalyst II-1-4, an half of the catalysts on the inlet side of the reaction tube, from the outlet side of the reaction tube, was obtained as a catalyst II-1-5, and the catalysts on the outlet side of the reaction tube, from the inlet side of the reaction tube to 50 cm, were obtained as a catalyst II-3-2. The X-ray diffraction angle (2θ) of each catalyst was measured.

As for the catalyst II-1-4, a stainless-steel reaction tube having an inner diameter of 22 mm was filled with each catalyst in the similar manner, and a mixed gas having a gas volume ratio of propylene:oxygen:water vapor=1:1.7:3.0 was introduced at a propylene space velocity of 70 $hr^{-1}$ with respect to all the catalysts in the reaction tube to carry out an oxidation reaction of propylene. The gas at the outlet of the reaction tube was analyzed between 20 hr and 24 hr from the start of introduction of propylene. The activity and yield of each catalyst before and after use, Q1 and D1 are shown in Table 11.

Reference Example II-4

Stainless steel reaction tubes having an inner diameter of 25 mm were filled with 190 cm of the catalyst II-3-1 on an outlet side of the reaction tube and 170 cm of the catalyst II-1-1 on an inlet side of the reaction tube, and a temperature sensor sheath having an outer diameter of 3.2 mm was installed at a center in a plane of each reaction tube in order to measure a temperature distribution in the catalyst tank. Continuous operation was carried out at 13000 hr under the conditions of a propylene concentration of 8 vol % and a propylene space velocity of 190 $hr^{-1}$ with respect to all catalysts in the reaction tube. For 600 hours during this time, the maximum temperature of the catalyst layer was 429° C., and the minimum oxygen concentration of the gas at the outlet of the reaction tube was 5.0 vol %. During the reaction, an average differential pressure in the reaction tube was 50 kPaG. During the reaction, nitrogen purge for about 700 hr in terms of SV 500 $hr^{-1}$ hr was performed four times. After the reaction, the catalyst was taken out, and the catalyst on the inlet side of the reaction tube was obtained as a catalyst II-1-6. The X-ray diffraction angle (2θ) of each catalyst was measured.

As for the catalyst II-1-6, a stainless-steel reaction tube having an inner diameter of 22 mm was filled with each catalyst, and a mixed gas having a gas volume ratio of propylene:oxygen:water vapor=1:1.7:3.0 was introduced at a propylene space velocity of 70 $hr^{-1}$ with respect to all the catalysts in the reaction tube to carry out an oxidation reaction of propylene. The gas at the outlet of the reaction tube was analyzed between 20 hr and 24 hr from the start of introduction of propylene. The activity and yield of each catalyst before and after use, Q1 and D1 are shown in Table 12.

TABLE 12

| | | Catalyst before reaction | | | | Catalyst after reaction | | | | |
| --- | --- | --- | --- | --- | --- | --- | --- | --- | --- | --- |
| | Catalyst name | Reaction temperature (° C.) | Conversion rate (%) of propylene | Useful yield (%) | Catalyst name | Reaction temperature (° C.) | Conversion rate (%) of propylene | Useful yield (%) | Q1 | D1 |
| Reference Example II-4 | Catalyst II-1-1 | 330 | 97.0 | 92.1 | Catalyst II-1-6 | 330 | 88.1 | 77.6 | 21.5 | 5.4 |

Example of Third Aspect

Hereinafter, the third aspect of the present invention will be described in more detail with reference to Examples. In Examples, a conversion rate, a useful yield, a useful selectivity, and an active mass ratio were calculated according to the following formulae.

Conversion rate (%)=(number of moles of reacted propylene,t-butyl alcohol,isobutylene or n-butene)/(number of moles of supplied propylene,t-butyl alcohol,isobutylene or n-butene)×100

Useful yield (%)=(total number of moles of produced acrolein and acrylic acid,total number of moles of produced methacrolein and methacrylic acid, or total number of moles of produced butadiene)/(number of moles of supplied propylene,t-butyl alcohol,isobutylene or n-butene)×100

Useful selectivity (%)=(total number of moles of produced acrolein and acrylic acid,total number of moles of produced methacrolein and methacrylic acid, or total number of moles of produced butadiene)/(number of moles of reacted propylene,t-butyl alcohol,isobutylene or n-butene)×100

Active mass ratio (mass %)=(mass of preliminary calcined powder used for molding)/{(mass of preliminary calcined powder used for molding)+(mass of carrier used for molding)}×100

An X-ray diffraction (XRD) angle (2θ) was measured by using Ultima IV manufactured by Rigaku Corporation under conditions of an X-ray CuKα ray (λ=0.154 nm), an output of 40 kV, 30 mA, a measurement range of 10° to 60°, and a measurement rate of 10° per minute. Further, a calcination time described in each of the following examples means a holding time from a time when each calcination temperature reaches, in which a time of temperature increase and temperature decrease are not included.

Catalyst Production Example III-1

Figure 5:
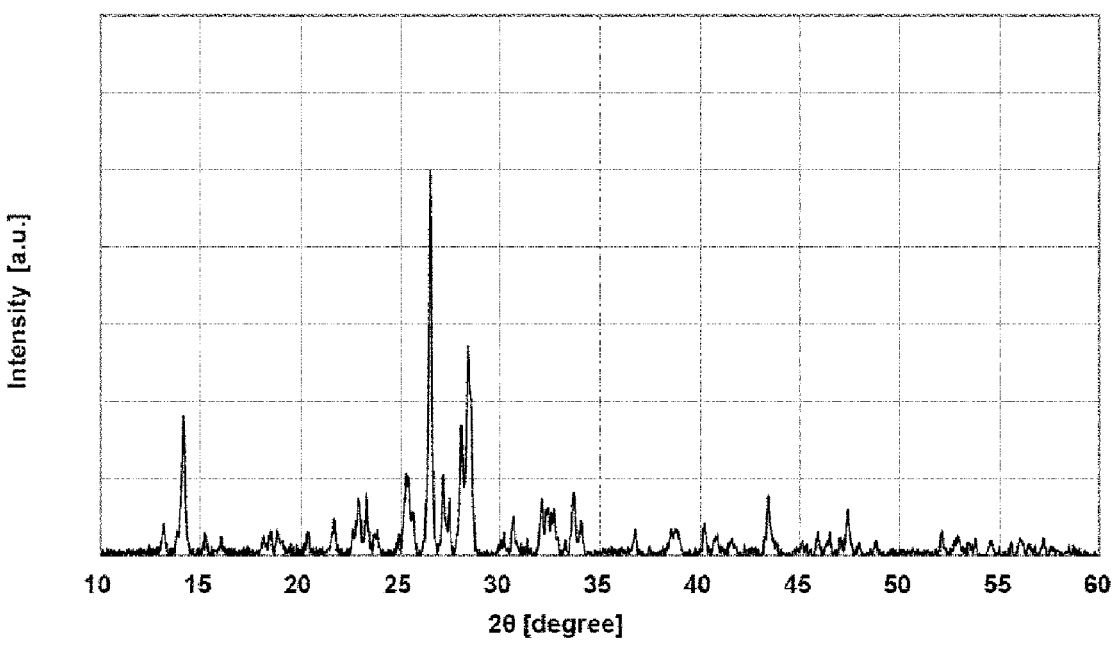
FIG. 5 is a graph representing an X-ray diffraction pattern of a catalyst III-1.

100 parts by mass of ammonium heptamolybdate was completely dissolved in 380 parts by mass of pure water heated to 80° C. (mother liquid 1). Next, 0.38 parts by mass of cesium nitrate was dissolved in 4.2 parts by mass of pure water, and the mixture was added to the mother liquid 1. Next, 37 parts by mass of ferric nitrate, 90 parts by mass of cobalt nitrate, and 33 parts by mass of nickel nitrate were dissolved in 85 parts by mass of pure water heated to 60° C., and the mixture was added to the mother liquid 1. Subsequently, 21 parts by mass of bismuth nitrate was dissolved in an aqueous nitric acid solution prepared by adding 5.4 parts by mass of nitric acid (60 mass %) to 23 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:Cs=12:0.8:2.0: 6.5:2.3:0.04) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 540° C. and 4 hours to obtain a catalyst III-1. As a result of measurement of the X-ray diffraction angle (2θ) of the catalyst III-1, it was found that S=91.7, S1=36.4, S2=21.4, S3=33.9, and S4=14.7. FIG. 5 is a diagram illustrating an X-ray diffraction pattern of the catalyst III-1.

Catalyst Production Example III-2

Figure 6:
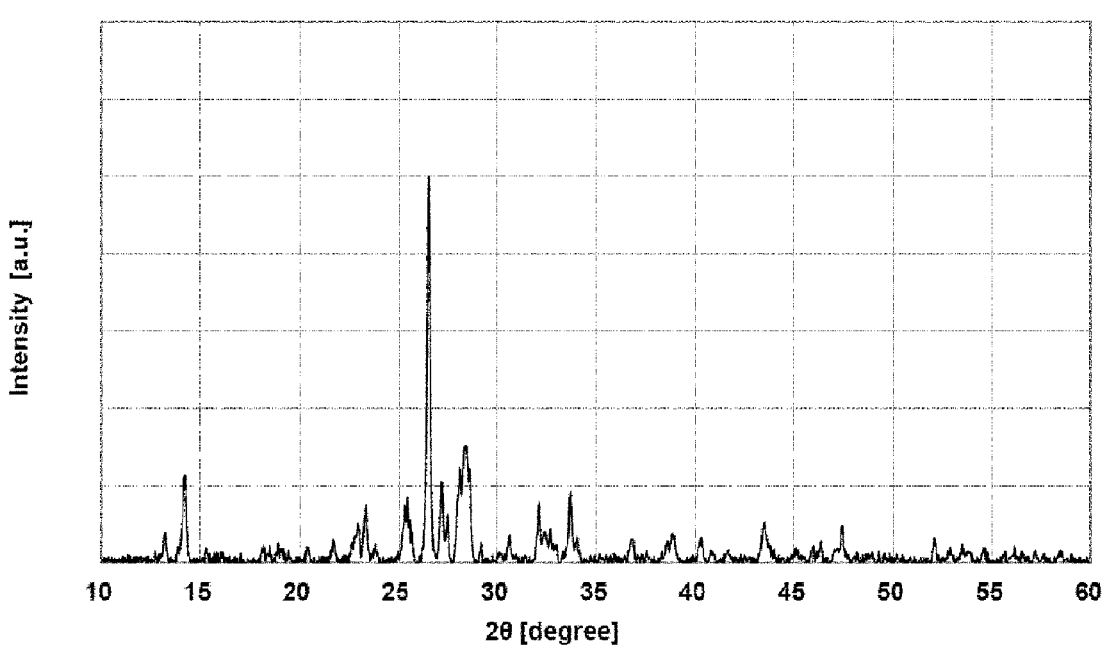
FIG. 6 is a graph representing an X-ray diffraction pattern of a catalyst III-2.

100 parts by mass of ammonium heptamolybdate was completely dissolved in 380 parts by mass of pure water heated to 60° C. (mother liquid 1). Next, 0.37 parts by mass of potassium nitrate was dissolved in 3.5 parts by mass of pure water, and the mixture was added to the mother liquid 1. Next, 34 parts by mass of ferric nitrate, 81 parts by mass of cobalt nitrate, and 44 parts by mass of nickel nitrate were dissolved in 82 parts by mass of pure water heated to 60° C., and the mixture was added to the mother liquid 1. Subsequently, 21 parts by mass of bismuth nitrate was dissolved in an aqueous nitric acid solution prepared by adding 5.8 parts by mass of nitric acid (60 mass %) to 24 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:0.9:1.8: 5.9:3.2:0.08) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 510° C. and 4 hours to obtain a catalyst III-2. As a result of measurement of the X-ray diffraction angle (2θ) of the catalyst III-2, it was found that S=69.4, S1=22.1, S2=17.1, S3=30.2, and S4=12.3. FIG. 6 is a diagram showing an X-ray diffraction pattern of the catalyst III-2.

Catalyst Production Example III-3

100 parts by mass of ammonium heptamolybdate was completely dissolved in 380 parts by mass of pure water heated to 60° C. (mother liquid 1). Next, 0.17 parts by mass of potassium nitrate was dissolved in 1.9 parts by mass of pure water, and the mixture was added to the mother liquid 1. Next, 37 parts by mass of ferric nitrate, 90 parts by mass of cobalt nitrate, and 33 parts by mass of nickel nitrate were dissolved in 85 parts by mass of pure water heated to 60° C., and the mixture was added to the mother liquid 1. Subsequently, 16 parts by mass of bismuth nitrate was dissolved in an aqueous nitric acid solution prepared by adding 4.1 parts by mass of nitric acid (60 mass %) to 17 parts by mass of pure water heated to 60° C., and the mixture was added to the mother liquid 1. The mother liquid 1 was dried by spray drying method, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:0.7:2.0: 6.5:2.4:0.04) was added to the preliminarily calcined powder, followed by thoroughly being mixed. The mixture was carried and molded into a spherical shape on an inert carrier by using a 33 mass % glycerin solution as a binder by tumbling granulation method so that an active mass ratio was 50 mass %. The thus-obtained spherical molded product having a particle size of 5.3 mm was subjected to main calcination under the conditions of 550° C. and 4 hours to obtain a catalyst III-3. As a result of measurement of the X-ray diffraction angle (2θ) of the catalyst III-3, it was found that S=113.6, S1=42.9, S2=23.8, S3=46.9, and S4=12.7.

Example III-1

A reactor including one stainless steel reaction tube having a total length of 5000 mm and a shell for passing a heating medium that covers the reaction tube was prepared in a vertical direction. From a reaction gas inlet side to a reaction gas outlet side, the reaction tube was filled in a reaction zone having a total layer length of 3500 mm by sequentially dropping, from an upper portion of the reaction tube, (first layer) a dilution catalyst layer in which 80 mass % of the catalyst III-1 and 20 mass % of an inert carrier having a particle size of 5.3 mm so as to be 800 mm in the reaction tube, (second layer) the catalyst III-1 so as to be 800 mm, and (third layer) the catalyst III-2 so as to be 1900 mm. To the reaction tube filled with the catalyst, propylene and oxygen were introduced at propylene:oxygen=1:1.7 (nitrogen and water vapor were added as inert gases to adjust the propylene concentration to 8%) and a propylene space velocity of 100 hr$^{-1}$ (standard state). After the aging reaction while keeping the temperature of the heating medium at 325° C., a propylene oxidation reaction was carried out by changing the salt bath temperature. The results are shown in Table 14.

Comparative Example III-1

A stainless-steel reaction tube was filled with a catalyst in exactly the same manner as in Example III-1 except that the third layer was changed to the catalyst III-3. Thereafter, aging was carried out in exactly the same manner as in Example III-1, and a propylene oxidation reaction was carried out. The results are shown in Table 14.

Catalyst Production Example III-4

100 parts by mass of ammonium heptamolybdate was completely dissolved in 380 parts by mass of pure water heated to 80° C. (mother liquid 1). Next, 0.18 parts by mass of potassium nitrate was dissolved in 2.0 parts by mass of pure water, and the mixture was added to the mother liquid 1. Next, 37 parts by mass of ferric nitrate, 90 parts by mass of cobalt nitrate, and 33 parts by mass of nickel nitrate were dissolved in 85 parts by mass of pure water heated to 60° C., and the mixture was added to the mother liquid 1. Subsequently, 21 parts by mass of bismuth nitrate was dissolved in an aqueous nitric acid solution prepared by adding 5.4 parts by mass of nitric acid (60 mass %) to 23 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:0.8:2.0: 6.5:2.3:0.04) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 550° C. and 4 hours to obtain a catalyst III-4. As a result of measurement of the X-ray diffraction angle (2θ) of the catalyst III-4, it was found that S=95.9, S1=35.8, S2=25.9, S3=34.2, and S4=11.3.

Example III-2

A gas inlet side of a stainless steel reaction tube having an inner diameter of 28.4 mm was filled with the catalyst III-1, a gas outlet side was filled with the catalyst III-2, and a mixed gas having a gas volume ratio of propylene:oxygen: water vapor:nitrogen=1.00:1.65:1.27:9.53 was introduced at a propylene space velocity of 100 hr$^{-1}$ with respect to all the catalysts in the reaction tube to carry out an oxidation reaction of propylene. After the aging reaction at a salt bath temperature of 315° C. for 20 hours or more from the start of the reaction, the conversion rate of the raw material and the useful yield shown in Table 14 were determined by analyzing the gas at the outlet of the reaction tube at a reaction blade temperature of 320° C.

Comparative Example III-2

A catalyst was filled and an oxidation reaction of propylene was carried out in exactly the same manner as in Example III-2 except that the catalyst on a gas outlet side was changed to the catalyst III-4. The results are shown in Table 14.

TABLE 13

| | | Catalyst | Bi | Fe | Co | Ni | K | Cs | S | S1 | S2 | S3 | S4 |
|---|---|---|---|---|---|---|---|---|---|---|---|---|---|
| | | | | | Atomic proportion with respect to Mo 12 | | | | | | XRD parameters | | |
| Example III-1 | Upper layer | Catalyst III-1 | 0.8 | 2.0 | 6.5 | 2.3 | 0.00 | 0.04 | 91.7 | 36.4 | 21.4 | 33.9 | 14.7 |
| | Middle layer | Catalyst III-1 | 0.8 | 2.0 | 6.5 | 2.3 | 0.00 | 0.04 | 91.7 | 36.4 | 21.4 | 33.9 | 14.7 |
| | Lower layer | Catalyst III-2 | 0.9 | 1.8 | 5.9 | 3.2 | 0.08 | 0.00 | 69.4 | 22.1 | 17.1 | 30.2 | 12.3 |
| Example III-2 | Upper layer | Catalyst III-1 | 0.8 | 2.0 | 6.5 | 2.3 | 0.00 | 0.04 | 91.7 | 36.4 | 21.4 | 33.9 | 14.7 |
| | Lower layer | Catalyst III-2 | 0.9 | 1.8 | 5.9 | 3.2 | 0.08 | 0.00 | 69.4 | 22.1 | 17.1 | 30.2 | 12.3 |
| Comparative Example III-1 | Upper layer | Catalyst III-1 | 0.8 | 2.0 | 6.5 | 2.3 | 0.00 | 0.04 | 91.7 | 36.4 | 21.4 | 33.9 | 14.7 |
| | Middle layer | Catalyst III-1 | 0.8 | 2.0 | 6.5 | 2.3 | 0.00 | 0.04 | 91.7 | 36.4 | 21.4 | 33.9 | 14.7 |
| | Lower layer | Catalyst III-3 | 0.7 | 2.0 | 6.5 | 2.4 | 0.04 | 0.00 | 113.6 | 42.9 | 23.8 | 46.9 | 12.7 |
| Comparative III-2 | Upper layer | Catalyst III-1 | 0.8 | 2.0 | 6.5 | 2.3 | 0.00 | 0.04 | 91.7 | 36.4 | 21.4 | 33.9 | 14.7 |
| Example | Lower layer | Catalyst III-4 | 0.8 | 2.0 | 6.5 | 2.3 | 0.04 | 0.00 | 95.9 | 35.8 | 25.9 | 34.2 | 11.3 |

TABLE 14

| | Reaction results | | |
|---|---|---|---|
| | Salt bath temperature [° C.] | Conversion rate [%] | Useful yield [%] |
| Example III-1 | 316 | 95.4 | 89.9 |
| | 320 | 97.8 | 92.0 |
| | 324 | 98.3 | 92.1 |
| Example III-2 | 320 | 97.2 | 92.1 |
| Comparative Example III-1 | 316 | 97.8 | 91.0 |
| | 320 | 98.3 | 91.2 |
| | 324 | 98.8 | 91.1 |
| Comparative Example III-2 | 320 | 98.0 | 90.9 |

From Table 14, it can be seen that a significantly high useful yield is exhibited by performing filling catalysts so that the atomic proportion of Bi is higher on the outlet side of the reaction tube than on the inlet side of the reaction tube when Mo as the catalytically active component is taken as 12. From another viewpoint, it can be seen that a significantly high useful yield is exhibited by performing filling catalysts such that the XRD parameter S is lower on the outlet side of the reaction tube than on the inlet side of the reaction tube.

Catalyst Production Example III-5

100 parts by mass of ammonium heptamolybdate was completely dissolved in 380 parts by mass of pure water heated to 80° C. (mother liquid 1). Next, 0.56 parts by mass of potassium nitrate was dissolved in 5.0 parts by mass of pure water, and the mixture was added to the mother liquid 1. Next, 33 parts by mass of ferric nitrate, 81 parts by mass of cobalt nitrate, and 44 parts by mass of nickel nitrate were dissolved in 85 parts by mass of pure water heated to 60° C., and the mixture was added to the mother liquid 1. Subsequently, 23 parts by mass of bismuth nitrate was dissolved in an aqueous nitric acid solution prepared by adding 5.8 parts by mass of nitric acid (60 mass %) to 24 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:1.0:1.8: 5.9:3.2:0.12) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 520° C. and 4 hours to obtain a catalyst III-5. As a result of measurement of the X-ray diffraction angle (2θ) of the catalyst III-5, it was found that S=91.2, S1=28.8, S2=22.9, S3=39.5, and S4=10.6.

Example III-3

A catalyst was filled and an oxidation reaction of propylene was carried out in exactly the same manner as in Example III-2 except that the catalyst on a gas outlet side was changed to the catalyst III-5. The results are shown in Table 16.

Catalyst Production Example III-6

100 parts by mass of ammonium heptamolybdate was completely dissolved in 380 parts by mass of pure water heated to 80° C. (mother liquid 1). Next, 0.44 parts by mass of potassium nitrate was dissolved in 4.0 parts by mass of pure water, and the mixture was added to the mother liquid 1. Next, 33 parts by mass of ferric nitrate, 71 parts by mass of cobalt nitrate, and 38 parts by mass of nickel nitrate were dissolved in 76 parts by mass of pure water heated to 60° C., and the mixture was added to the mother liquid 1. Subsequently, 38 parts by mass of bismuth nitrate was dissolved in an aqueous nitric acid solution prepared by adding 9.7 parts by mass of nitric acid (60 mass %) to 41 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:1.7:1.8: 5.2:2.8:0.10) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.2 mm was subjected to main calcination under the conditions of 505° C. and 4 hours to obtain a catalyst III-6. As a result of measurement of the X-ray diffraction angle (2θ) of the catalyst III-6, it was found that S=39.1, 51=21.9, S2=17.3, S3=0.0, and S4=11.4.

Comparative Example III-3

A catalyst was filled and an oxidation reaction of propylene was carried out in exactly the same manner as in Example III-2 except that the catalyst on a gas inlet side was changed to the catalyst III-6 and the catalyst on a gas outlet side was changed to the catalyst III-5. The results are shown in Table 16.

Catalyst Production Example III-7

100 parts by mass of ammonium heptamolybdate was completely dissolved in 380 parts by mass of pure water heated to 80° C. (mother liquid 1). Next, 0.37 parts by mass of potassium nitrate was dissolved in 3.3 parts by mass of pure water, and the mixture was added to the mother liquid 1. Next, 28 parts by mass of ferric nitrate, 81 parts by mass of cobalt nitrate, and 47 parts by mass of nickel nitrate were dissolved in 82 parts by mass of pure water heated to 60° C., and the mixture was added to the mother liquid 1. Subsequently, 23 parts by mass of bismuth nitrate was dissolved in an aqueous nitric acid solution prepared by adding 5.8 parts by mass of nitric acid (60 mass %) to 24 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:1.0:1.5: 5.9:3.4:0.08) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 530° C. and 4 hours to obtain a catalyst III-7. As a result of measurement of the X-ray diffraction angle (2θ) of the catalyst III-7, it was found that S=55.2, S1=14.8, S2=12.2, S3=28.2, and S4=9.4.

Example III-4

A catalyst was filled and an oxidation reaction of propylene was carried out in exactly the same manner as in Example III-2 except that the catalyst on a gas outlet side was changed to the catalyst III-7. The results are shown in Table 16.

Comparative Example III-4

A catalyst was filled and an oxidation reaction of propylene was carried out in exactly the same manner as in Comparative Example III-3 except that the catalyst on a gas outlet side was changed to the catalyst III-7. The results are shown in Table 16.

Catalyst Production Example III-8

100 parts by mass of ammonium heptamolybdate was completely dissolved in 380 parts by mass of pure water heated to 80° C. (mother liquid 1). Next, 0.27 parts by mass of potassium nitrate was dissolved in 2.5 parts by mass of pure water, and the mixture was added to the mother liquid 1. Next, 49 parts by mass of ferric nitrate, 78 parts by mass of cobalt nitrate, and 33 parts by mass of nickel nitrate were dissolved in 85 parts by mass of pure water heated to 60° C., and the mixture was added to the mother liquid 1. Subsequently, 22 parts by mass of bismuth nitrate was dissolved in an aqueous nitric acid solution prepared by adding 5.6 parts by mass of nitric acid (60 mass %) to 23 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:1.0:2.6: 5.7:2.4:0.06) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 540° C. and 4 hours to obtain a catalyst III-8. As a result of measurement of the X-ray diffraction angle (2θ) of the catalyst III-8, it was found that S=45.7, 51=26.5, S2=19.2, S3=0.0, and S4=13.0.

Example III-5

A catalyst was filled and an oxidation reaction of propylene was carried out in exactly the same manner as in Example III-2 except that the catalyst on a gas outlet side was changed to the catalyst III-8. The results are shown in Table 16.

Comparative Example III-5

A catalyst was filled and an oxidation reaction of propylene was carried out in exactly the same manner as in Comparative Example III-3 except that the catalyst on a gas outlet side was changed to the catalyst III-8. The results are shown in Table 16.

Catalyst Production Example III-9

100 parts by mass of ammonium heptamolybdate was completely dissolved in 380 parts by mass of pure water heated to 80° C. (mother liquid 1). Next, 0.65 parts by mass of potassium nitrate was dissolved in 5.7 parts by mass of pure water, and the mixture was added to the mother liquid 1. Next, 49 parts by mass of ferric nitrate, 87 parts by mass of cobalt nitrate, and 33 parts by mass of nickel nitrate were dissolved in 90 parts by mass of pure water heated to 60° C., and the mixture was added to the mother liquid 1. Subsequently, 28 parts by mass of bismuth nitrate was dissolved in an aqueous nitric acid solution prepared by adding 7.1 parts by mass of nitric acid (60 mass %) to 30 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:1.2:2.6:6.3:2.4:0.14) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 540° C. and 4 hours to obtain a catalyst III-9. As a result of measurement of the X-ray diffraction angle (2θ) of the catalyst III-9, it was found that S=54.1, S1=29.3, S2=24.8, S3=0.0, and S4=15.0.

Example III-6

A catalyst was filled and an oxidation reaction of propylene was carried out in exactly the same manner as in Example III-2 except that the catalyst on a gas outlet side was changed to the catalyst III-9. The results are shown in Table 16.

Comparative Example III-6

A catalyst was filled and an oxidation reaction of propylene was carried out in exactly the same manner as in Comparative Example III-3 except that the catalyst on a gas outlet side was changed to the catalyst III-9. The results are shown in Table 16.

Catalyst Production Example III-10

100 parts by mass of ammonium heptamolybdate was completely dissolved in 380 parts by mass of pure water heated to 80° C. (mother liquid 1). Next, 0.37 parts by mass of potassium nitrate was dissolved in 3.3 parts by mass of pure water, and the mixture was added to the mother liquid 1. Next, 48 parts by mass of ferric nitrate, 62 parts by mass of cobalt nitrate, and 38 parts by mass of nickel nitrate were dissolved in 78 parts by mass of pure water heated to 60° C., and the mixture was added to the mother liquid 1. Subsequently, 30 parts by mass of bismuth nitrate was dissolved in an aqueous nitric acid solution prepared by adding 7.6 parts by mass of nitric acid (60 mass %) to 32 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:1.3:2.5:4.5:2.8:0.08) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 530° C. and 4 hours to obtain a catalyst III-10. As a result of measurement of the X-ray diffraction angle (2θ) of the catalyst III-10, it was found that S=70.4, S1=0.0, S2=24.8, S3=45.5, and S4=19.0.

Example III-7

A catalyst was filled and an oxidation reaction of propylene was carried out in exactly the same manner as in Example III-2 except that the catalyst on a gas outlet side was changed to the catalyst III-10. The results are shown in Table 16.

Comparative Example III-7

A catalyst was filled and an oxidation reaction of propylene was carried out in exactly the same manner as in Comparative Example III-3 except that the catalyst on a gas outlet side was changed to the catalyst III-10. The results are shown in Table 16.

Catalyst Production Example III-11

100 parts by mass of ammonium heptamolybdate was completely dissolved in 380 parts by mass of pure water heated to 80° C. (mother liquid 1). Next, 0.22 parts by mass of potassium nitrate was dissolved in 2.0 parts by mass of pure water, and the mixture was added to the mother liquid 1. Next, 36 parts by mass of ferric nitrate, 77 parts by mass of cobalt nitrate, and 44 parts by mass of nickel nitrate were dissolved in 83 parts by mass of pure water heated to 60° C., and the mixture was added to the mother liquid 1. Subsequently, 30 parts by mass of bismuth nitrate was dissolved in an aqueous nitric acid solution prepared by adding 7.6 parts by mass of nitric acid (60 mass %) to 32 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:1.3:1.9:5.6:3.2:0.05) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 540° C. and 4 hours to obtain a catalyst III-11. As a result of measurement of the X-ray diffraction angle (2θ) of the catalyst III-11, it was found that S=68.8, S1=0.0, S2=16.8, S3=52.0, and S4=0.0.

Example III-8

A catalyst was filled and an oxidation reaction of propylene was carried out in exactly the same manner as in Example III-2 except that the catalyst on a gas outlet side was changed to the catalyst III-11. The results are shown in Table 16.

Comparative Example III-8

A catalyst was filled and an oxidation reaction of propylene was carried out in exactly the same manner as in Comparative Example III-3 except that the catalyst on a gas outlet side was changed to the catalyst III-11. The results are shown in Table 16.

Catalyst Production Example III-12

100 parts by mass of ammonium heptamolybdate was completely dissolved in 380 parts by mass of pure water heated to 80° C. (mother liquid 1). Next, 0.22 parts by mass of potassium nitrate was dissolved in 2.0 parts by mass of pure water, and the mixture was added to the mother liquid 1. Next, 31 parts by mass of ferric nitrate, 77 parts by mass of cobalt nitrate, and 44 parts by mass of nickel nitrate were dissolved in 80 parts by mass of pure water heated to 60° C., and the mixture was added to the mother liquid 1. Subsequently, 23 parts by mass of bismuth nitrate was dissolved in an aqueous nitric acid solution prepared by adding 5.8 parts by mass of nitric acid (60 mass %) to 24 parts by mass of pure water heated to 60° C., and the mixture was added to the mother liquid 1. The mother liquid 1 was dried by spray drying, and the obtained dried powder was preliminary calcined at 440° C. for 4 hours. Five mass % of a crystalline cellulose with respect to the preliminarily calcined powder (the atomic proportion calculated from the charged raw materials was Mo:Bi:Fe:Co:Ni:K=12:1.0:1.6:5.6:3.2:0.05) was added to the preliminarily calcined powder, followed by thoroughly being mixed. The mixture was carried and molded into a spherical shape on an inert carrier by using a 33 mass % glycerin solution as a binder by tumbling granulation so that an active mass ratio was 50 mass %. The thus-obtained spherical molded product having a particle size of 5.3 mm was subjected to main calcination under the conditions of 520° C. and 4 hours to obtain a catalyst III-12. As a result of measurement of the X-ray diffraction angle (2θ) of the catalyst III-12, it was found that S=70.0, S1=27.8, S2=14.0, S3=28.2, and S4=13.5.

Example III-9

A catalyst was filled and an oxidation reaction of propylene was carried out in exactly the same manner as in Example III-2 except that the catalyst on a gas outlet side was changed to the catalyst III-12. The results are shown in Table 16.

Comparative Example III-9

A catalyst was filled and an oxidation reaction of propylene was carried out in exactly the same manner as in Comparative Example III-3 except that the catalyst on a gas outlet side was changed to the catalyst III-12. The results are shown in Table 16.

TABLE 15

| | | Catalyst | Atomic proportion with respect to Mo 12 | | | | | | XRD parameters | | | | |
|---|---|---|---|---|---|---|---|---|---|---|---|---|---|
| | | | Bi | Fe | Co | Ni | K | Cs | S | S1 | S2 | S3 | S4 |
| Example III-3 | Upper layer | Catalyst III-1 | 0.8 | 2.0 | 6.5 | 2.3 | 0.00 | 0.04 | 91.7 | 36.4 | 21.4 | 33.9 | 14.7 |
| | Lower layer | Catalyst III-5 | 1.0 | 1.8 | 5.9 | 3.2 | 0.12 | 0.00 | 91.2 | 28.8 | 22.9 | 39.5 | 10.6 |
| Example III-4 | Upper layer | Catalyst III-1 | 0.8 | 2.0 | 6.5 | 2.3 | 0.00 | 0.04 | 91.7 | 36.4 | 21.4 | 33.9 | 14.7 |
| | Lower layer | Catalyst III-7 | 1.0 | 1.5 | 5.9 | 3.4 | 0.08 | 0.00 | 55.2 | 14.8 | 12.2 | 28.2 | 9.4 |
| Example III-5 | Upper layer | Catalyst III-1 | 0.8 | 2.0 | 6.5 | 2.3 | 0.00 | 0.04 | 91.7 | 36.4 | 21.4 | 33.9 | 14.7 |
| | Lower layer | Catalyst III-8 | 1.0 | 2.6 | 5.7 | 2.4 | 0.06 | 0.00 | 45.7 | 26.5 | 19.2 | 0.0 | 13.0 |
| Example III-6 | Upper layer | Catalyst III-1 | 0.8 | 2.0 | 6.5 | 2.3 | 0.00 | 0.04 | 91.7 | 36.4 | 21.4 | 33.9 | 14.7 |
| | Lower layer | Catalyst III-9 | 1.2 | 2.6 | 6.3 | 2.4 | 0.14 | 0.00 | 54.1 | 29.3 | 24.8 | 0.0 | 15.0 |
| Example III-7 | Upper layer | Catalyst III-1 | 0.8 | 2.0 | 6.5 | 2.3 | 0.00 | 0.04 | 91.7 | 36.4 | 21.4 | 33.9 | 14.7 |
| | Lower layer | Catalyst III-10 | 1.3 | 2.5 | 4.5 | 2.8 | 0.08 | 0.00 | 70.4 | 0.0 | 24.8 | 45.5 | 19.0 |
| Example III-8 | Upper layer | Catalyst III-1 | 0.8 | 2.0 | 6.5 | 2.3 | 0.00 | 0.04 | 91.7 | 36.4 | 21.4 | 33.9 | 14.7 |
| | Lower layer | Catalyst III-11 | 1.3 | 1.9 | 5.6 | 3.2 | 0.05 | 0.00 | 68.8 | 0.0 | 16.8 | 52.0 | 0.0 |
| Example III-9 | Upper layer | Catalyst III-1 | 0.8 | 2.0 | 6.5 | 2.3 | 0.00 | 0.04 | 91.7 | 36.4 | 21.4 | 33.9 | 14.7 |
| | Lower layer | Catalyst III-12 | 1.0 | 1.6 | 5.6 | 3.2 | 0.05 | 0.00 | 70.0 | 27.8 | 14.0 | 28.2 | 13.5 |
| Comparative Example III-3 | Upper layer | Catalyst III-6 | 1.7 | 1.8 | 5.2 | 2.8 | 0.10 | 0.00 | 39.1 | 21.9 | 17.3 | 0.0 | 11.4 |
| | Lower layer | Catalyst III-5 | 1.0 | 1.8 | 5.9 | 3.2 | 0.12 | 0.00 | 91.2 | 28.8 | 22.9 | 39.5 | 10.6 |
| Comparative Example III-4 | Upper layer | Catalyst III-6 | 1.7 | 1.8 | 5.2 | 2.8 | 0.10 | 0.00 | 39.1 | 21.9 | 17.3 | 0.0 | 11.4 |
| | Lower layer | Catalyst III-7 | 1.0 | 1.5 | 5.9 | 3.4 | 0.08 | 0.00 | 55.2 | 14.8 | 12.2 | 28.2 | 9.4 |
| Comparative Example III-5 | Upper layer | Catalyst III-6 | 1.7 | 1.8 | 5.2 | 2.8 | 0.10 | 0.00 | 39.1 | 21.9 | 17.3 | 0.0 | 11.4 |
| | Lower layer | Catalyst III-8 | 1.0 | 2.6 | 5.7 | 2.4 | 0.06 | 0.00 | 45.7 | 26.5 | 19.2 | 0.0 | 13.0 |

TABLE 15-continued

| | | Catalyst | Bi | Fe | Co | Ni | K | Cs | S | S1 | S2 | S3 | S4 |
|---|---|---|---|---|---|---|---|---|---|---|---|---|---|
| | | | | | | Atomic proportion with respect to Mo 12 | | | XRD parameters | | | | |
| Comparative Example III-6 | Upper layer | Catalyst III-6 | 1.7 | 1.8 | 5.2 | 2.8 | 0.10 | 0.00 | 39.1 | 21.9 | 17.3 | 0.0 | 11.4 |
| | Lower layer | Catalyst III-9 | 1.2 | 2.6 | 6.3 | 2.4 | 0.14 | 0.00 | 54.1 | 29.3 | 24.8 | 0.0 | 15.0 |
| Comparative Example III-7 | Upper layer | Catalyst III-6 | 1.7 | 1.8 | 5.2 | 2.8 | 0.10 | 0.00 | 39.1 | 21.9 | 17.3 | 0.0 | 11.4 |
| | Lower layer | Catalyst III-10 | 1.3 | 2.5 | 4.5 | 2.8 | 0.08 | 0.00 | 70.4 | 0.0 | 24.8 | 45.5 | 19.0 |
| Comparative Example III-8 | Upper layer | Catalyst III-6 | 1.7 | 1.8 | 5.2 | 2.8 | 0.10 | 0.00 | 39.1 | 21.9 | 17.3 | 0.0 | 11.4 |
| | Lower layer | Catalyst III-11 | 1.3 | 1.9 | 5.6 | 3.2 | 0.05 | 0.00 | 68.8 | 0.0 | 16.8 | 52.0 | 0.0 |
| Comparative Example III-9 | Upper layer | Catalyst III-6 | 1.7 | 1.8 | 5.2 | 2.8 | 0.10 | 0.00 | 39.1 | 21.9 | 17.3 | 0.0 | 11.4 |
| | Lower layer | Catalyst III-12 | 1.0 | 1.6 | 5.6 | 3.2 | 0.05 | 0.00 | 70.0 | 27.8 | 14.0 | 28.2 | 13.5 |

TABLE 16

| | Catalyst | Reaction results | | |
|---|---|---|---|---|
| | | Salt bath temperature [° C.] | Conversion rate [%] | Useful yield (%) |
| Example III-3 Upper layer | Catalyst III-1 | 320 | 97.2 | 92.5 |
| Lower layer | Catalyst III-5 | | | |
| Example III-4 Upper layer | Catalyst III-1 | 320 | 97.0 | 92.6 |
| Lower layer | Catalyst III-7 | | | |
| Example III-5 Upper layer | Catalyst III-1 | 320 | 97.0 | 88.3 |
| Lower layer | Catalyst III-8 | | | |
| Example III-6 Upper layer | Catalyst III-1 | 320 | 93.3 | 88.8 |
| Lower layer | Catalyst III-9 | | | |
| Example III-7 Upper layer | Catalyst III-1 | 320 | 90.7 | 86.9 |
| Lower layer | Catalyst III-10 | | | |
| Example III-8 Upper layer | Catalyst III-1 | 320 | 94.3 | 90.2 |
| Lower layer | Catalyst III-11 | | | |
| Example III-9 Upper layer | Catalyst III-1 | 320 | 95.8 | 91.2 |
| Lower layer | Catalyst III-12 | | | |
| Comparative Upper layer Example III-3 Lower layer | Catalyst III-6 Catalyst III-5 | 320 | 96.6 | 91.5 |
| Comparative Upper layer Example III-4 Lower layer | Catalyst III-6 Catalyst III-7 | 320 | 97.0 | 91.7 |
| Comparative Upper layer Example III-5 Lower layer | Catalyst III-6 Catalyst III-8 | 320 | 97.3 | 87.6 |
| Comparative Upper layer Example III-6 Lower layer | Catalyst III-6 Catalyst III-9 | 320 | 94.3 | 88.7 |
| Comparative Upper layer Example III-7 Lower layer | Catalyst III-6 Catalyst III-10 | 320 | 89.5 | 85.4 |
| Comparative Upper layer Example III-8 Lower layer | Catalyst III-6 Catalyst III-11 | 320 | 94.9 | 89.8 |
| Comparative Upper layer Example II-9 Lower layer | Catalyst III-6 Catalyst III-12 | 320 | 94.0 | 89.3 |

From Table 16, it can be seen that a significantly high useful yield is exhibited by filling the catalysts such that the atomic proportion of Bi is higher on the outlet side of the reaction tube than on the inlet side of the reaction tube when the component amount of Mo as the catalytically active component is taken as 12. From another viewpoint, it can be seen that a significantly high useful yield is exhibited by filling the catalysts such that the XRD parameter S of the catalyst is lower on the outlet side of the reaction tube than on the inlet side of the reaction tube.

Although the present invention has been described in detail with reference to specific examples, it is apparent to those skilled in the art that it is possible to add various alterations and modifications without departing from the spirit and the scope of the present invention.

The present application is based on Japanese Patent Application (No. 2020-002507 and 2020-002509) filed on Jan. 10, 2020, and Patent Application (No. 2020-42592) filed on Mar. 12, 2020, the entire contents of which are incorporated herein by reference. In addition, all references cited here are entirely incorporated.

INDUSTRIAL APPLICABILITY

Using the present invention allows for achieving a high yield when an unsaturated aldehyde compound, an unsaturated carboxylic acid compound, or a conjugated diene compound is produced by a partial oxidation reaction.

The invention claimed is:

1. A catalyst comprising, a catalytically active component carried on an inert carrier, wherein a composition of the catalytically active component is represented by the following formula (I-1):

$$Mo_{a1}Bi_{b1}Ni_{c1}Co_{d1}Fe_{e1}X_{f1}Y_{g1}Z_{h1}O_{i1} \qquad (I\text{-}1)$$

wherein, in the formula (I-1), Mo, Bi, Ni, Co and Fe represent molybdenum, bismuth, nickel, cobalt and iron, respectively; X is at least one element selected from the group consisting of tungsten, antimony, tin, zinc, chromium, manganese, magnesium, silica, aluminum, cerium and titanium; Y is at least one element selected from the group consisting of sodium, potassium, cesium, rubidium, and thallium; Z belongs to the 1st to 16th groups in the periodic table and means at least one element selected from elements other than the above Mo, Bi, Ni, Co, Fe, X, and Y; $a1$, $b1$, $c1$, $d1$, $e1$, $f1$, $g1$, $h1$, and $i1$ represent the number of atoms of molybdenum, bismuth, nickel, cobalt, iron, X, Y, Z, and oxygen, respectively; when $a1=12$, $0<b1\leq7$, $0\leq c1\leq10$, $0<d1\leq10$, $8.3\leq c1+d1\leq9.4$, $0\leq e1\leq5$, $0\leq f1\leq2$, $0\leq g1\leq3$, $0\leq h1\leq5$, and $i1$ is a value determined by an oxidation state of each element, and a sum(S) of ratios of peak intensities expressed by the following formula in an X-ray diffraction pattern obtained by using CuKα rays as an X-ray source is 42 or more and 113 or less, $S=\{$(peak intensity at $2\theta=14.1°\pm0.1°$)+(peak intensity at $2\theta=25.4°+0.1°$)+(peak intensity at $2\theta=28.5°\pm0.1°$)$\}$/(peak intensity at $2\theta=26.5°\pm0.1°$)×100.

2. The catalyst according to claim 1, wherein a ratio (S4) of a peak intensity expressed by the following formula is 2 or more and 16 or less, $S4=$(peak intensity at $2\theta=27.4°\pm0.1°$)/(peak intensity at $2\theta=26.5°\pm0.1°$)×100.

3. The catalyst according to claim 1, wherein the inert carrier is silica, alumina, or a combination thereof.

4. The catalyst according to claim 1, which is a catalyst for producing at least one of an unsaturated aldehyde compound, an unsaturated carboxylic acid compound, and a conjugated diene.

5. A method for producing at least one of an unsaturated aldehyde compound, an unsaturated carboxylic acid compound, and a conjugated diene using the catalyst according to claim 1.

6. The method according to claim 5, wherein the unsaturated aldehyde compound is acrolein, the unsaturated carboxylic acid compound is acrylic acid, and the conjugated diene is 1,3-butadiene.

7. An unsaturated aldehyde compound, an unsaturated carboxylic acid compound, or a conjugated diene produced using the catalyst according to claim 1.

* * * * *